United States Patent
Masuyama et al.

(10) Patent No.: US 8,173,350 B2
(45) Date of Patent: May 8, 2012

(54) OXIME COMPOUND AND RESIST COMPOSITION CONTAINING THE SAME

(75) Inventors: Tatsuro Masuyama, Toyonaka (JP); Kazuhiko Hashimoto, Toyonaka (JP); Takashi Hiraoka, Hannan (JP); Ichiki Takemoto, Kawanishi (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 316 days.

(21) Appl. No.: 12/506,925

(22) Filed: Jul. 21, 2009

(65) Prior Publication Data

US 2010/0021847 A1  Jan. 28, 2010

(30) Foreign Application Priority Data

Jul. 28, 2008  (JP) ................. 2008-193202
Dec. 12, 2008  (JP) ................. 2008-316757

(51) Int. Cl.
G03F 7/004 (2006.01)
G03F 7/039 (2006.01)
C07C 303/28 (2006.01)
C07C 309/65 (2006.01)
C08F 12/20 (2006.01)

(52) U.S. Cl. ............ 430/270.1; 430/326; 430/910; 430/919; 430/921; 430/925; 558/48; 558/54; 549/419; 549/426; 549/428; 526/243; 526/248; 526/287; 526/288

(58) Field of Classification Search ............... None
See application file for complete search history.

(56) References Cited

U.S. PATENT DOCUMENTS 5,759,740 A * 6/1998 Munzel et al. ............. 430/270.1
7,399,577 B2 7/2008 Yamato et al. ............... 430/311
7,531,290 B2 5/2009 Kobayashi et al.
2006/0246377 A1 11/2006 Yamato et al. ............... 430/311
2007/0099112 A1 5/2007 Kobayashi et al.
2008/0085458 A1 4/2008 Yamato et al.
2009/0042114 A1 2/2009 Yamato et al. ................. 430/7

FOREIGN PATENT DOCUMENTS

JP       2008-163218       * 7/2008
WO   WO 2004/074242 A2    9/2004
WO        2007148623 A1   12/2007

OTHER PUBLICATIONS

JPO English abstract for JP2008-163218 (Jul. 2008).*

* cited by examiner

*Primary Examiner* — Sin J. Lee
(74) *Attorney, Agent, or Firm* — Hogan Lovells US LLP

(57) ABSTRACT

An oxime compound represented by the formula (I):

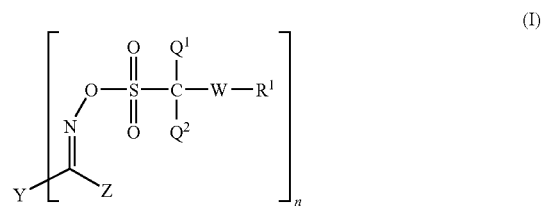

wherein Y represents an unsubstituted or substituted n-valent C6-C14 aromatic hydrocarbon group, n represents an integer of 1 to 6, $R^1$ represents a C1-C30 aliphatic hydrocarbon group etc., $R^2$ represents a linear or branched chain C1-C20 aliphatic hydrocarbon group etc., W represents —CO—O— etc., $Q^1$ and $Q^2$ each independently represent a fluorine atom etc., Z represents a C1-C20 halogenated aliphatic hydrocarbon group etc, and the resist composition containing the same.

21 Claims, No Drawings

OXIME COMPOUND AND RESIST COMPOSITION CONTAINING THE SAME

This nonprovisional application claims priority under 35 U.S.C. §119(a) on Patent Application No. 2008-193202 filed in JAPAN on Jul. 28, 2008, and Patent Application No. 2008-316757 filed in JAPAN on Dec. 12, 2008, the entire contents of which are hereby incorporated by reference.

FIELD OF THE INVENTION

The present invention relates to an oxime compound and a resist composition containing the same.

BACKGROUND OF THE INVENTION

WO 2004/074242 A2 discloses an oxime compound having a perfluoroalkylsulfonyloxy group, which is used as an acid generator.

SUMMARY OF THE INVENTION

An object of the present invention is to provide a novel oxime compound and a resist composition containing the same.

The present invention relates to the followings:
<1> An oxime compound represented by the formula (I):

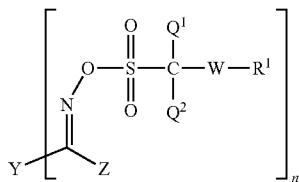

wherein Y represents an unsubstituted or substituted n-valent C6-C14 aromatic hydrocarbon group, n represents an integer of 1 to 6,
$R^1$ represents a C1-C30 aliphatic hydrocarbon group, a C6-C14 aromatic hydrocarbon group, a C4-C10 heteroaromatic hydrocarbon group, a C1-C20 alkyl group having a C6-C14 aromatic hydrocarbon group or a C1-C20 alkyl group having a C4-C10 heteroaromatic hydrocarbon group, and one or more methylene groups in the aliphatic hydrocarbon groups may be replaced by —O—, —S—, —CO—, —CO—O—, —SO$_2$— or —N(R$^c$)—, and the aliphatic hydrocarbon group, the aromatic hydrocarbon group, the heteroaromatic hydrocarbon group and the alkyl group may be respectively substituted with at least one selected from the group consisting of a hydroxyl group, an acryloyloxy group, a methacryloyloxy group, a halogen atom, a cyano group, —OR$^2$, —CO—OR$^2$—O—CO—OR$^2$, —O—CO—R$^2$, —SO$_2$—OR$^2$, —O—SO$_2$—R$^2$ and —SO$_2$R$^2$,
$R^2$ represents a linear or branched chain C1-C20 aliphatic hydrocarbon group in which one or more methylene groups may be replaced by —O—, —S—, —CO—, —CO—O— or —N(R$^c$)—, and which may be substituted with at least one selected from the group consisting of a hydroxyl group, an acryloyloxy group and a methacryloyloxy group,
$R^c$ represents a hydrogen atom or a linear or branched chain C1-C4 aliphatic hydrocarbon group,
W represents —CO—O—, —CH$_2$O— or —CH$_2$O—CO—
$Q^1$ and $Q^2$ each independently represent a fluorine atom or a C1-C6 perfluoroalkyl group,
Z represents a C1-C20 halogenated aliphatic hydrocarbon group, a C6-C14 halogenated aromatic hydrocarbon group, a cyano group, —CX$_2$—R$^1$ or —CX$_2$—SO$_2$—R$^1$, and X represents a halogen atom or a C1-C20 halogenated aliphatic hydrocarbon group;
<2> The oxime compound according to <1>, wherein n is 1;
<3> The oxime compound according to <1>, wherein the unsubstituted or substituted n-valent C6-C14 aromatic hydrocarbon group is an unsubstituted or substituted phenyl group, an unsubstituted or substituted naphthyl group, an unsubstituted or substituted biphenyl group, an unsubstituted or substituted anthryl group, an unsubstituted or substituted fluorenyl group or an unsubstituted or substituted phenanthryl group;
<4> The oxime compound according to <1>, <2> or <3>, wherein z is a C1-C20 halogenated aliphatic hydrocarbon group or a C6-C14 halogenated aromatic hydrocarbon group;
<5> The oxime compound according to any one of <1> to <4>, wherein $Q^1$ and $Q^2$ each independently represent a fluorine atom or a trifluoromethyl group;
<6> The oxime compound according to any one of <1> to <5>, wherein $R^1$ is a C1-C30 aliphatic hydrocarbon group in which one or more methylene groups may be replaced by —O—, —S— or —N(R$^c$)—, and which may be substituted with at least one selected from the group consisting of a hydroxyl group and a halogen atom;
<7> The oxime compound according to any one of <1> to <5>, wherein $R^1$ is a C1-C30 aliphatic hydrocarbon group in which one or more methylene groups are replaced by —CO—;
<8> The oxime compound according to any one of <1> to <5>, wherein $R^1$ is a C1-C30 aliphatic hydrocarbon group having an acryloyloxy group or a methacryloyloxy group, and one or more methylene groups in the aliphatic hydrocarbon group may be replaced by —O—, —S—, —N(R$^c$)—, —CO— or —CO—O—;
<9> The oxime compound according to <1>, wherein the oxime compound represented by the formula (I) is an oxime compound represented by the formula (III):

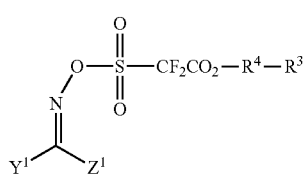

wherein $Y^1$ represents a phenyl group which may be substituted with a C1-C20 aliphatic hydrocarbon group having an acryloyloxy group or a methacryloyloxy group, a naphthyl group which may be substituted with a C1-C20 aliphatic hydrocarbon group having an acryloyloxy group or a methacryloyloxy group, a biphenyl group which may be substituted with a C1-C20 aliphatic hydrocarbon group having an acryloyloxy group or a methacryloyloxy group, an anthryl group which may be substituted with a C1-C20 aliphatic hydrocarbon group having an acryloyloxy group or a methacryloyloxy group, a fluorenyl group which may be substituted with a C1-C20 aliphatic hydrocarbon group having an acryloyloxy group or a methacryloyloxy group or a phenanthryl group which may be substituted with a C1-C20 aliphatic hydrocarbon group having an acryloyloxy group or a methacryloyloxy group, and one or more methylene groups in the C1-C20 aliphatic hydrocarbon group may be replaced by —O—, —S—, —N(R^c)—, —CO— or —CO—O—, R^c represents a hydrogen atom or a linear or branched chain C1-C4 aliphatic hydrocarbon group, $Z^1$ represents a C1-C20 halogenated aliphatic hydrocarbon group or a C6-C14 halogenated aromatic hydrocarbon group, $R^3$ represents a C3-C30 monocyclic or polycyclic aliphatic hydrocarbon group in which one or more methylene groups may be replaced by —O— or —CO—, and which may be substituted with a hydroxyl group, $R^4$ represents a single bond or a C1-C20 divalent aliphatic hydrocarbon group in which one or more methylene groups may be replaced by —O—, —S— or —N(R^c)—;

<10> The oxime compound according to <9>, wherein $Y^1$ is a phenyl group, a naphthyl group, a biphenyl group, an anthryl group, a fluorenyl group or a phenanthryl group;

<11> The oxime compound according to <9> or <10>, wherein $R^3$ is a C3-C30 monocyclic or polycyclic aliphatic hydrocarbon group in which one or more methylene groups is replaced by —CO—;

<12> The oxime compound according to <1>, wherein the oxime compound represented by the formula (I) is an oxime compound represented by the formula (Va):

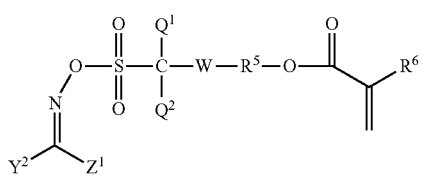

(Va)

wherein $Y^2$ represents an unsubstituted or substituted phenyl group, an unsubstituted or substituted naphthyl group, an unsubstituted or substituted biphenyl group, an unsubstituted or substituted anthryl group, an unsubstituted or substituted fluorenyl group or an unsubstituted or substituted phenanthryl group, $Z^1$ represents a C1-C20 halogenated aliphatic hydrocarbon group or a C6-C14 halogenated aromatic hydrocarbon group, $R^5$ represents a C1-C30 divalent aliphatic hydrocarbon group in which one or more methylene groups may be replaced by —O—, —S— or —N(R^c)—, R^c represents a hydrogen atom or a linear or branched chain C1-C4 aliphatic hydrocarbon group, $R^6$ represents a hydrogen atom or a methyl group, W represents —CO—O—, —CH₂O— or —CH₂O—CO—, and $Q^1$ and $Q^2$ each independently represent a fluorine atom or a C1-C6 perfluoroalkyl group;

<13> The oxime compound according to <12>, wherein $Q^1$ and $Q^2$ are fluorine atoms and W is —CO—O—;

<14> The oxime compound according to <12> or <13>, wherein $R^5$ is a C1-C20 divalent aliphatic hydrocarbon group in which one or more methylene groups may be replaced by —O—, —S— or —N(R^c)—;

<15> A polymer comprising a structural unit derived from an oxime compound according to any one of <12> to <14>;

<16> The polymer according to <15>, wherein the polymer contains a structural unit having an acid-labile group in addition to the structural unit derived from an oxime compound according to any one of <12> to <14>;

<17> A resist composition comprising a resin and an oxime compound according to any of <1> to <14>;

<18> A resist composition comprising a resin and a polymer according to <15> or <16>;

<19> The resist composition according to <17> or <18>, wherein the resin is a resin comprising a structural unit having an acid-labile group and being insoluble or poorly soluble in an aqueous alkali solution but becoming soluble in an aqueous alkali solution by the action of an acid;

<20> The resist composition according to <17> or <18>, wherein the resin further contains the other acid generator;

<21> A process for producing an oxime compound represented by the formula (I):

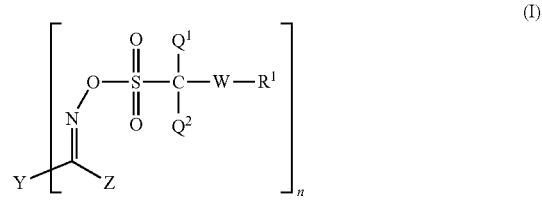

(I)

wherein Y represents an unsubstituted or substituted n-valent C6-C14 aromatic hydrocarbon group, n represents an integer of 1 to 6, $R^1$ represents a C1-C30 aliphatic hydrocarbon group, a C6-C14 aromatic hydrocarbon group, a C4-C10 heteroaromatic hydrocarbon group, a C1-C20 alkyl group having a C6-C14 aromatic hydrocarbon group or a C1-C20 alkyl group having a C4-C10 heteroaromatic hydrocarbon group, and one or more methylene groups in the aliphatic hydrocarbon groups may be replaced by —O—, —S—, —CO—, —CO—O—, —SO₂— or —N(R^c)—, and the aliphatic hydrocarbon group, the aromatic hydrocarbon group, the heteroaromatic hydrocarbon group and the alkyl group may be respectively substituted with at least one selected from the group consisting of a hydroxyl group, an acryloyloxy group, a methacryloyloxy group, a halogen atom, a cyano group, —OR², —CO—OR², —O—CO—OR², —O—CO—R², —SO₂—OR²—O—SO₂—R² and —SO₂R², $R^2$ represents a linear or branched chain C1-C20 aliphatic hydrocarbon group in which one or more methylene groups may be replaced by —O—, —S—, —CO—, —CO—O— or —N(R^c)—, and which may be substituted with at least one selected from the group consisting of a hydroxyl group, an acryloyloxy group and a methacryloyloxy group, R^c represents a hydrogen atom or a linear or branched chain C1-C4 aliphatic hydrocarbon group, W represents —CO—O—, —CH₂O— or —CH₂O—CO—

$Q^1$ and $Q^2$ each independently represent a fluorine atom or a C1-C6 perfluoroalkyl group, z represents a C1-C20 halogenated aliphatic hydrocarbon group, a C6-C14 halogenated aromatic hydrocarbon group, a cyano group, —CX₂—R¹ or —CX₂—SO₂—R¹, and X represents a halogen atom or a C1-C20 halogenated aliphatic hydrocarbon group, which comprises reacting a compound represented by the formula (VII):

(VII)

wherein Y, Z and n are the same meanings as defined above, with a compound represented by the formula (VIII):

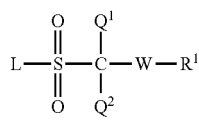

(VIII)

wherein $R^1$, W, $Q^1$ and $Q^2$ are the same meanings as defined above, and L represents a halogen atom, in the presence of a base.

DESCRIPTION OF PREFERRED EMBODIMENTS

In the oxime compound represented by the formula (I) (hereinafter, simply referred to as oxime (I)), Y represents an unsubstituted or substituted n-valent C6-C14 aromatic hydrocarbon group, and n represents an integer of 1 to 6, and n is preferably 1.

In this specification, a C6-C14 aromatic hydrocarbon group includes a fluorenyl group.

Examples of the unsubstituted n-valent C6-C14 aromatic hydrocarbon group include a monovalent C6-C14 aromatic hydrocarbon group such as a phenyl group, a 1-naphthyl group, a 2-naphthyl group, a 1,1'-biphenyl-4-yl group, a 1-fluorenyl group and a 2-fluorenyl group; a divalent $C_6$-$C_{14}$ aromatic hydrocarbon group such as a 1,4-phenylene group, a 1,1'-biphenyl-4,4'-diyl group and a fluorene-2,6-diyl group; a trivalent C6-C14 aromatic hydrocarbon group such as a benzene-1,2,4-triyl group, a naphthalene-2,3,6-triyl group and a fluorene-2,4,6-triyl group; a tetravalent C6-C14 aromatic hydrocarbon group such as a fluorene-2,4,6,8-tetrayl group; and a pentavalent C6-C14 aromatic hydrocarbon group such as a fluorene-2,3,5,6,8-pentayl group.

Examples of the substituent of the n-valent C6-C14 aromatic hydrocarbon group include a halogen atom such as a fluorine atom and a chlorine atom; a C1-C6 alkyl group such as a methyl group, an ethyl group and a tert-butyl group; a C6-C20 aryloxy group such as a phenoxy group; a cyano group; a nitro group; a hydroxyl group; a C1-C20 hydroxyalkyl group such as a hydroxymethyl group; and the following groups:

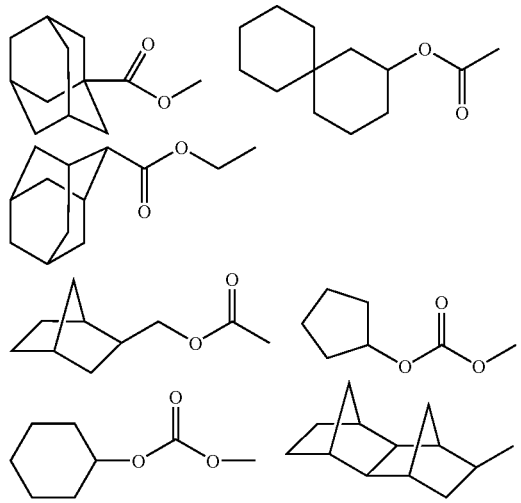

-continued

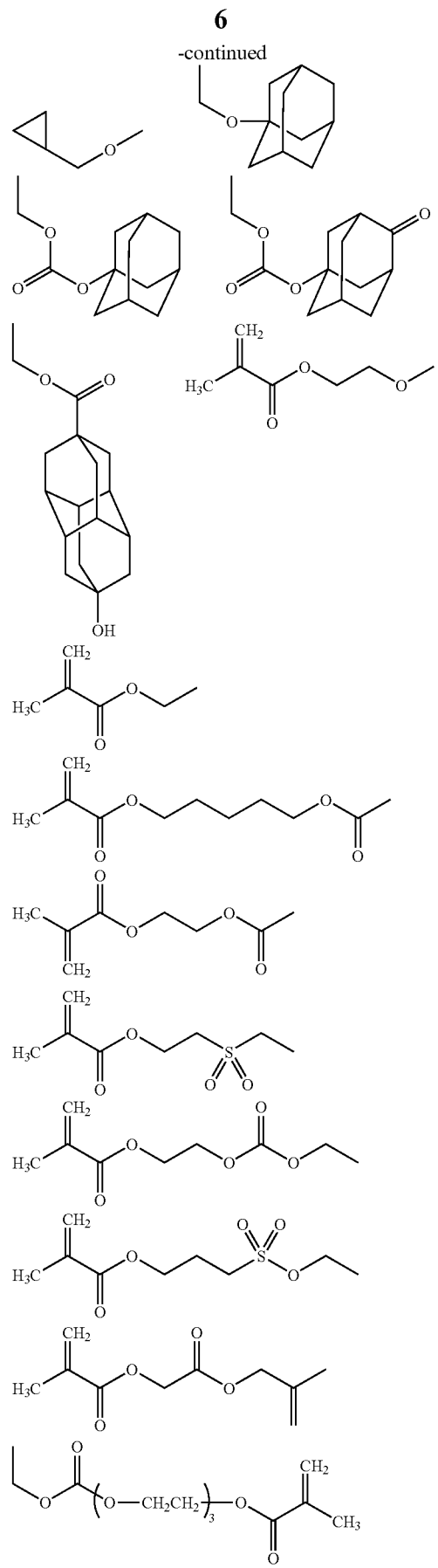

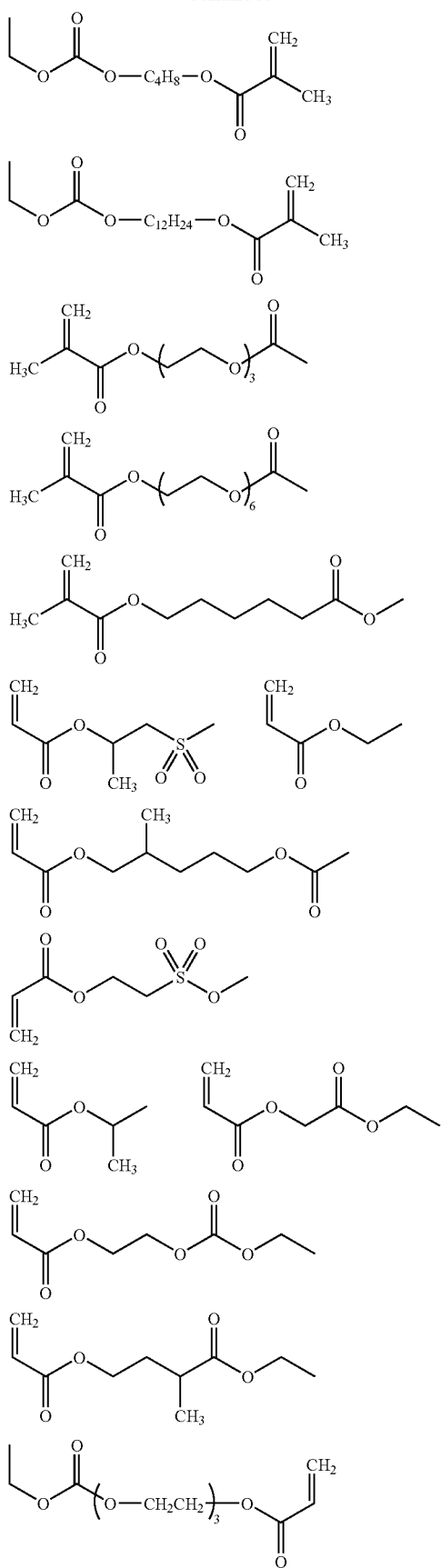

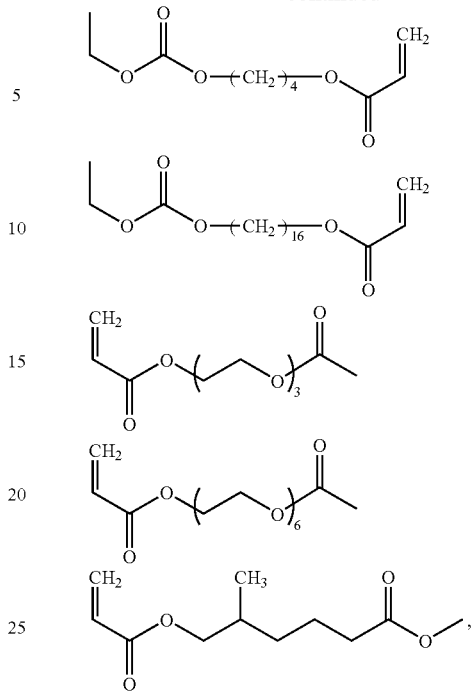

in the formulae above, straight line with an open end shows a bond which is extended from the adjacent n-valent C6-C14 aromatic hydrocarbon group.

A phenyl group, a biphenyl group, a fluorenyl group, a phenylene group, a biphenylene group and a fluorenylene group are preferable, and a phenyl group and a phenylene group are more preferable.

In the formula (I), $R^1$ represents a C1-C30 aliphatic hydrocarbon group, a C6-C14 aromatic hydrocarbon group, a C4-C10 heteroaromatic hydrocarbon group, a C1-C20 alkyl group having a C6-C14 aromatic hydrocarbon group or a C1-C20 alkyl group having a C4-C10 heteroaromatic hydrocarbon group.

Examples of the C1-C30 aliphatic hydrocarbon group include a linear C1-C30 aliphatic hydrocarbon group such as a methyl group, an ethyl group, an n-propyl group, an isopropyl group, an n-butyl group, an n-pentyl group, an n-hexyl group, an n-heptyl group, an n-octyl group, a tert-octyl group, an n-nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, a docosyl group, a tricosyl group, a tetracosyl group, a pentacosyl group, a hexacosyl group, a heptacosyl group, an octacosyl group, a nonacosyl group and a triacontayl group; a branched C1-C30 aliphatic hydrocarbon group such as an isobutyl group, a sec-butyl group, a tert-butyl group, a methylpentyl group, an ethylpentyl group, a methylhexyl group, an ethylhexyl group and a propylhexyl group; a cyclic C3-C30 aliphatic hydrocarbon group such as the following groups represented by the formulae ($R^1$-1) to ($R^1$-16):

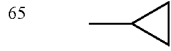

($R^1$-1)

(R¹-2) 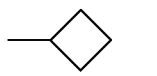
(R¹-3) 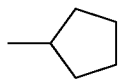
(R¹-4) 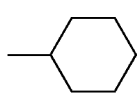
(R¹-5) 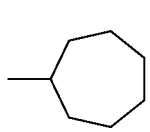
(R¹-6) 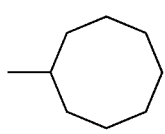
(R¹-7) 
(R¹-8) 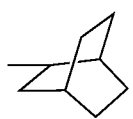
(R¹-9) 
(R¹-10) 
(R¹-11) 
(R¹-12) 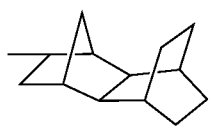
(R¹-13) 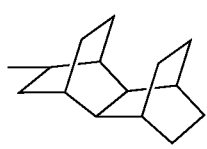
(R¹-14) 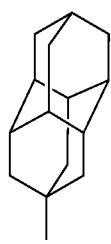
(R¹-15) 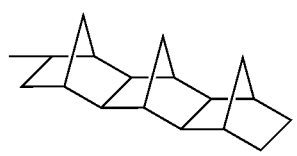
(R¹-16) 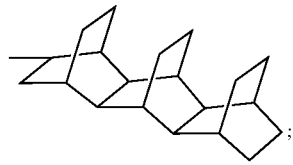
and the following groups represented by the formulae (R¹-17) to (R¹-41):
(R¹-17) 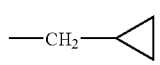
(R¹-18) 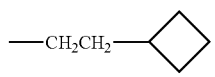
(R¹-19) 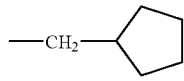
(R¹-20) 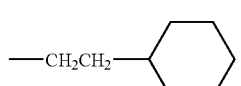
(R¹-21) 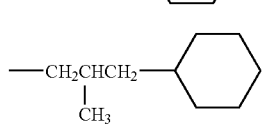
(R¹-22) 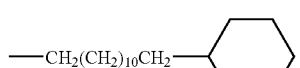
(R¹-23) 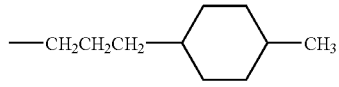
(R¹-24) 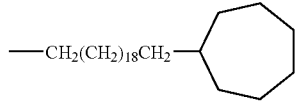
(R¹-25) —CH₂(CH₂)₁₈CH₂— (cycloheptyl)

(R¹-26) 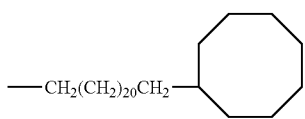

(R¹-27) 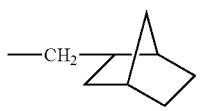

(R¹-28) 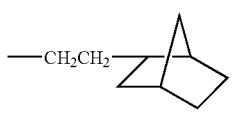

(R¹-29) 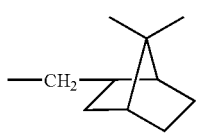

(R¹-30) 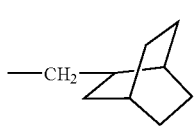

(R¹-31) 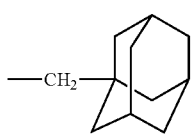

(R¹-32) 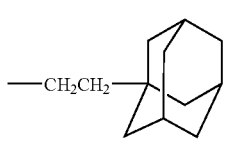

(R¹-33) 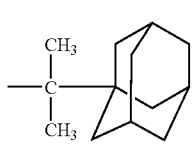

(R¹-34) 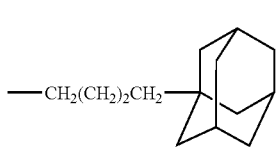

(R¹-35) 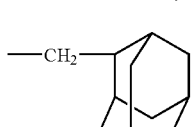

(R¹-36) 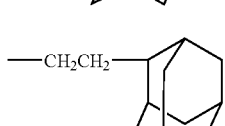

(R¹-37) 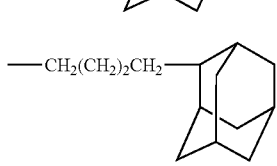

(R¹-38) 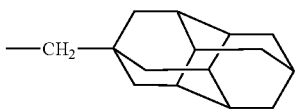

(R¹-39) 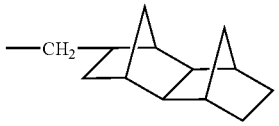

(R¹-40) 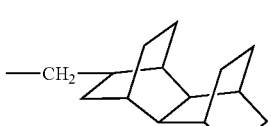

(R¹-41) 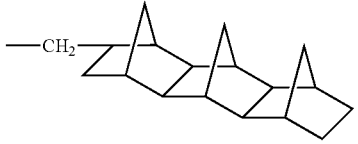

Among them, a C1-C10 linear or branched aliphatic hydrocarbon group and an aliphatic hydrocarbon group having a cyclohexyl group or an adamantyl group are preferable, and a methyl group, an ethyl group, an n-propyl group, an isopropyl group, an n-butyl group, a sec-butyl group, a tert-butyl group, an ethylhexyl group, an adamantyl group, a cyclohexyl group, a cyclohexylmethyl group and an adamantylmethyl group are more preferable.

One or more methylene groups in the above-mentioned aliphatic hydrocarbon groups may be replaced by —O—, —S—, —CO—, —CO—O—, —SO₂— or —N(Rᶜ)— wherein Rᶜ represents a hydrogen atom or a linear or branched chain C1-C4 aliphatic hydrocarbon group. Examples of the linear or branched chain C1-C4 aliphatic hydrocarbon group include a methyl group, an ethyl group, an n-propyl group, an isopropyl group, an n-butyl group, an isobutyl group and a tert-butyl group. Examples of the aliphatic hydrocarbon group in which one or more methylene groups are replaced by —O—, —S—, —CO—, —CO—O—, —SO₂— or —N(Rᶜ)— include the following groups represented by the formulae (R¹-42) to (R¹-60)

(R¹-42) 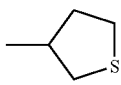

(R¹-43) 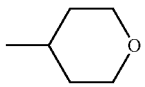

(R¹-44) 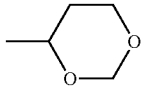

(R¹-45) 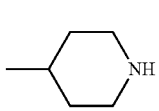

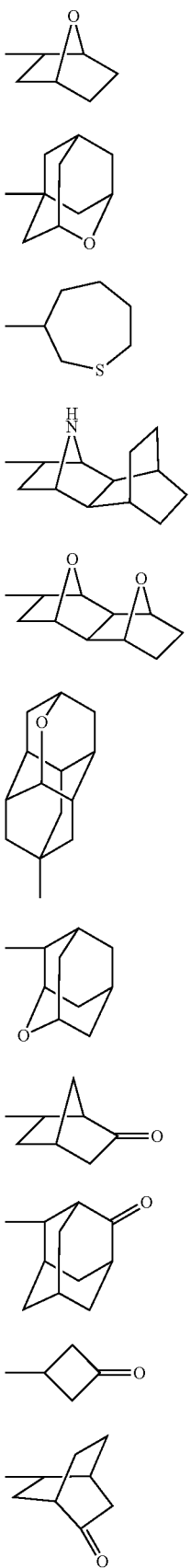

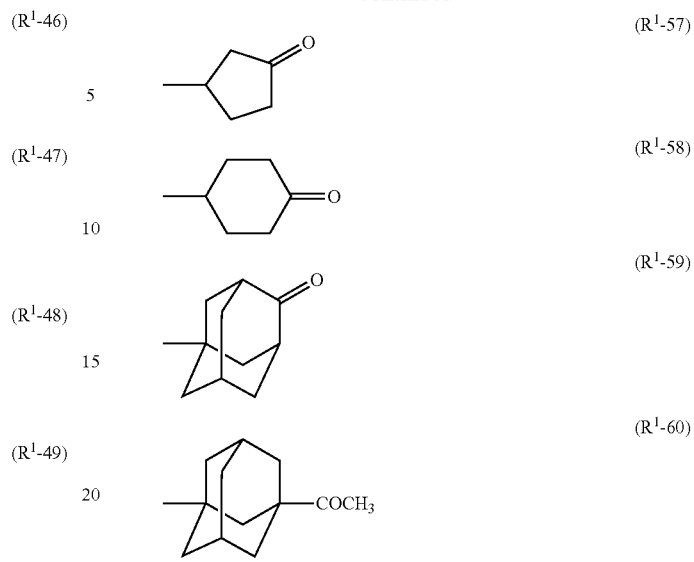

The above-mentioned aliphatic hydrocarbon group may be substituted with at least one selected from the group consisting of a hydroxyl group, an acryloyloxy group, a methacryloyloxy group, a halogen atom, a cyano group, —OR$^2$, —CO—OR$^2$, —O—CO—OR$^2$, —O—CO—R$^2$, —SO$_2$—OR$^2$, —O—SO$_2$—R$^2$ and —SO$_2$R$^2$ wherein R$^2$ represents a linear or branched chain C1-C20 aliphatic hydrocarbon group in which one or more methylene groups may be replaced by —O—, —S—, —CO—, —CO—O— or —N(R$^c$)—, and which may be substituted with at least one selected from the group consisting of a hydroxyl group, an acryloyloxy group and a methacryloyloxy group.

Examples of the aliphatic hydrocarbon group substituted with at least one selected from the group consisting of a hydroxyl group, an acryloyloxy group, a methacryloyloxy group, a halogen atom, a cyano group, —OR$^2$, —CO—OR$^2$, —O—CO—OR$^2$, —O—CO—R$^2$, —SO$_2$—OR$^2$, —O—SO$_2$—R$^2$ and —SO$_2$R$^2$ include the following groups represented by the formulae (R$^1$-61) to (R$^1$-182)

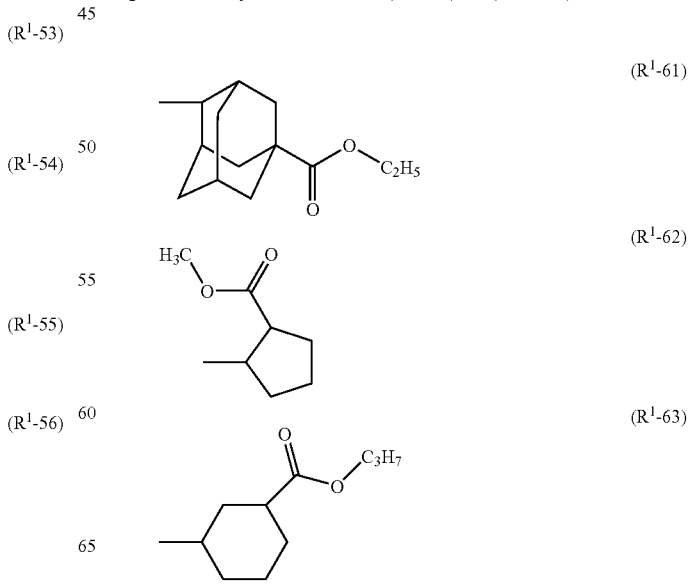

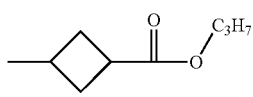 (R¹-64)
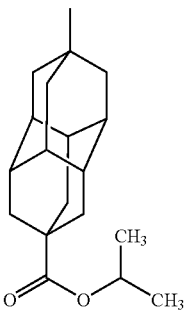 (R¹-65)
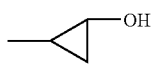 (R¹-66)
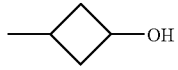 (R¹-67)
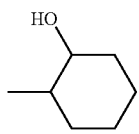 (R¹-68)
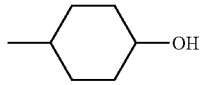 (R¹-69)
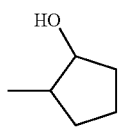 (R¹-70)
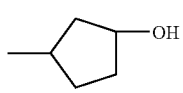 (R¹-71)
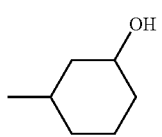 (R¹-72)
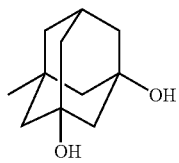 (R¹-73)
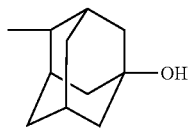 (R¹-74)
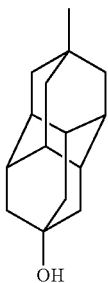 (R¹-75)
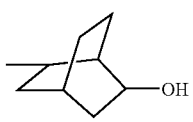 (R¹-76)
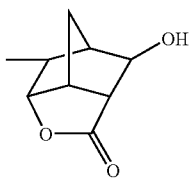 (R¹-77)
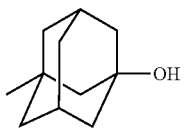 (R¹-78)
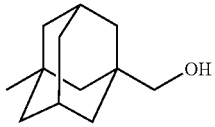 (R¹-79)
 (R¹-80)
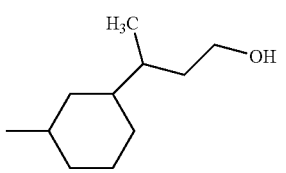 (R¹-81)
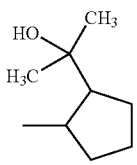 (R¹-82)
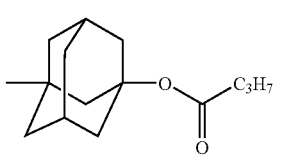 (R¹-83)

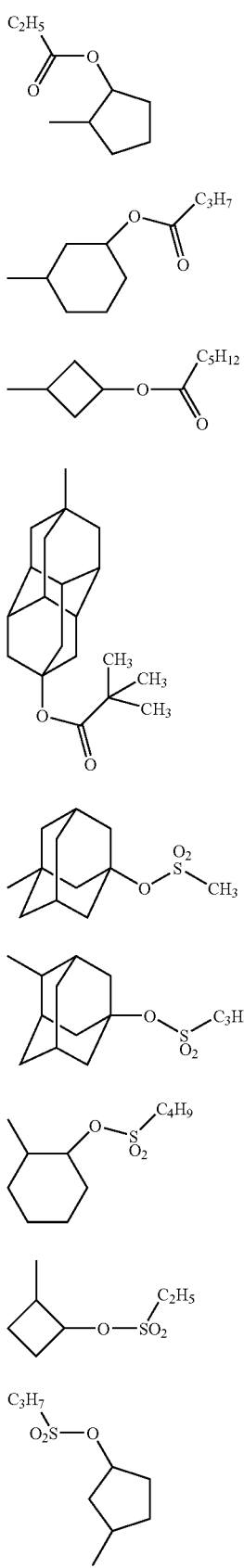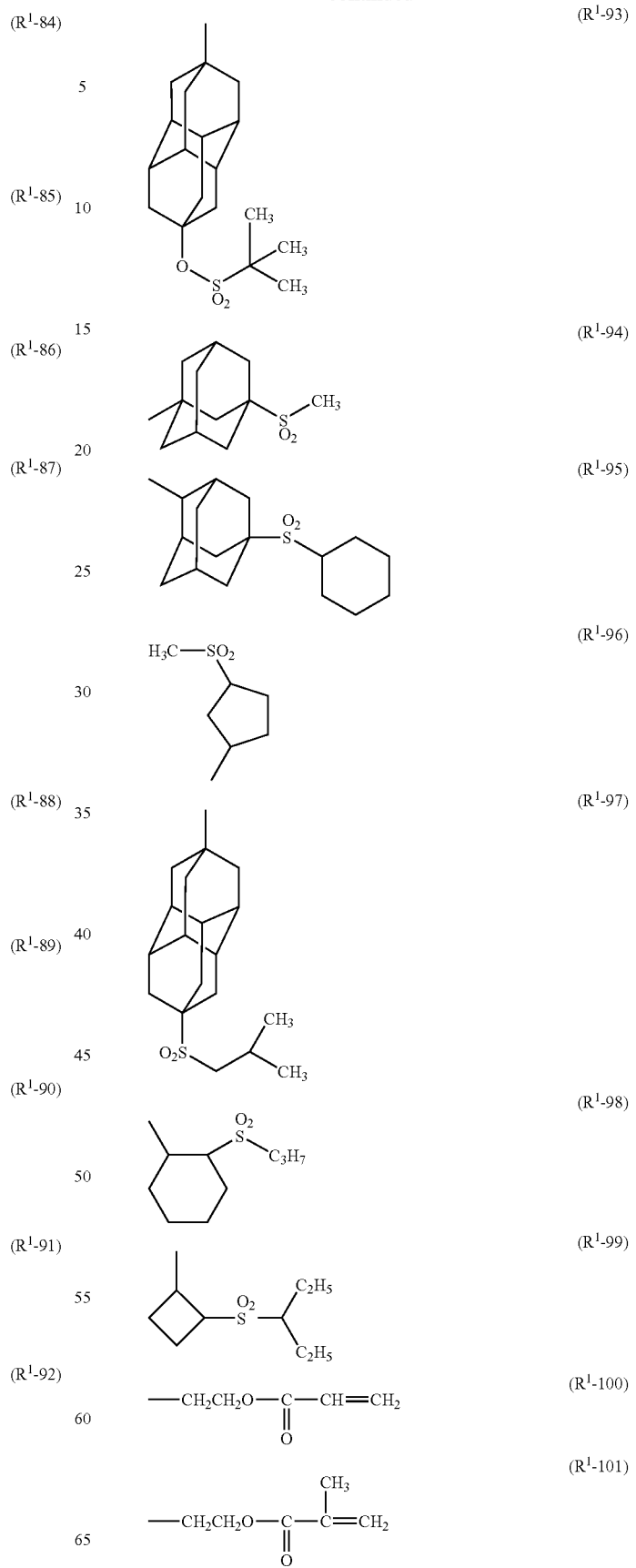

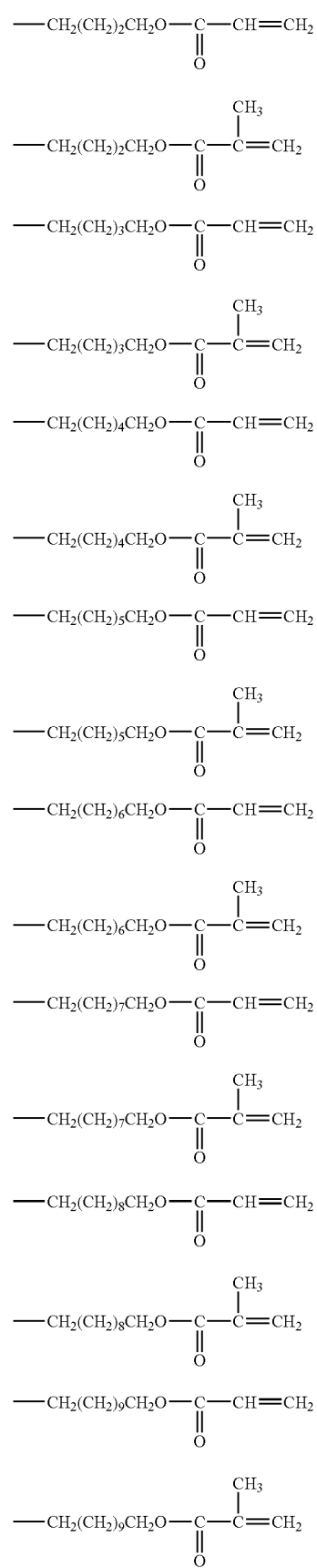
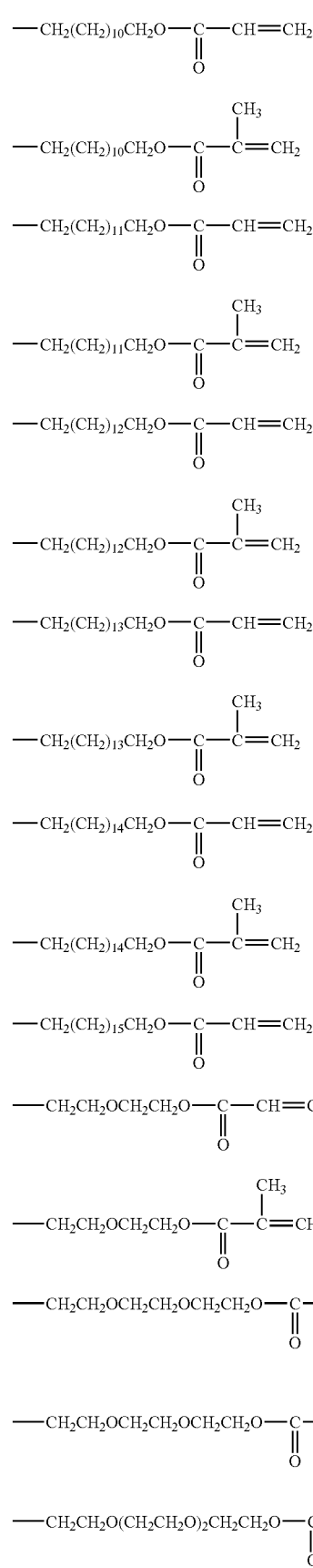

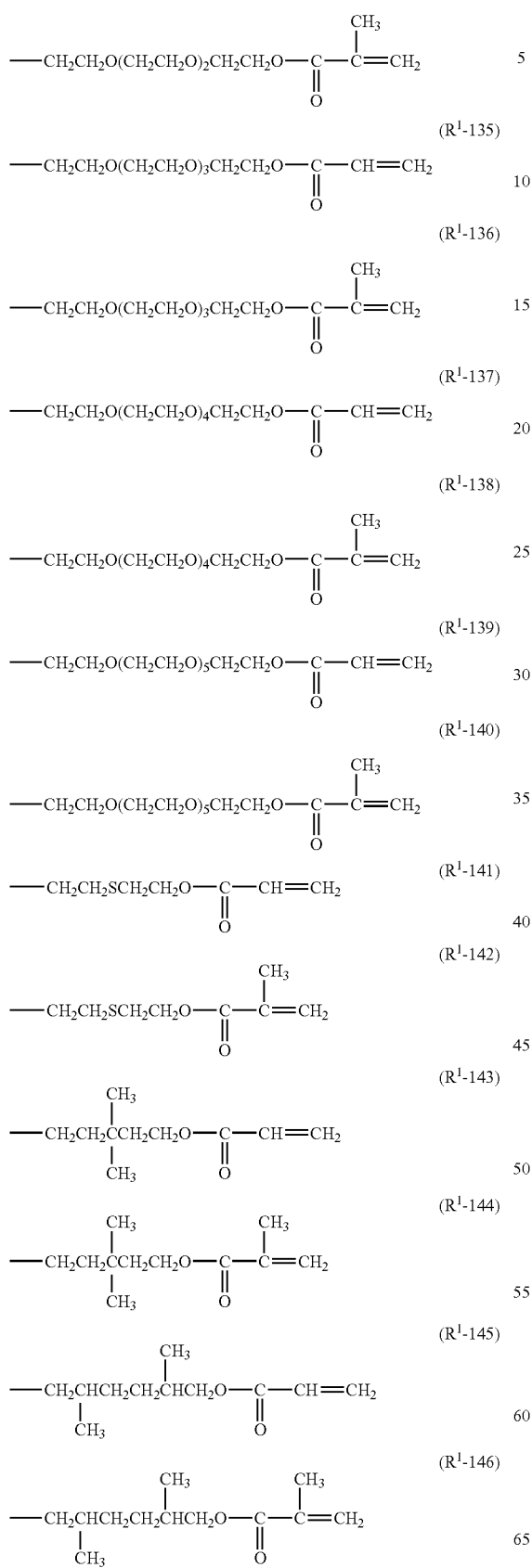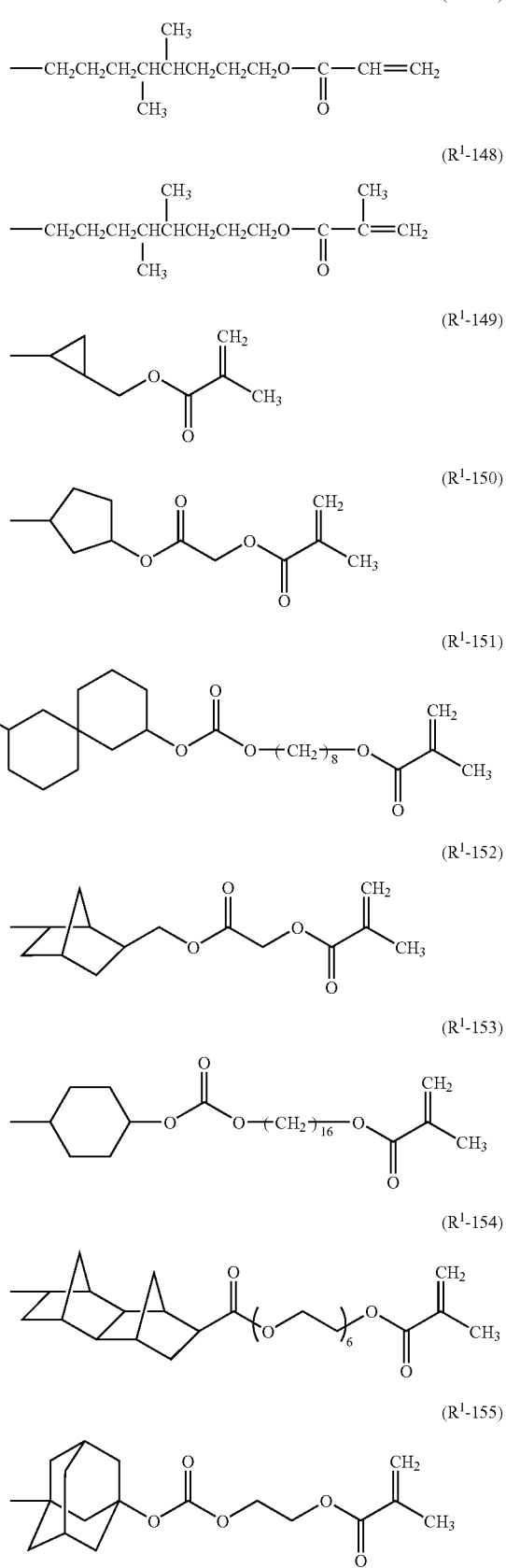

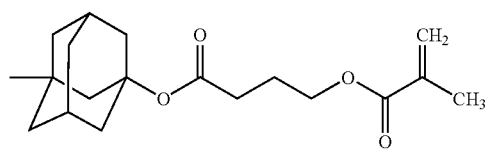
(R¹-156)
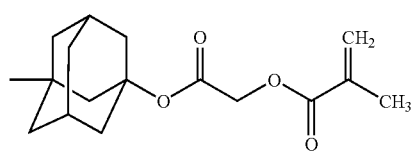
(R¹-157)
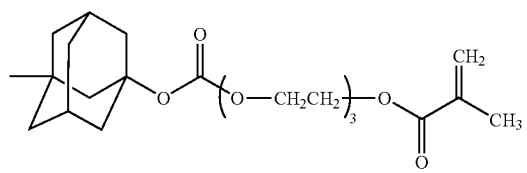
(R¹-158)
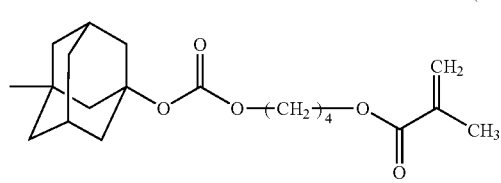
(R¹-159)
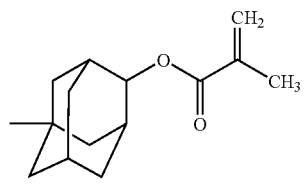
(R¹-160)
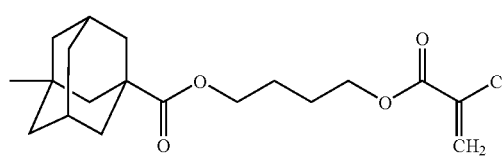
(R¹-161)
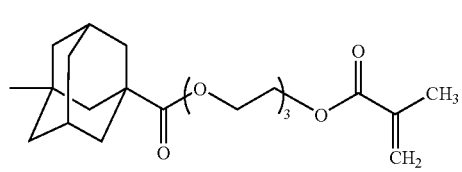
(R¹-162)
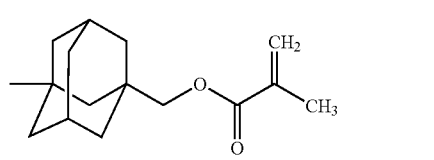
(R¹-163)
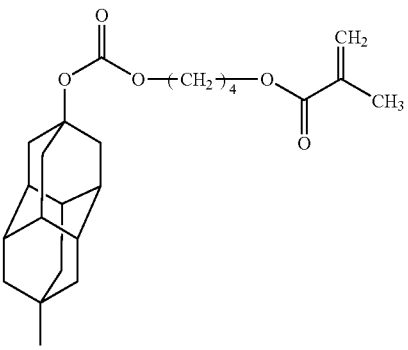
(R¹-164)
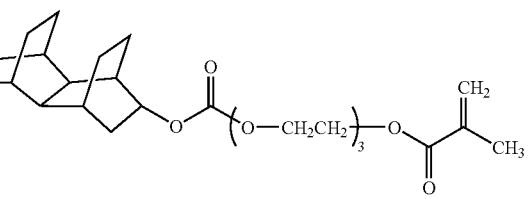
(R¹-165)
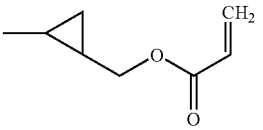
(R¹-166)
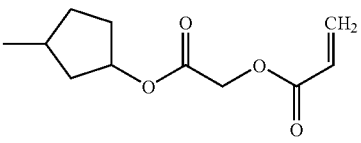
(R¹-167)
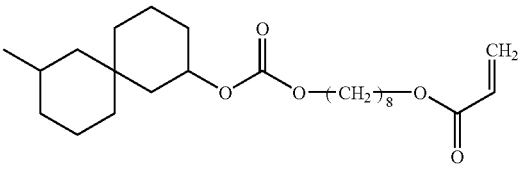
(R¹-168)
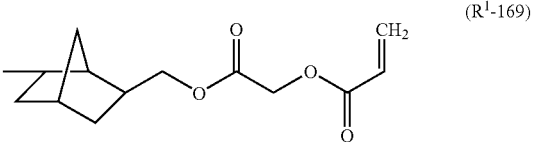
(R¹-169)
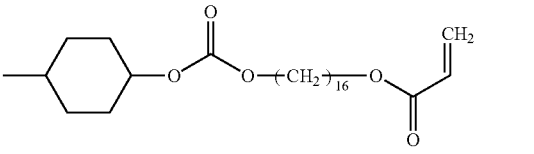
(R¹-170)
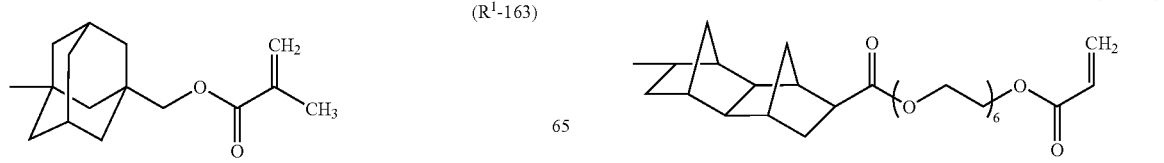
(R¹-171)

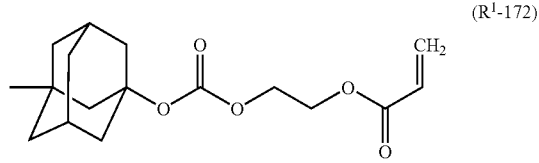
(R¹-172)

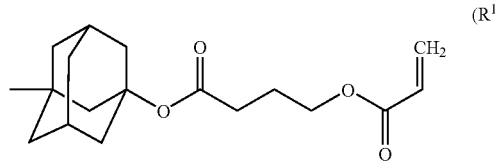
(R¹-173)

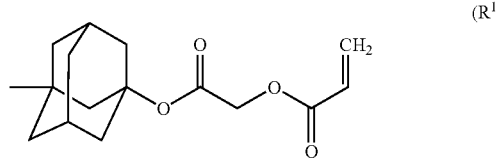
(R¹-174)

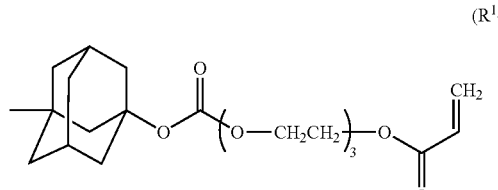
(R¹-175)

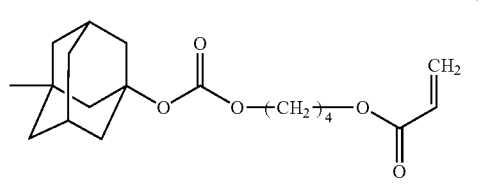
(R¹-176)

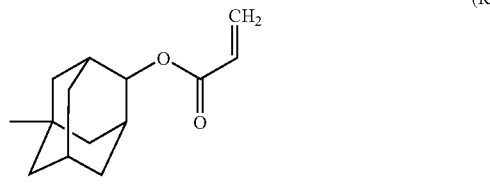
(R¹-177)

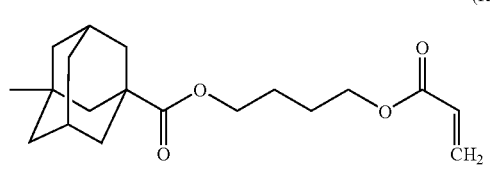
(R¹-178)

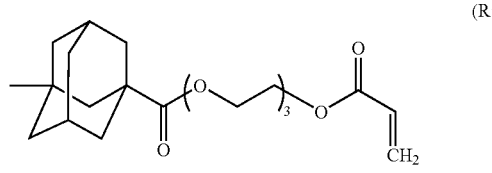
(R¹-179)

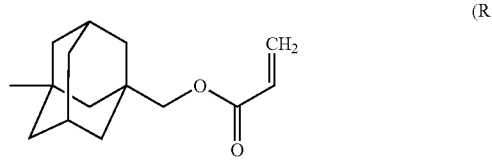
(R¹-180)

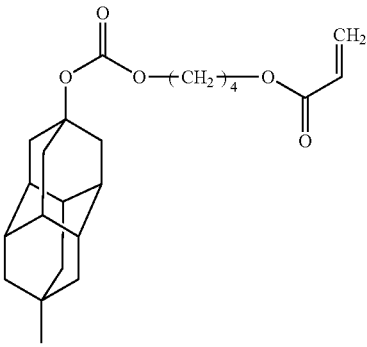
(R¹-181)

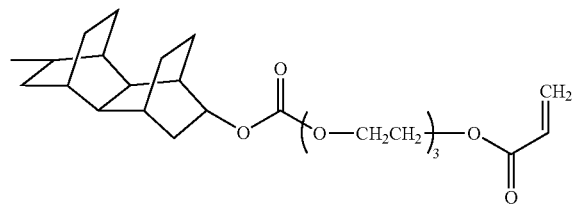
(R¹-182)

The acryloyloxy group and a methacryloyloxy group are preferably bonded to a terminal of the aliphatic hydrocarbon group, respectively.

Examples of the C6-C14 aromatic hydrocarbon group include a phenyl group, a 2,4-dimethylphenyl group, 4-tert-butylphenyl group, a 4-methylphenyl group, a 1-naphthyl group and a 2-naphthyl group. The aromatic hydrocarbon group may be substituted with at least one selected from the group consisting of a hydroxyl group, an acryloyloxy group, a methacryloyloxy group, a halogen atom, a cyano group, —OR², —CO—OR², —O—CO—OR², —O—CO—R², —SO₂—OR², —O—SO₂—R² and —SO₂R². Examples thereof include the following groups represented by the formulae (R¹-183) to (R¹-189)

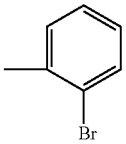
(R¹-183)

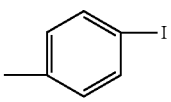
(R¹-184)

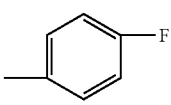
(R¹-185)

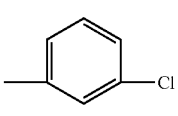
(R¹-186)

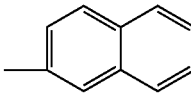
(R¹-187)

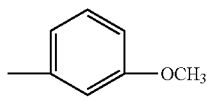 (R¹-188)

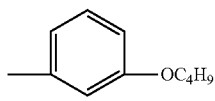 (R¹-189)

Examples of the C4-C10 heteroaromatic hydrocarbon group which may be respectively substituted with at least one selected from the group consisting of a hydroxyl group, an acryloyloxy group, a methacryloyloxy group, a halogen atom, a cyano group, —OR², —CO—OR², —O—CO—OR², —O—CO—R², —SO₂—OR², —O—SO₂—R² and —SO₂R² include the following groups represented by the formulae (R¹-190) to (R¹-195):

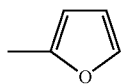 (R¹-190)

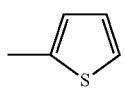 (R¹-191)

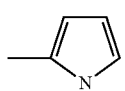 (R¹-192)

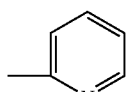 (R¹-193)

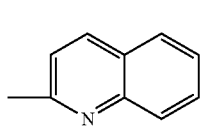 (R¹-194)

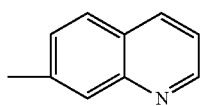 (R¹-195)

Examples of the C1-C20 alkyl group having a C6-C14 aromatic hydrocarbon group which may be respectively substituted with at least one selected from the group consisting of a hydroxyl group, an acryloyloxy group, a methacryloyloxy group, a halogen atom, a cyano group, —OR², —CO—OR², —O—CO—OR², —O—CO—R², —SO₂—OR², —O—SO₂—R² and —SO₂R² include the following groups represented by the formulae (R¹-196) to (R¹-213)

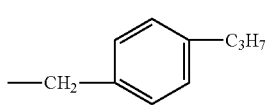 (R¹-196)

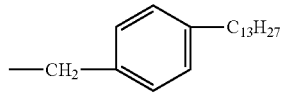 (R¹-197)

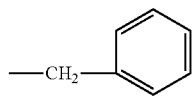 (R¹-198)

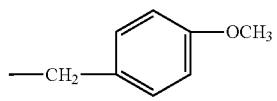 (R¹-199)

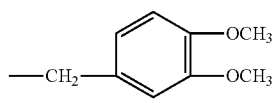 (R¹-200)

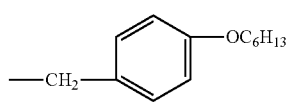 (R¹-201)

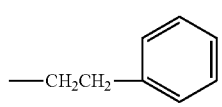 (R¹-202)

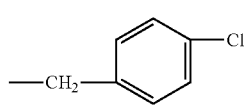 (R¹-203)

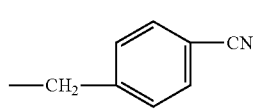 (R¹-204)

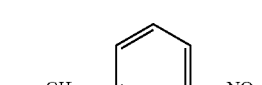 (R¹-205)

 (R¹-206)

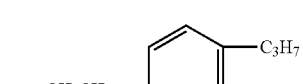 (R¹-207)

 (R¹-208)

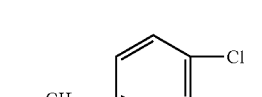 (R¹-209)

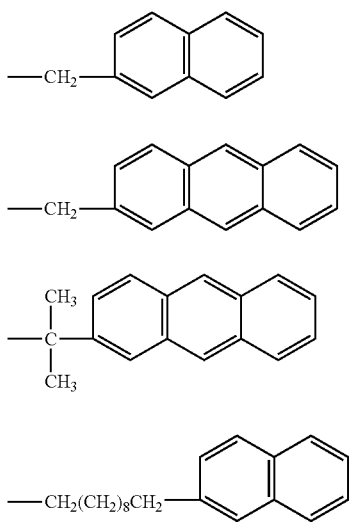

(R¹-210)

(R¹-211)

(R¹-212)

(R¹-213)

Examples of the C1-C20 alkyl group having a C4-C10 heteroaromatic hydrocarbon group which may be respectively substituted with at least one selected from the group consisting of a hydroxyl group, an acryloyloxy group, a methacryloyloxy group, a halogen atom, a cyano group, —OR², —CO—OR², —O—CO—OR²—O—CO—R², —SO₂—OR², —O—SO₂—R² and —SO₂R² include the following groups represented by the formulae (R¹-214) to (R¹-221)

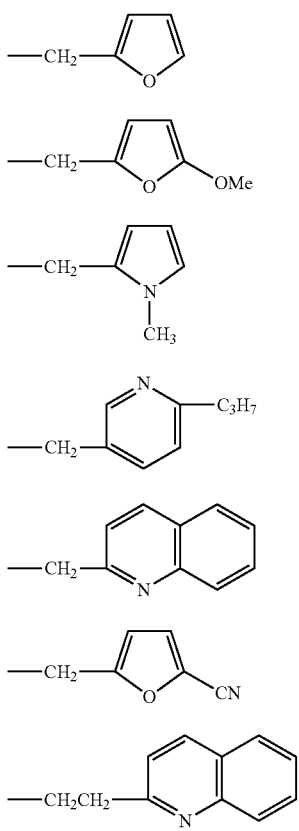

(R¹-214)

(R¹-215)

(R¹-216)

(R¹-217)

(R¹-218)

(R¹-219)

(R¹-220)

(R¹-221)

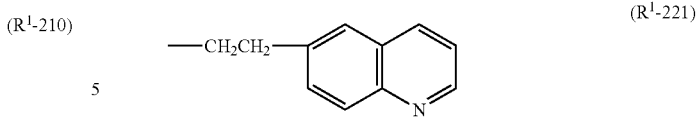

R¹ is preferably a C1-C30 aliphatic hydrocarbon group in which one or more methylene groups may be replaced by —O—, —S— or —N(Rᶜ)—, and which may be substituted with at least one selected from the group consisting of a hydroxyl group and a halogen atom.

R¹ is more preferably a C1-C30 aliphatic hydrocarbon group in which one or more methylene groups are replaced by —CO— or a C1-C30 aliphatic hydrocarbon group having an acryloyloxy group or a methacryloyloxy group, and one or more methylene groups in the aliphatic hydrocarbon group may be replaced by —O—, —S—, —N(Rᶜ)—, —CO— or —CO—O—.

In the formula (I), W represents —CO—O—, —CH₂O— or —CH₂O—CO—, and W is preferably —CO—O—.

Q¹ and Q² each independently represent a fluorine atom or a C1-C6 perfluoroalkyl group. Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. Q¹ and Q² each independently preferably represent a fluorine atom or a trifluoromethyl group, and Q¹ and Q² are more preferably fluorine atoms.

Z represents a C1-C20 halogenated aliphatic hydrocarbon group, a C6-C14 halogenated aromatic hydrocarbon group, a cyano group, —CX₂—R¹ or —CX₂—SO₂—R¹, and X represents a halogen atom or a C1-C20 halogenated aliphatic hydrocarbon group. Examples thereof include a trifluoromethyl group, a pentafluoroethyl group, a heptafluoropropyl group, and the followings:

—CF₂H—CF₂—CF₂H—CF₂—CF₂—CF₂H

—CF₂—CF₂—CF₂—CF₂H

Examples of —CX₂—R¹ include the followings:

—CF₂—CH₃—CF₂—CH₂—CH₃

—CF₂—CH₂—CH₂—CH₃

Examples of —CX₂—SO₂—R¹ include the followings:

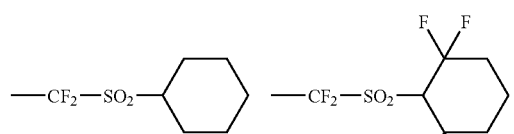

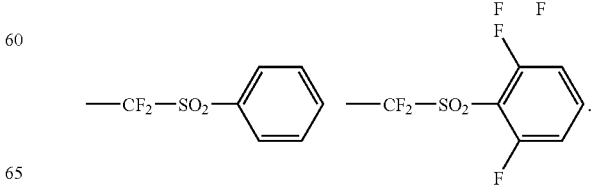

Z is preferably a C1-C20 fluorinated aliphatic hydrocarbon group or a cyano group.
Examples of the group represented by the following formula (Y):
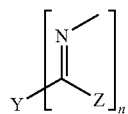
(Y)
include the following groups represented by the formulae (Y-1) to (Y-87):
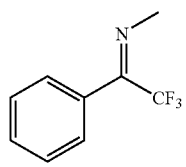
(Y-1)
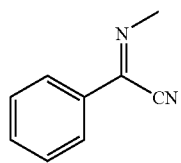
(Y-2)
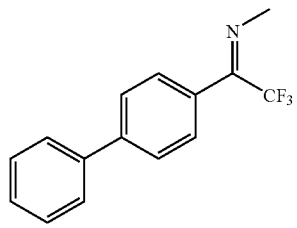
(Y-3)
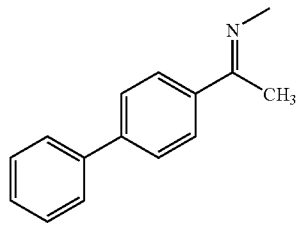
(Y-4)
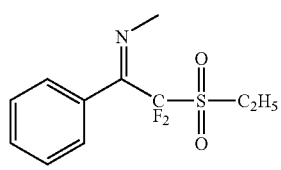
(Y-5)
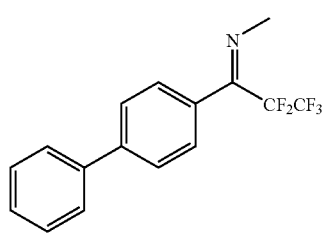
(Y-6)
-continued
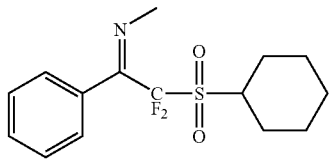
(Y-7)
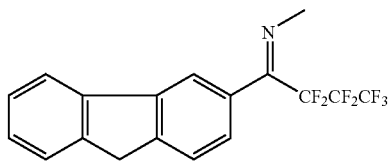
(Y-8)
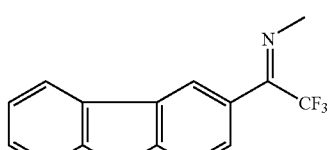
(Y-9)
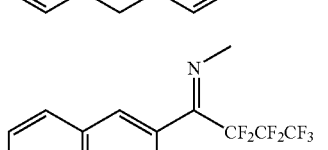
(Y-10)
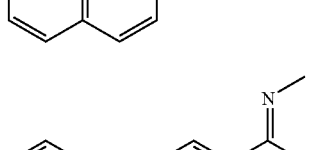
(Y-11)
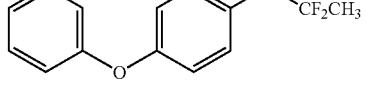
(Y-12)
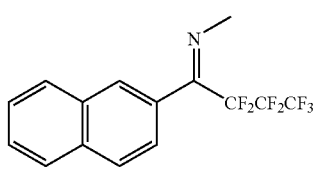
(Y-13)
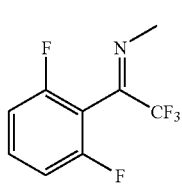
(Y-14)
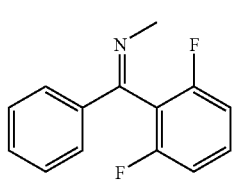
(Y-15)
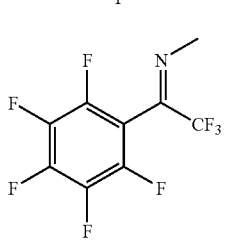

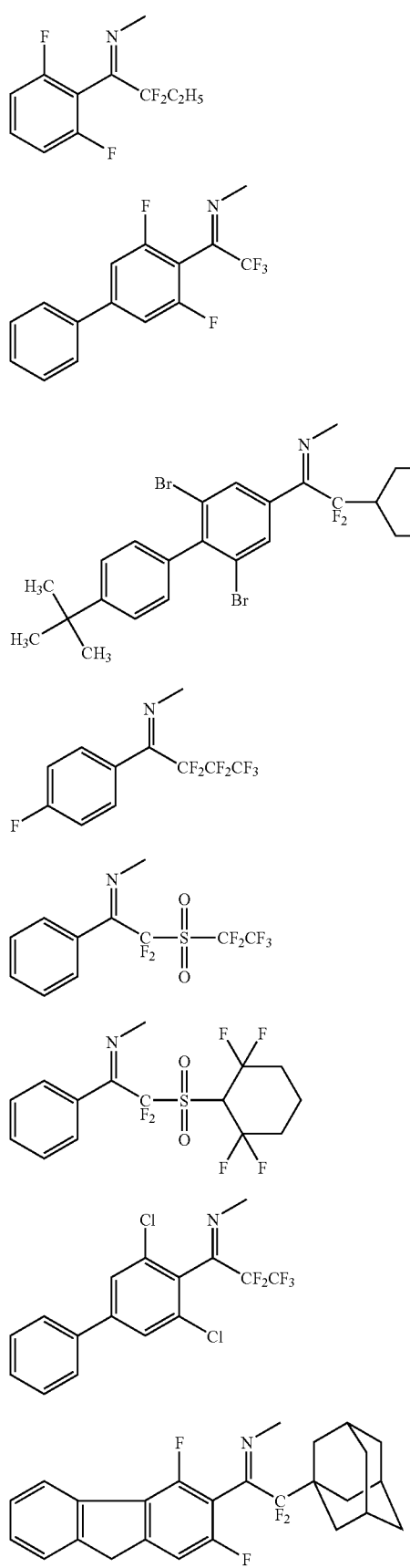
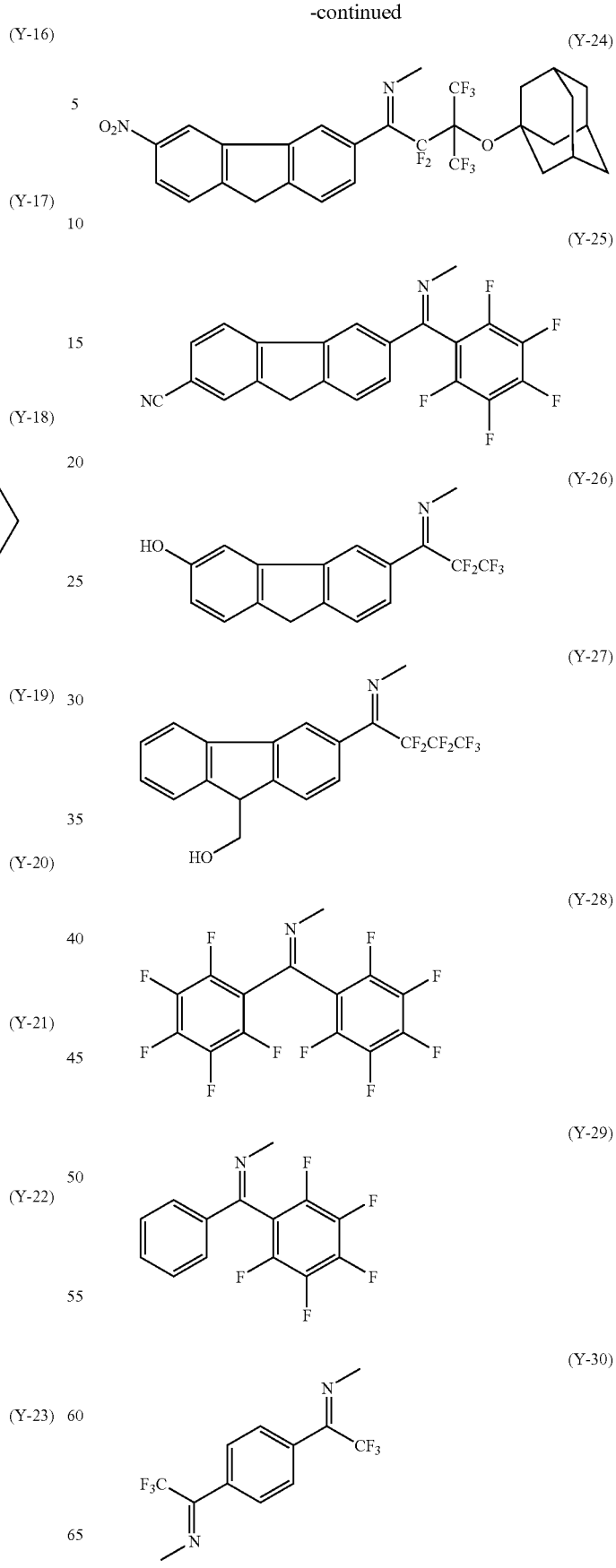

(Y-31) 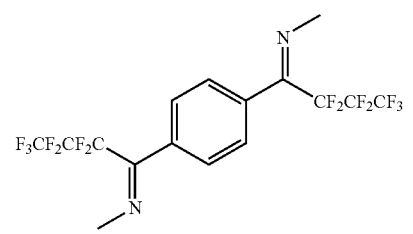
(Y-32) 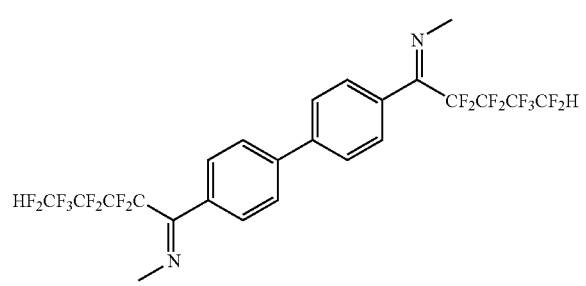
(Y-33) 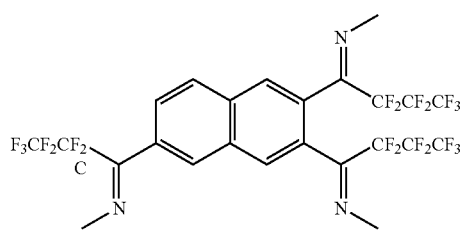
(Y-34) 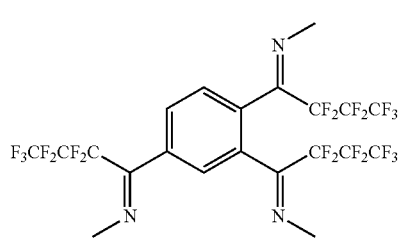
(Y-35) 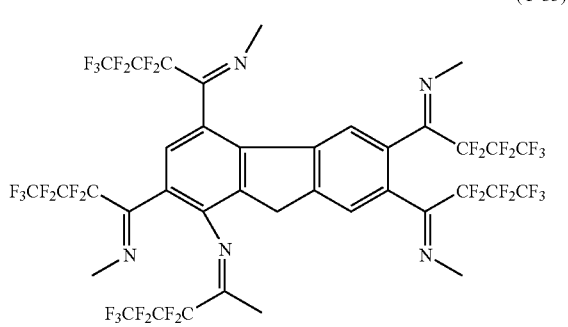
(Y-36) 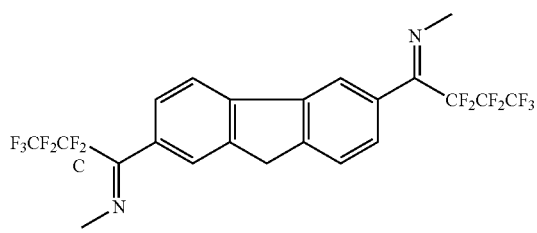
(Y-37) 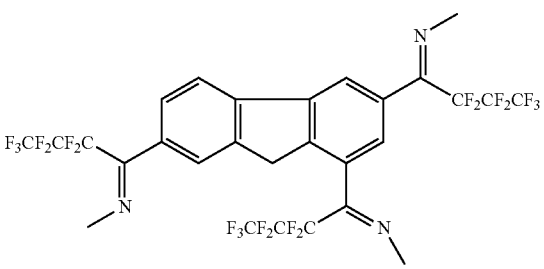
(Y-38) 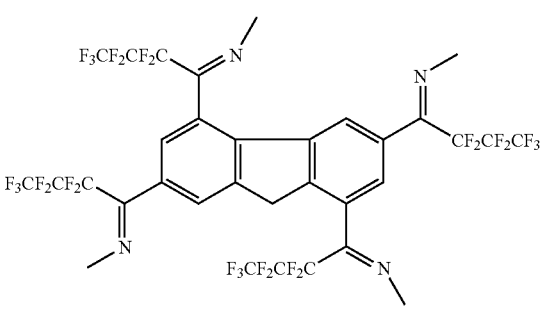
(Y-39) 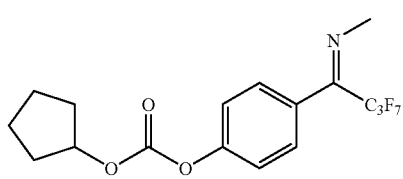
(Y-40) 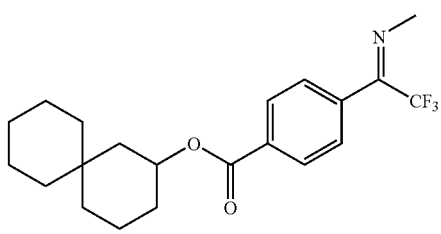
(Y-41) 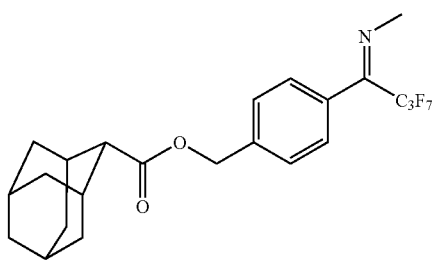
(Y-42) 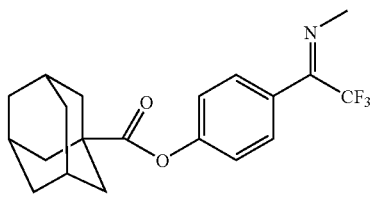

(Y-43) 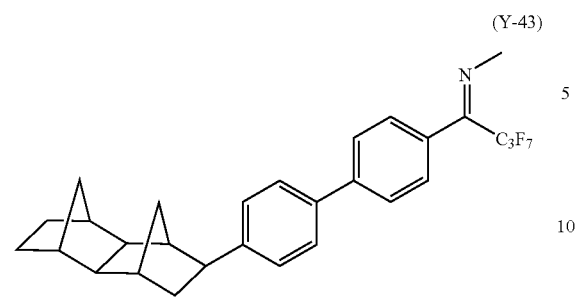
(Y-44) 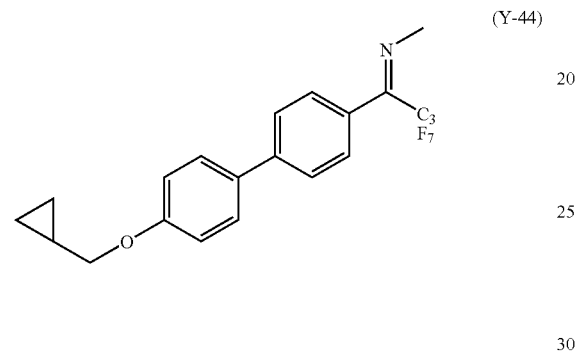
(Y-45) 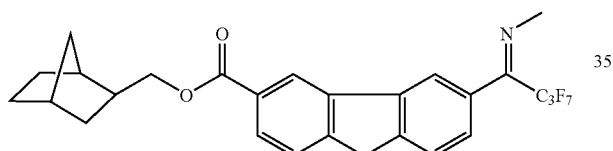
(Y-46) 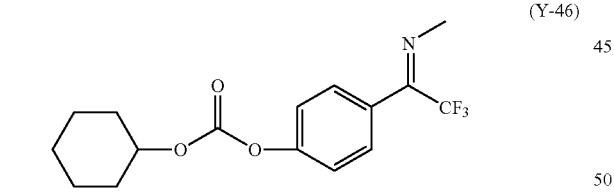
(Y-47) 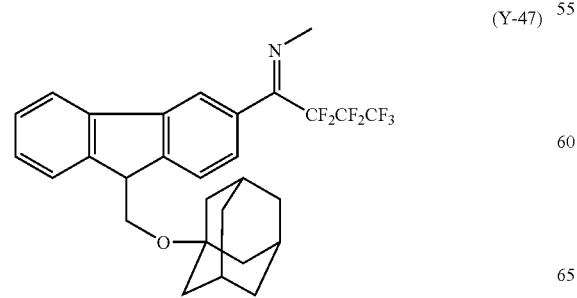
(Y-48) 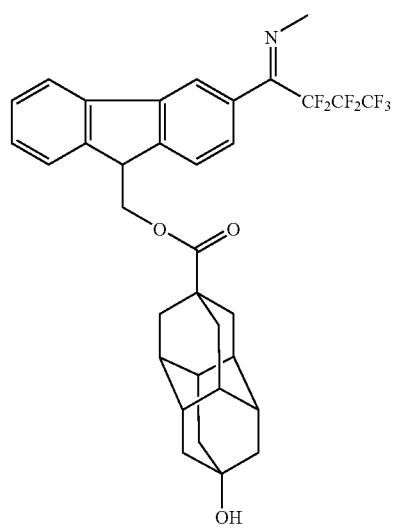
(Y-49) 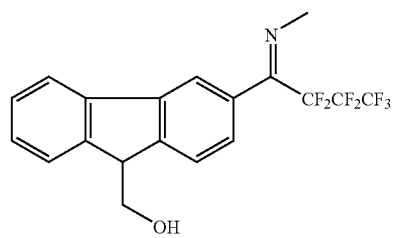
(Y-50) 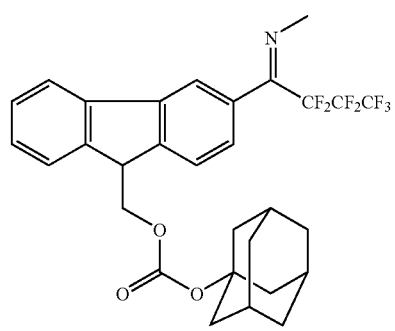
(Y-51) 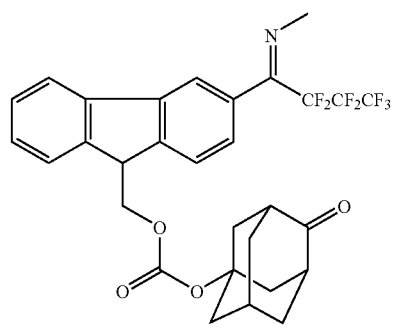
(Y-52) 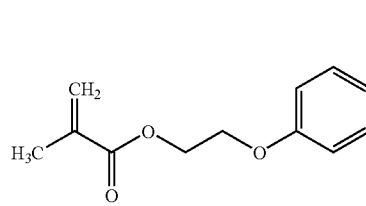

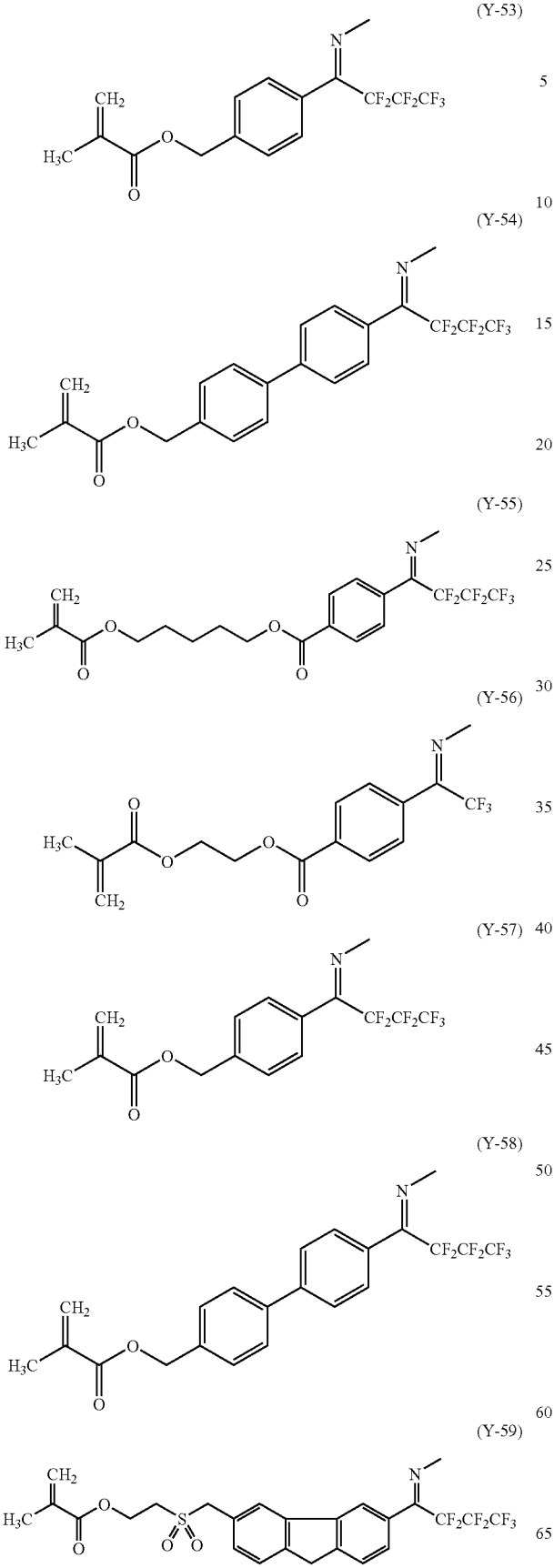
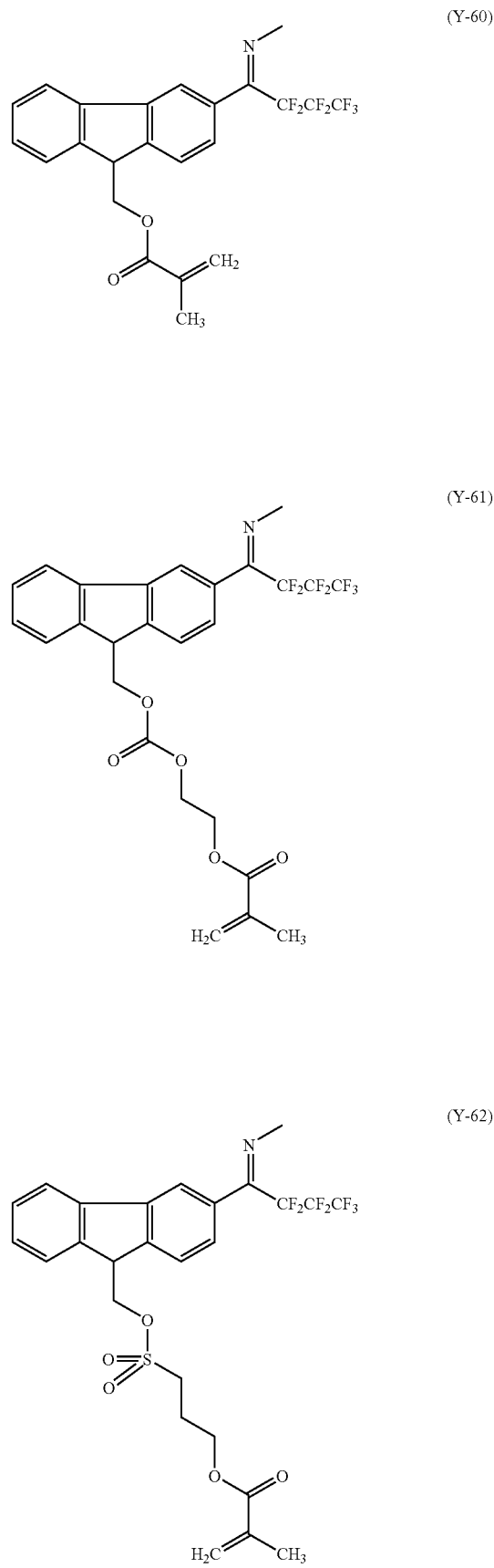

(Y-63)
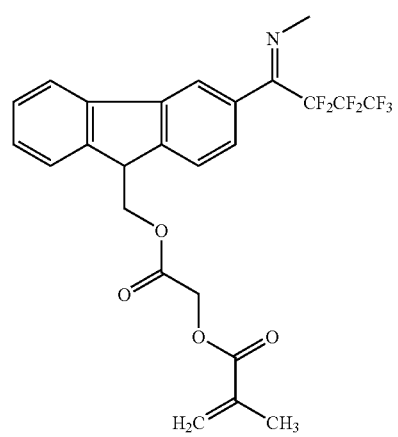
(Y-64)
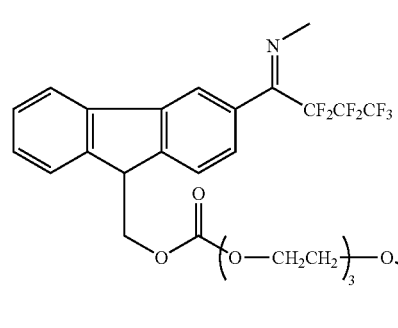
(Y-65)
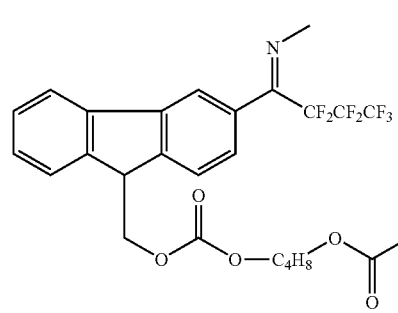
(Y-66)
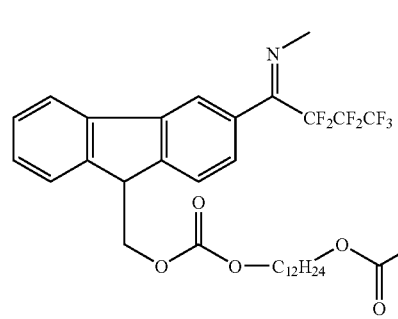
(Y-67)
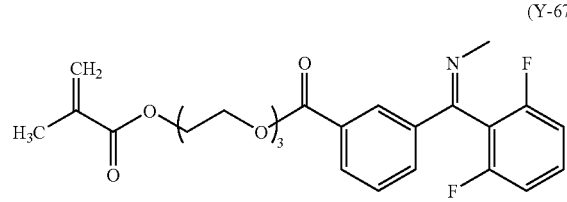
(Y-68)
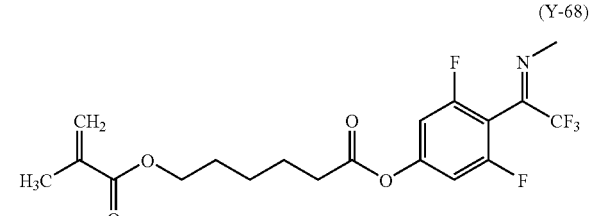
(Y-69)
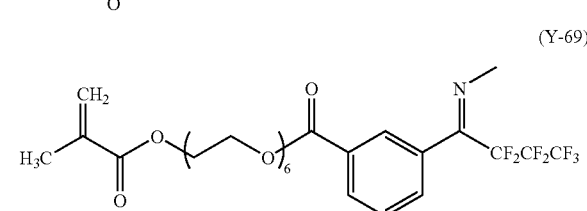
(Y-70)
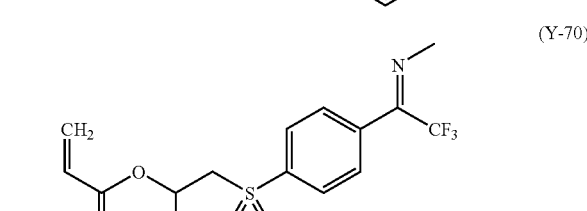
(Y-71)
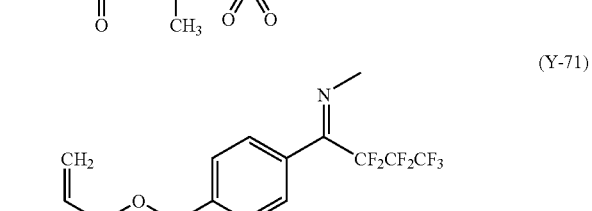
(Y-72)
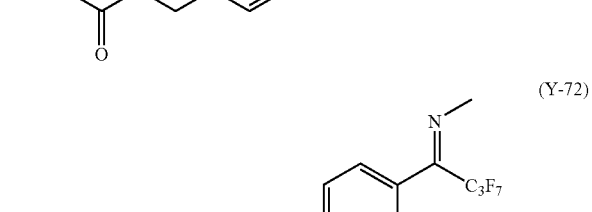
(Y-73)
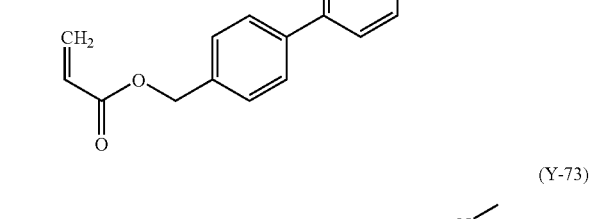
(Y-74)
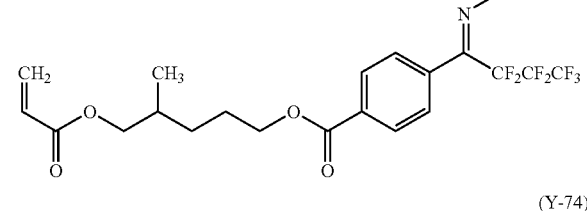

(Y-75)
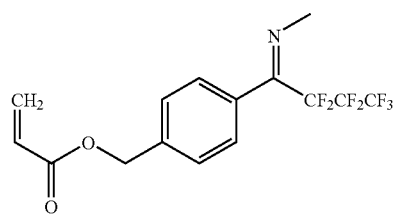
(Y-76)
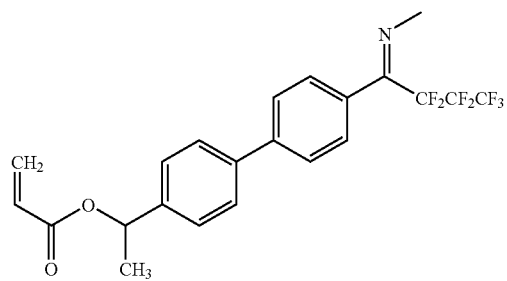
(Y-77)
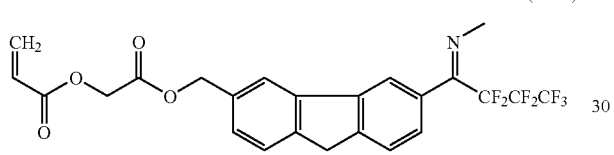
(Y-78)
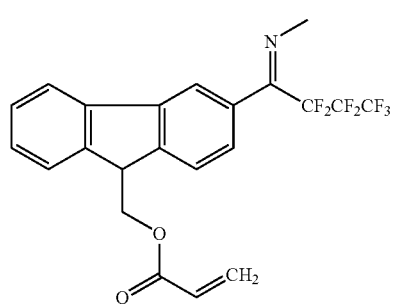
(Y-79)
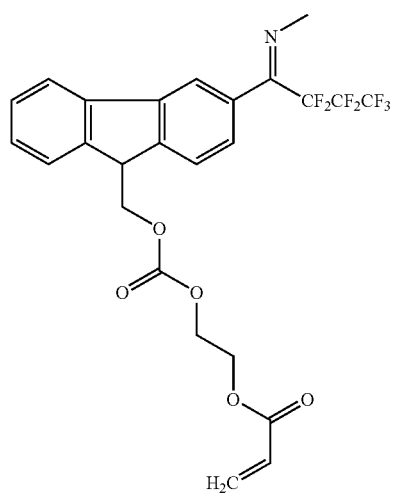
(Y-80)
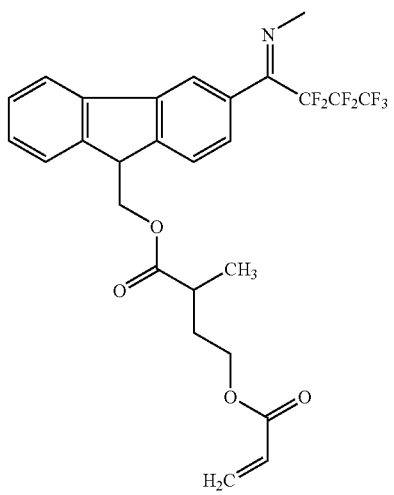
(Y-81)
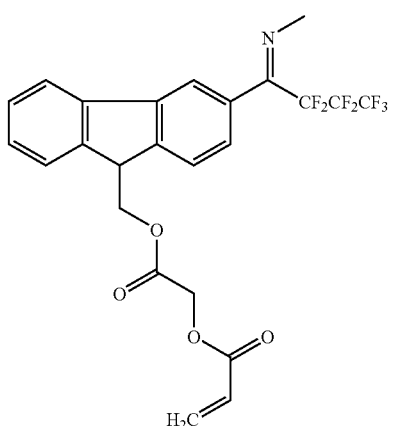
(Y-82)
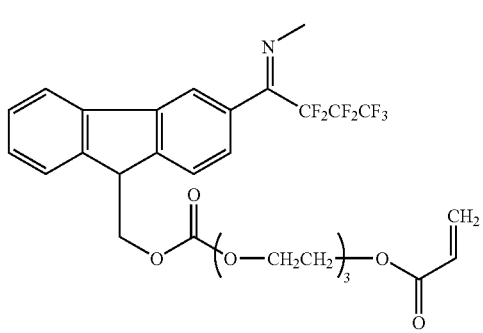
(Y-83)
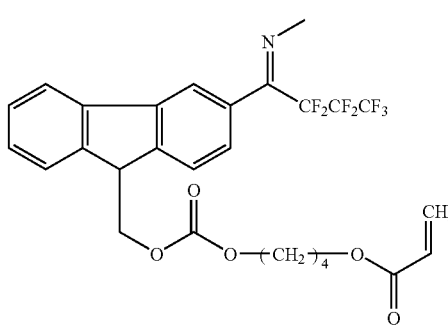

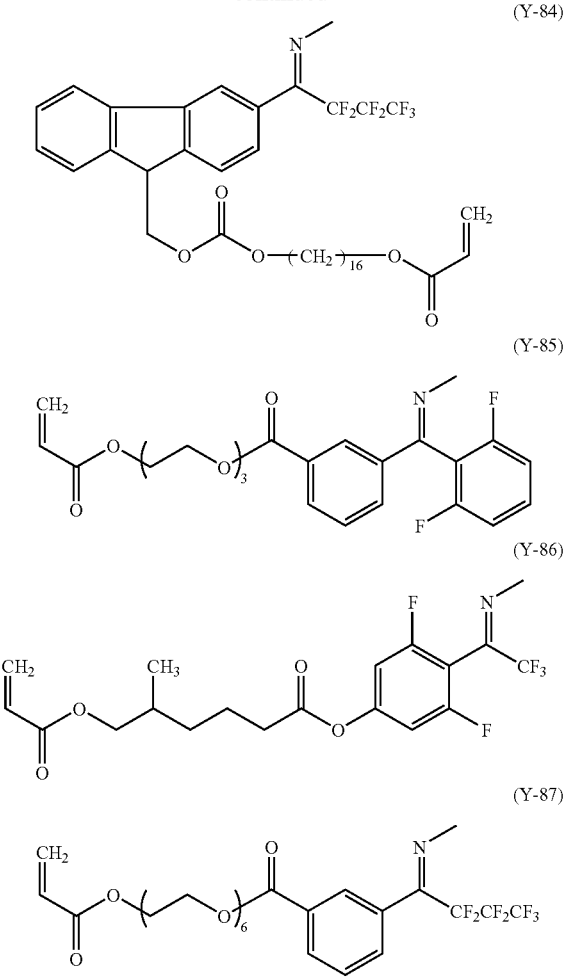

Examples of oxime (I) include an oxime compound represented by the formula (I) wherein the group represented by the following formula (Y) is any one of the groups represented by the formulae (Y-1) to (Y-87), $Q^1$ and $Q^2$ are fluorine atoms, W is —CO—O—, and $R^1$ is a methyl group, an ethyl group, an n-propyl group, an isopropyl group, an n-butyl group, a sec-butyl group, a tert-butyl group, an ethylhexyl group, an adamantyl group, a cyclohexyl group, a cyclohexylmethyl group, an adamantylmethyl group or any one of the groups represented by the formulae ($R^1$-1) to ($R^1$-221).

As oxime (I), an oxime compound represented by the formula (III):

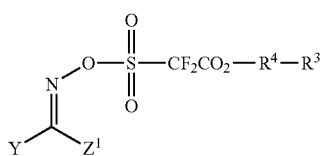

wherein $Y^1$ represents a phenyl group which may be substituted with a C1-C20 aliphatic hydrocarbon group having an acryloyloxy group or a methacryloyloxy group, a naphthyl group which may be substituted with a C1-C20 aliphatic hydrocarbon group having an acryloyloxy group or an methacryloyloxy group, a biphenyl group which may be substituted with a C1-C20 aliphatic hydrocarbon group having an acryloyloxy group or a methacryloyloxy group, an anthryl group which may be substituted with a C1-C20 aliphatic hydrocarbon group having an acryloyloxy group or a methacryloyloxy group, a fluorenyl group which may be substituted with a C1-C20 aliphatic hydrocarbon group having an acryloyloxy group or a methacryloyloxy group or a phenanthryl group which may be substituted with a C1-C20 aliphatic hydrocarbon group having an acryloyloxy group or a methacryloyloxy group, and one or more methylene groups in the C1-C20 aliphatic hydrocarbon group may be replaced by —O—, —S—, —N($R^c$)—, —CO— or —CO—O—, $R^c$ is the same meanings as defined above, $Z^1$ represents a C1-C20 halogenated aliphatic hydrocarbon group or a C6-C14 halogenated aromatic hydrocarbon group, $R^3$ represents a C3-C30 monocyclic or polycyclic aliphatic hydrocarbon group in which one or more methylene groups may be replaced by —O— or —CO—, and which may be substituted with a hydroxyl group, $R^4$ represents a single bond or a C1-C20 divalent aliphatic hydrocarbon group in which one or more methylene groups may be replaced by —O—, —S— or —N($R^c$)—, is preferable.

An oxime compound represented by the formula (Va):

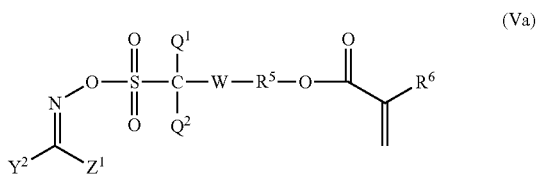

wherein $Y^2$ represents an unsubstituted or substituted phenyl group, an unsubstituted or substituted naphthyl group, an unsubstituted or substituted biphenyl group, an unsubstituted or substituted anthryl group, an unsubstituted or substituted fluorenyl group or an unsubstituted or substituted phenanthryl group, $Z^1$ represents a C1-C20 halogenated aliphatic hydrocarbon group or a C6-C14 halogenated aromatic hydrocarbon group, $R^5$ represents a C1-C30 divalent aliphatic hydrocarbon group in which one or more methylene groups may be replaced by —O—, —S— or —N($R^c$)—, $R^c$ is the same meanings as defined above, $R^6$ represents a hydrogen atom or a methyl group, W represents —CO—O—, —$CH_2$O— or —$CH_2$O—CO—, and $Q^1$ and $Q^2$ are the same meanings as defined above, is also preferable, and an oxime compound represented by the formula (Va) wherein $Q^1$ and $Q^2$ are fluorine atoms and W is —CO—O—, is more preferable.

Oxime (I) can be produced by reacting a compound represented by the formula (VII):

wherein Y, Z and n are the same meanings as defined above, with a compound represented by the formula (VIII):

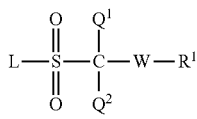
(VIII)

wherein $Q^1$, $Q^2$, W and $R^1$ are the same meanings as defined above and L represents a halogen atom, in an inert solvent such as toluene, tetrahydrofuran, N,N-dimethylformamide, dimethylsulfoxide, acetonitrile, chloroform and dichloromethane, in the presence of a base, at a temperature of about 0 to 150° C., preferably of 0 to 100° C., with stirring.

Examples of the halogen atom represented by L include a fluorine atom, a chlorine atom, a bromine atom and an iodine atom.

The amount of the compound represented by the formula (VIII) is usually 0.9 n to 2 n moles and preferably n to 1.5 n moles per 1 mole of the compound represented by the formula (VII).

Examples of the base include an inorganic base such as sodium hydroxide, potassium hydroxide and potassium carbonate, and an organic base such as pyridine, triethylamine and lutidine. The amount of the base is usually n to 3 n moles and preferably n to 2 n moles per 1 mole of the compound represented by the formula (VII).

Oxime (I) obtained by the process above can be isolated by conducting extraction followed by concentrating, and isolated oxime (I) can be purified by recrystallization or column chromatography.

The compound represented by the formula (VII) can be produced by a reaction of the corresponding ketone compound and hydroxylamine.

The compound represented by the formula (VIII) can be produced by a reaction of a compound represented by the formula (VIIIa):

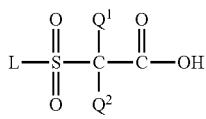
(VIIIa)

wherein L, $Q^1$ and $Q^2$ are the same meanings as defined above, and a compound represented by the formula (VIIIb):

HO—$R^1$ (VIIIb)

wherein $R^1$ is the same meaning as defined above.

Oxime (I) wherein n is 1 and $R^1$ is a group represented by the following formula:

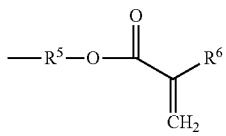

wherein $R^5$ and $R^6$ are the same meanings as defined above, can be produced by reacting a compound represented by the formula (X):

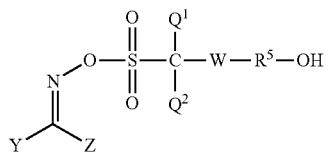
(X)

wherein Y, Z, $Q^1$, $Q^2$, W and $R^5$ are the same meanings as defined above, with acryloyl chloride or methacryloyl chloride, in an inert solvent such as toluene, tetrahydrofuran, N,N-dimethylformamide, dimethylsulfoxide, acetonitrile, chloroform and dichloromethane, in the presence of a base, at a temperature of about −100 to 150° C., preferably of −20 to 50° C., with stirring.

The amount of acryloyl chloride or methacryloyl chloride is usually 0.9 to 5 moles and preferably 1 to 1.5 moles per 1 mole of the compound represented by the formula (X).

Examples of the base include an inorganic base such as sodium hydroxide, potassium hydroxide and potassium carbonate, and an organic base such as pyridine, triethylamine and lutidine. The amount of the base is usually 1 to 5 moles and preferably 1 to 2 moles per 1 mole of the compound represented by the formula (X).

Oxime (I) wherein n is 1 and $R^1$ is a group represented by the following formula:

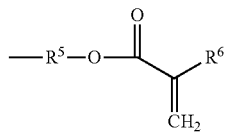

wherein $R^5$ and $R^6$ are the same meanings as defined above, can also be produced by reacting a compound represented by the formula (X) with acrylic acid or methacrylic acid, in an inert solvent such as chloroform, dichloromethane, dichloroethane, monochlorobenzene, acetone, methyl ethyl ketone, toluene, xylene, anisole, tetrahydrofuran, N,N-dimethylformamide and dimethylsulfoxide, in the presence of a dehydrating agent, at a temperature of about −30 to 200° C., preferably of −20 to 150° C. Examples of the dehydrating agent include 1,1'-carbonyldiimidazole, N,N'-dicyclohexylcarbodiimide, 1-alkyl-2-halopyridinium salt, bis(2-oxo-3-oxazolidinyl)phosphinic chloride, 1-ethyl-3-(3-dimethylaminopropyl)carbodiimide hydrochloride, di(2-pyridyl) carbonate, di(2-pyridylthiono) carbonate and 6-methyl-2-nitrobenzoic anhydride/4-(dimethylamino)pyridine (catalyst).

The amount of acrylic acid or methacrylic acid is usually 0.5 to 5 moles and preferably 0.8 to 2 moles per 1 mole of the compound represented by the formula (X). The amount of the hydrating agent is usually 1 to 3 moles and preferably 1 to 2 moles per 1 mole of the compound represented by the formula (X).

Oxime (I) wherein n is 1 and $R^1$ is a group represented by the following formula:

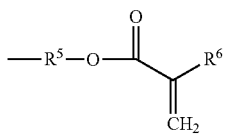

wherein $R^5$ and $R^6$ are the same meanings as defined above, can also be produced by reacting a compound represented by the formula (XI):

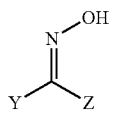

(XI)

wherein Y and Z are the same meanings as defined above, with a compound represented by the formula (XII):

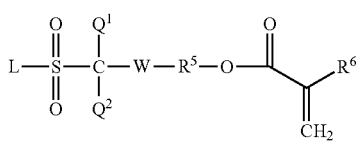

(XII)

wherein L, $Q^1$, $Q^2$, W, $R^5$ and $R^6$ are the same meanings as defined above, in an inert solvent such as toluene, tetrahydrofuran, N,N-dimethylformamide, dimethylsulfoxide, acetonitrile, chloroform and dichloromethane, in the presence of a base, at a temperature of about 0 to 150° C., preferably of 0 to 100° C. with stirring.

The amount of the compound represented by the formula (XII) is usually 0.9 to 2 moles and preferably 1 to 1.5 moles per 1 mole of the compound represented by the formula (XI). Examples of the base include an inorganic base such as sodium hydroxide, potassium hydroxide and potassium carbonate, and an organic base such as pyridine, triethylamine and lutidine. The amount of the base is usually 1 to 3 moles and preferably 1 to 2 moles per 1 mole of the compound represented by the formula (XI).

The compound represented by the formula (XII) wherein W is —CO—O— can be produced by reacting the compound represented by the formula (VIIIa) with a compound represented by the formula (XIV):

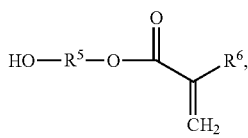

(XIV)

in an inert solvent such as chloroform, dichloromethane, dichloroethane, monochlorobenzene, acetone, methyl ethyl ketone, toluene, xylene, anisole, tetrahydrofuran, N,N-dimethylformamide and dimethylsulfoxide. The reaction temperature of the reaction above is usually about −30 to 200° C. and preferably a boiling point of the used inert solvent to 150° C. The reaction is preferably conducted in the presence of an acid catalyst, and examples of the acid catalyst include organic acids such as trifluoromethanesulfonic acid, p-toluenesulfonic acid, benzenesulfonic acid and methanesulfonic acid, inorganic acids such as sulfuric acid and hydrochloric acid, and strong acidic sulfonic acid resin such as Nafion (registered trademark). The above reaction is preferably conducted in the presence of a polymerization inhibitor such as a phenolic polymerization inhibitor such as hydroquinone and hydroquinone monomethyl ether in order to prevent the compound represented by the formula (XIV) from being polymerized during the reaction.

The amount of the compound represented by the formula (VIIIa) is usually 0.5 to 5 moles and preferably 0.8 to 2 moles per 1 mole of the compound represented by the formula (XIV). The amount of the acid catalyst is usually 0.001 to 3 moles and preferably 0.01 to 1 moles per 1 mole of the compound represented by the formula (XIV). The amount of the polymerization inhibitor is usually 0.01 ppm to 0.1 mole and preferably 1 ppm to 0.01 mole per 1 mole of the compound represented by the formula (XIV).

The reaction of the compound represented by the formula (VIIIa) and the compound represented by the formula (XIV) is also preferably conducted in the presence of a dehydrating agent. Examples of the dehydrating agent include the same as described above, and the amount of the dehydrating agent is usually 1 to 3 moles and preferably 1 to 2 moles per 1 mole of the compound represented by the formula (XIV).

Oxime (I) wherein n is 1, W is —CO—O— and $R^1$ is a group represented by the following formula:

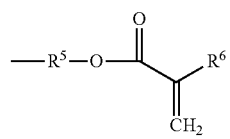

wherein $R^5$ and $R^6$ are the same meanings as defined above, can also be produced by reacting a compound represented by the formula (XV):

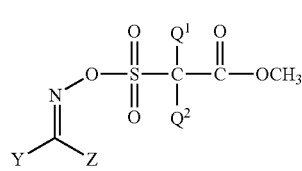

(XV)

wherein Y, Z, $Q^1$ and $Q^2$ are the same as defined above, with the compound represented by the formula (XIV), in an inert solvent such as toluene, tetrahydrofuran, dioxane, n-heptane, chloroform and dichloromethane, in the presence of a metal catalyst, at a temperature of room temperature to 150° C., preferably of 50 to 100° C. with stirring.

The amount of the compound represented by the formula (XIV) is usually 0.9 to 5 moles and preferably 1 to 2 moles per 1 mole of the compound represented by the formula (XV). Examples of the metal catalyst include titanium tetraisopropoxide and samarium triisopropoxide. The amount of the metal catalyst is usually 0.01 to 0.8 mole and preferably 0.03 to 0.2 mole per 1 mole of the compound represented by the formula (XV).

The resist composition of the present invention comprises a resin and oxime (I).

Examples of the resin include a resin comprising a structural unit having an acid-labile group and being insoluble or poorly soluble in an aqueous alkali solution but becoming soluble in an aqueous alkali solution by the action of an acid.

Oxime (I) works as an acid generator.

In this specification, "an acid-labile group" means a group capable to eliminate by the action of an acid.

In this specification, "—COOR" may be described as "a structure having ester of carboxylic acid", and may also be abbreviated as "ester group". Specifically, "—COOC(CH$_3$)$_3$" may be described as "a structure having tert-butyl ester of carboxylic acid", or be abbreviated as "tert-butyl ester group".

Examples of the acid-labile group include a structure having ester of carboxylic acid such as alkyl ester group in which a carbon atom adjacent to the oxygen atom is quaternary carbon atom, alicyclic ester group in which a carbon atom adjacent to the oxygen atom is quaternary carbon atom, and a lactone ester group in which a carbon atom adjacent to the oxygen atom is quaternary carbon atom. The "quaternary carbon atom" means a "carbon atom joined to four substituents other than hydrogen atom". Other examples of the acid-labile group include a group having a quaternary carbon atom joined to three carbon atoms and an —OR', wherein R' represents an alkyl group.

Examples of the acid-labile group include an alkyl ester group in which a carbon atom adjacent to the oxygen atom is quaternary carbon atom such as a tert-butyl ester group; an acetal type ester group such as a methoxymethyl ester, ethoxymethyl ester, 1-ethoxyethyl ester, 1-isobutoxyethyl ester, 1-isopropoxyethyl ester, 1-ethoxypropoxy ester, 1-(2-methoxyethoxy)ethyl ester, 1-(2-acetoxyethoxy)ethyl ester, 1-[2-(1-adamantyloxy)ethoxy]ethyl ester, 1-[2-(1-adamantanecarbonyloxy)ethoxy]ethyl ester, tetrahydro-2-furyl ester and tetrahydro-2-pyranyl ester group; an alicyclic ester group in which a carbon atom adjacent to the oxygen atom is quaternary carbon atom, such as an isobornyl ester, 1-alkylcycloalkyl ester, 2-alkyl-2-adamantyl ester and 1-(1-adamantyl)-1-alkylalkyl ester group. At least one hydrogen atom in the adamantyl group may be substituted with a hydroxyl group.

Examples of the structural unit having an acid-labile group include a structure unit derived from an ester of acrylic acid, a structural unit derived from an ester of methacrylic acid, a structural unit derived from an ester of norbornenecarboxylic acid, a structural unit derived from an ester of tricyclodecenecarboxylic acid and a structural unit derived from an ester of tetracyclodecenecarboxylic acid. The structure units derived from the ester of acrylic acid and from the ester of methacrylic acid are preferable.

The resin used for the present composition can be obtained by conducting polymerization reaction of a monomer or monomers having the acid-labile group and an olefinic double bond.

Among the monomers, those having a bulky and acid-labile group such as an alicyclic ester group (e.g. a 2-alkyl-2-adamantyl ester and 1-(1-adamantyl)-1-alkylalkyl ester group) are preferable, since excellent resolution is obtained when the resin obtained is used in the present resist composition.

Examples of such monomer containing the bulky and acid-labile group include a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate.

Particularly when the 2-alkyl-2-adamantyl acrylate, the 2-alkyl-2-adamantyl methacrylate or the 2-alkyl-2-adamantyl α-chloroacrylate is used as the monomer for the resin component in the present resist composition, a resist composition having excellent resolution tend to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate and 2-ethyl-2-adamantyl α-chloroacrylate.

When particularly 2-ethyl-2-adamantyl acrylate, 2-ethyl-2-adamantyl methacrylate, 2-isopropyl-2-adamantyl acrylate or 2-isopropyl-2-adamantyl methacrylate is used for the present resist composition, a resist composition having excellent sensitivity and heat resistance tends to be obtained. In the present invention, two or more kinds of monomers having a group or groups dissociated by the action of the acid may be used together, if necessary.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide.

The resin may also contain a structural unit represented by the formula (Xa):

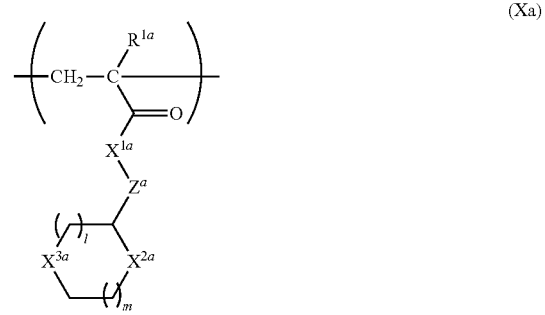

wherein $R^{1a}$ represents a hydrogen atom, a halogen atom, a C1-C4 alkyl group or a C1-C4 perfluoroalkyl group, $Z^a$ represents a single bond or a —[CH$_2$]$_a$—CO—$X^{4a}$—, $X^{1a}$, $X^{2a}$, $X^{3a}$ and $X^{4a}$ each independently represents —O— or —S—, a represents an integer of 1 to 4, 1 represents an integer of 1 to 3 and m represents an integer of 0 to 3, as a structural unit having an acid-labile group.

Examples of the halogen atom include a fluorine atom and a chlorine atom. Examples of the C1-C4 alkyl group include a methyl group, an ethyl group, an n-propyl group, an isopropyl group, an n-butyl group and a tert-butyl group. Examples of the C1-C4 perfluoroalkyl group include a trifluoromethyl group, a pentafluoroethyl group, a heptafluoropropyl group and a nonafluorobutyl group.

Examples of a monomer used to give a structural unit represented by the formula (Xa) include the followings:

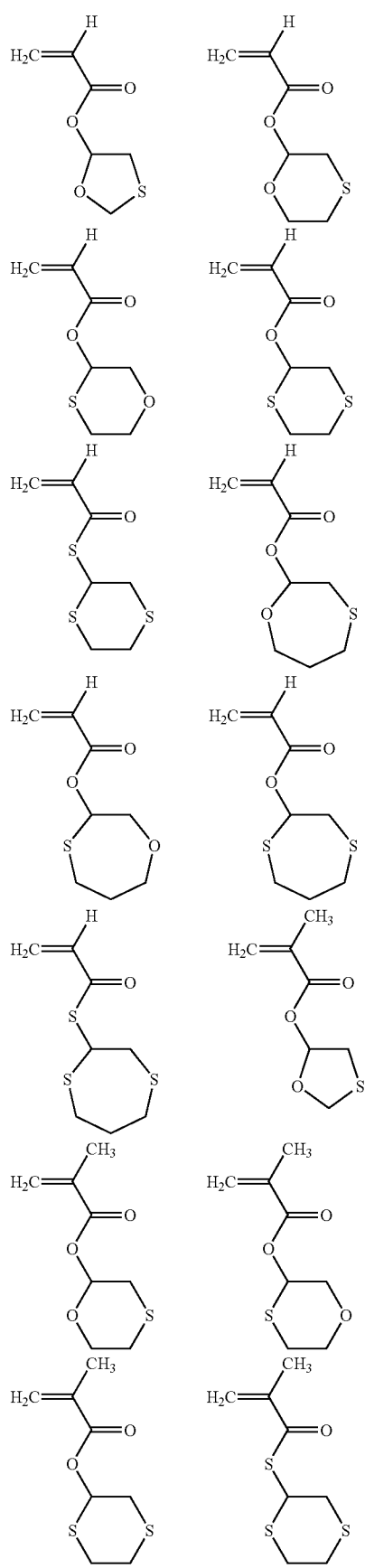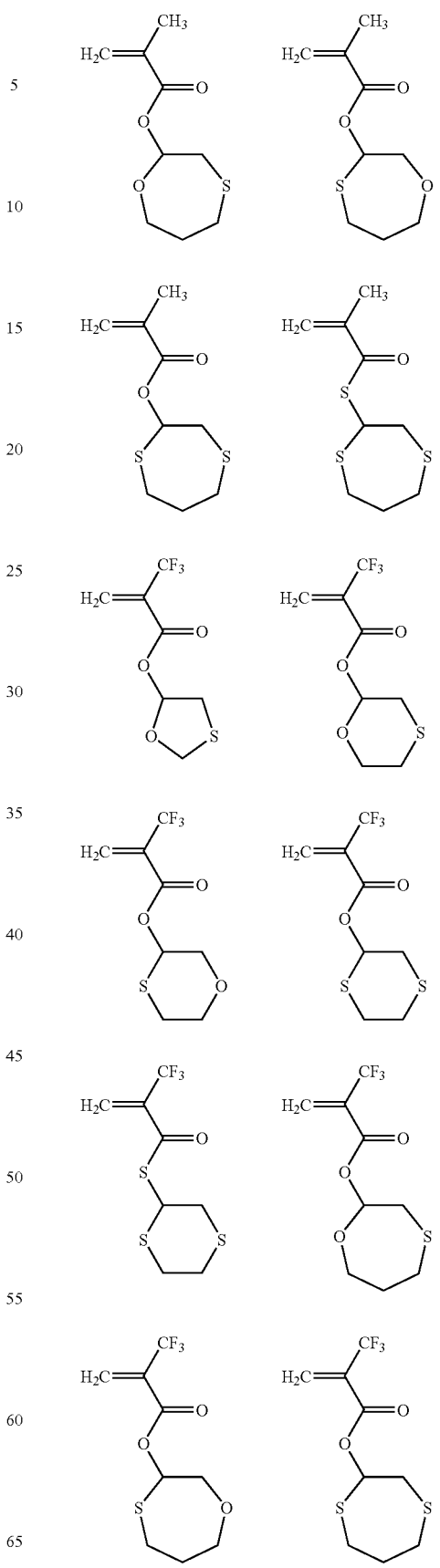

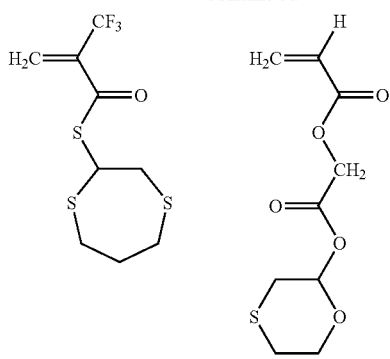

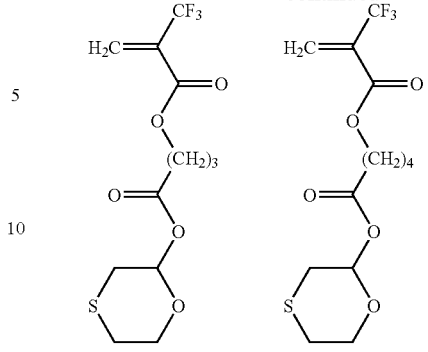

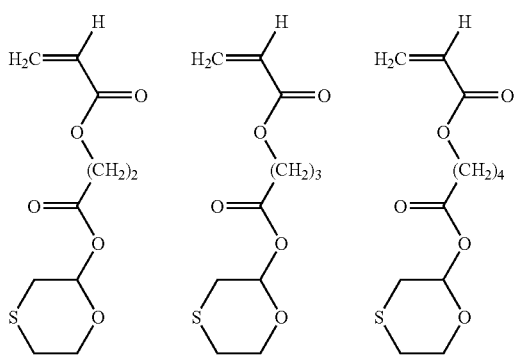

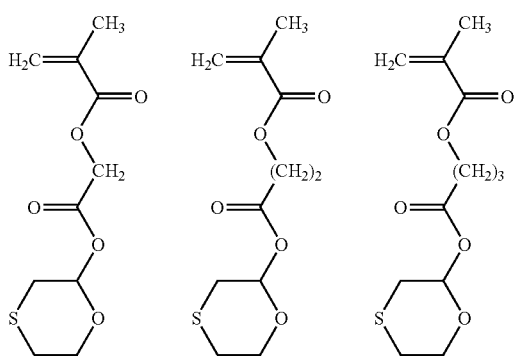

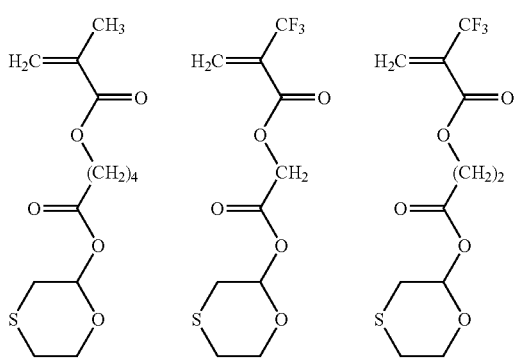

These monomers can be produced by reacting the corresponding alcohol compound with acryloyl chloride or methacryloyl chloride in the presence of a base.

The resin used for the present resist composition can also contain other structural unit or units derived from an acid-stable monomer in addition to the above-mentioned structural units having the acid-labile group. Herein, the "structural unit derived from an acid-stable monomer" means "a structural unit not dissociated by an acid.

Examples of such other structural unit derived from the acid-stable monomer include a structural unit derived from a monomer having a free carboxyl group such as acrylic acid and methacrylic acid; a structural unit derived from an aliphatic unsaturated dicarboxylic anhydride such as maleic anhydride and itaconic anhydride; a structural unit derived from 2-norbornene; a structural unit derived from acrylonitrile or methacrylonitrile; a structural unit derived from an alkyl acrylate or an alkyl methacrylate in which a carbon atom adjacent to oxygen atom is secondary or tertiary carbon atom; a structural unit derived from 1-adamantyl acrylate or 1-adamantyl methacrylate; a structural unit derived from styrene monomer such as p-hydroxystyrene and m-hydroxystyrene; a structural unit derived from acryloyloxy-γ-butyrolactone or methacryloyloxy-γ-butyrolactone having a lactone ring which may be substituted with an alkyl group; and the like. Herein, the 1-adamantyloxycarbonyl group is the acid-stable group though the carbon atom adjacent to oxygen atom is the quaternary carbon atom, and the 1-adamantyloxycarbonyl group may be substituted with at least one hydroxyl group.

Specific examples of the structural unit derived from the acid-stable monomer include a structural unit derived from 3-hydroxy-1-adamantyl acrylate;

a structural unit derived from 3-hydroxy-1-adamantyl methacrylate;

a structural unit derived from 3,5-dihydroxy-1-adamantyl acrylate;

a structural unit derived from 3,5-dihydroxy-1-adamantyl methacrylate;

a structural unit derived from α-acryloyloxy-γ-butyrolactone;

a structural unit derived from α-methacryloyloxy-γ-butyrolactone;

a structural unit derived from β-acryloyloxy-γ-butyrolactone;

a structural unit derived from β-methacryloyloxy-γ-butyrolactone;

a structural unit represented by the formula (k1):

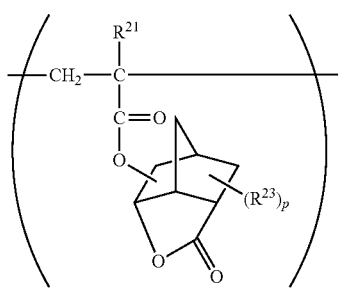
(k1)

wherein $R^{21}$ represents a hydrogen atom or a methyl group, $R^{23}$ is independently in each occurrence a methyl group, a trifluoromethyl group or a halogen atom, and p represents an integer of 0 to 3;

a structural unit represented by the formula (k2):

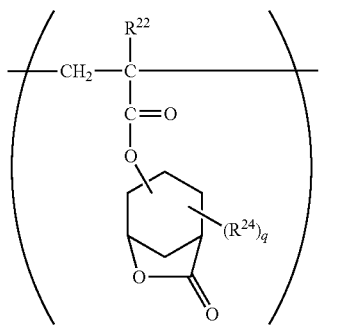
(k2)

wherein $R^{22}$ represents a hydrogen atom or a methyl group, $R^{24}$ is independently in each occurrence a methyl group, a trifluoromethyl group or a halogen atom, and q represents an integer of 0 to 3;

a structural unit derived from p-hydroxystyrene;

a structural unit derived from m-hydroxystyrene;

a structural unit derived from an alicyclic compound having an olefinic double bond such as a structural unit represented by the formula (k3):

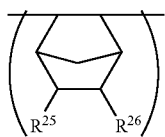
(k3)

wherein $R^{25}$ and $R^{26}$ each independently represents a hydrogen atom, a C1-C3 alkyl group, a C1-C3 hydroxyalkyl group, a carboxyl group, a cyano group, a hydroxyl group or a —COOU group in which U represents an alcohol residue, or $R^{25}$ and $R^{26}$ can be bonded together to form a carboxylic anhydride residue represented by —C(=O)OC(=O)—;

a structural unit derived from an aliphatic unsaturated dicarboxylic anhydride such as a structural unit represented by the formula (k4):

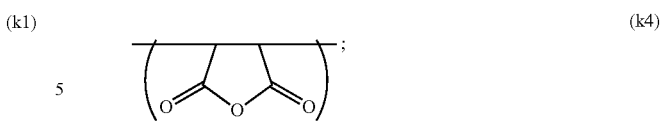
(k4)

a structural unit represented by the formula (5):

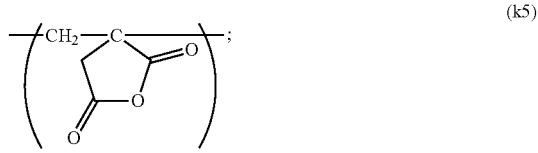
(k5)

and the like.

Particularly, the resin having further at least one structural unit selected from the group consisting of the structural unit derived from p-hydroxystyrene, the structural unit derived from m-hydroxystyrene, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit represented by the formula (k1) and the structural unit represented by the formula (k2) in addition to the structural unit having the acid-labile group is preferable from the standpoint of the adhesiveness of resist to a substrate and resolution of resist.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

Further, the acryloyloxy-γ-butyrolactone and the methacryloyloxy-γ-butyrolactone can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

Examples of the monomers to give structural units represented by the formulae (k1) and (k2) include an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

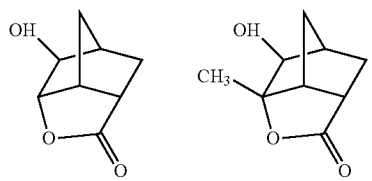

-continued

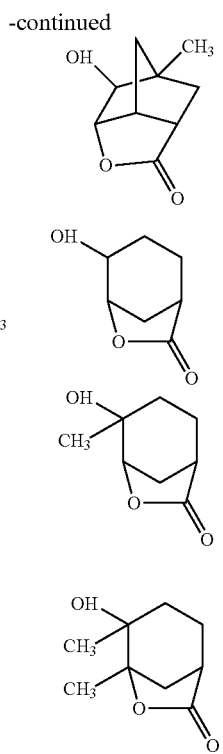

Examples of the acryloyloxy-γ-butyrolactone and the methacryloyloxy-γ-butyrolactone in which lactone ring may be substituted with the alkyl group include
α-acryloyloxy-γ-butyrolactone,
α-methacryloyloxy-γ-butyrolactone,
α-acryloyloxy-β,β-dimethyl-γ-butyrolactone,
α-methacryloyloxy-β,β-dimethyl-γ-butyrolactone,
α-acryloyloxy-α-methyl-γ-butyrolactone,
α-methacryloyloxy-α-methyl-γ-butyrolactone,
β-acryloyloxy-γ-butyrolactone,
β-methacryloyloxy-γ-butyrolactone and
β-methacryloyloxy-α-methyl-γ-butyrolactone.

The resin containing a structural unit derived from 2-norbornene shows strong structure because the alicyclic group is directly present on its main chain and shows a property that dry etching resistance is excellent. The structural unit derived from 2-norbornene can be introduced into the main chain by radical polymerization using, for example, an aliphatic unsaturated dicarboxylic anhydride such as maleic anhydride and itaconic anhydride together in addition to corresponding 2-norbornene. The structural unit derived from 2-norbornene is formed by opening of its double bond, and can be represented by the above-mentioned formula (k3). The structural units derived from maleic anhydride and from itaconic anhydride which are the structural unit derived from aliphatic unsaturated dicarboxylic anhydrides are formed by opening of their double bonds, and can be represented by the above-mentioned formula (k4) and the formula (k5), respectively.

In $R^{25}$ and $R^{26}$, examples of the C1-C3 alkyl group include a methyl, ethyl, and n-propyl group, and examples of the C1-C3 hydroxyalkyl group include a hydroxymethyl and 2-hydroxyethyl group.

In $R^{25}$ and $R^{26}$, the —COOU group is an ester formed from the carboxyl group, and examples of the alcohol residue corresponding to U include an optionally substituted C1-C8 alkyl group, 2-oxooxolan-3-yl group and 2-oxooxolan-4-yl group, and examples of the substituent on the C1-C8 alkyl group include a hydroxyl group and an alicyclic hydrocarbon.

Specific examples of the monomer used to give the structural unit represented by the above-mentioned formula (k3) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (k3) is a structural unit having the acid-labile group even if it has the norbornane structure. Examples of monomers giving a structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

The resin may contain a structural unit represented by the formula (b1):

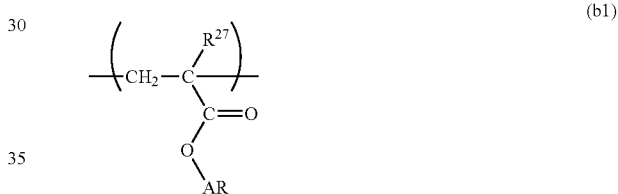

(b1)

wherein $R^{27}$ represents a hydrogen atom, a methyl group or a trifluoromethyl group, and AR represents a C1-C30 fluorine-containing linear, branched chain or cyclic hydrocarbon group which may contain one or more hydroxyl groups and in which at least one methylene group may be replaced by —O—, —S— or —N($R^c$)— and $R^c$ is the same meaning as defined above, or a structural unit having one or more fluorine atoms.

Examples of a monomer giving the structural unit represented by the formula (b1) include the followings:

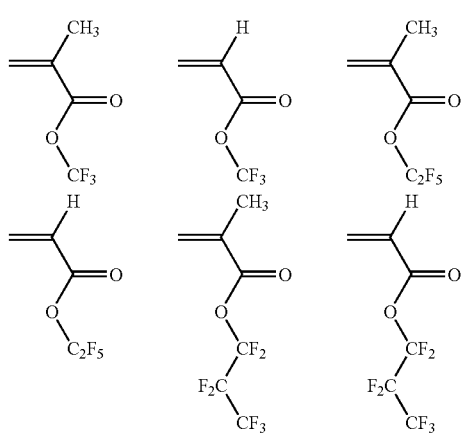

61
-continued
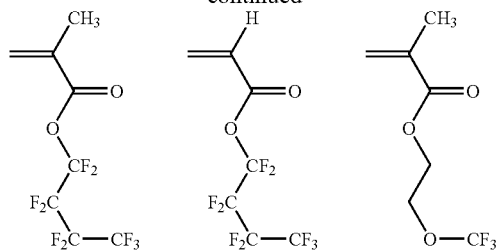
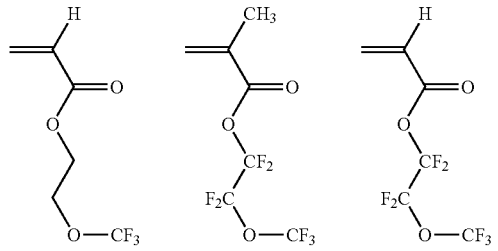
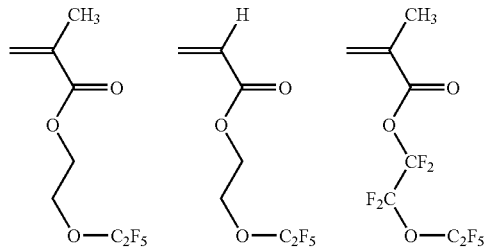
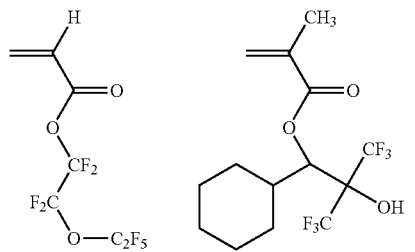
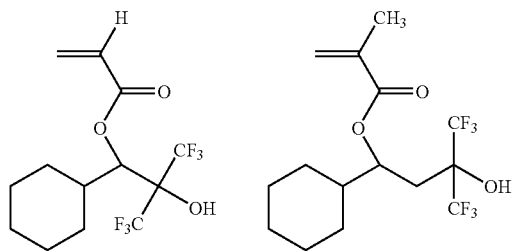
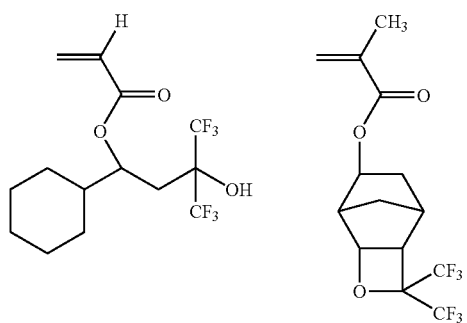
62
-continued
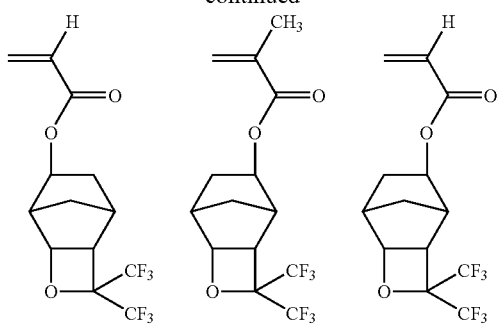
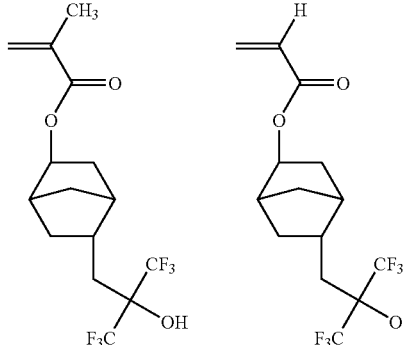
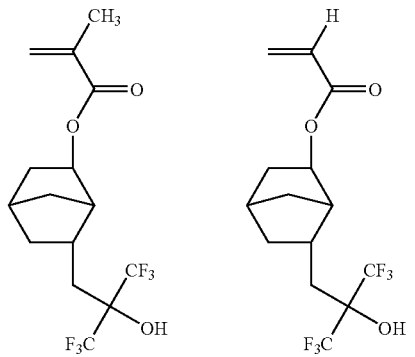
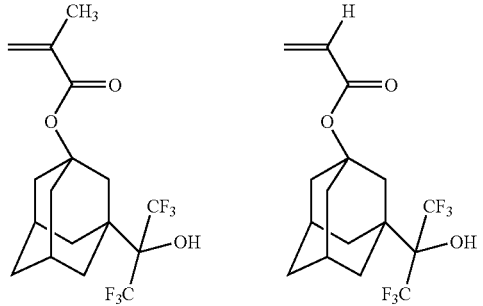
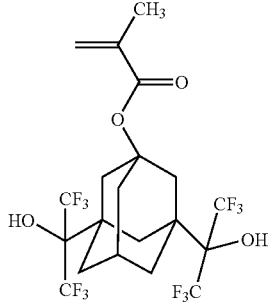

-continued

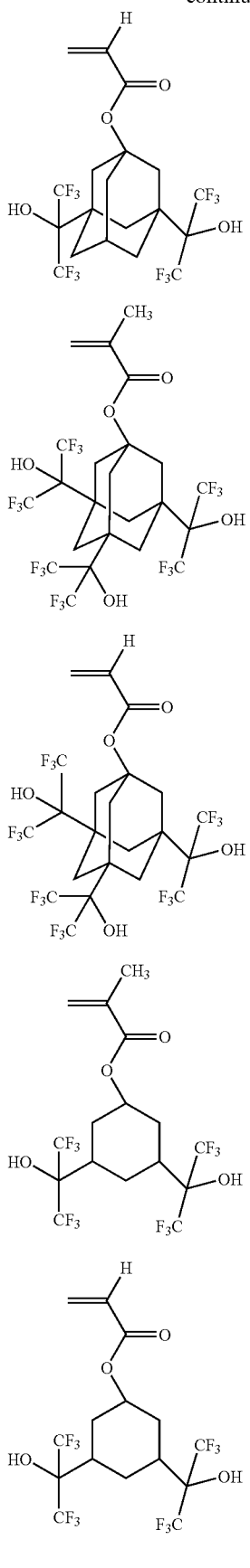

-continued

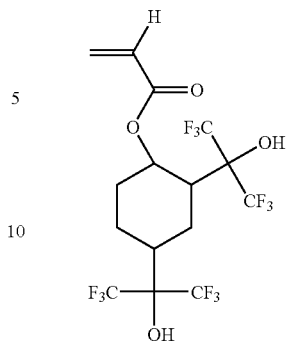

The resin used in the present composition preferably contains the structural unit having an acid-labile group generally in a ratio of 10 to 80% by mole in all structural units of the resin though the ratio varies depending on the kind of radiation for patterning exposure, the kind of the acid-labile group, and the like.

When the structural units particularly derived from the 2-alkyl-2-adamantyl acrylate, the 2-alkyl-2-adamantyl methacrylate, the 1-(1-adamantyl)-1-alkylalkyl acrylate or the 1-(1-adamantyl)-1-alkylalkyl methacrylate are used as the structural unit having the acid-labile group, it is advantageous in dry-etching resistance of the resist that the ratio of said structural units is 15% by mole or more in all structural units of the resin.

The resin may have a structural unit derived from the oxime compound represented by the formula (Va).

The resin used in the present invention can be usually produced by conducting a polymerization reaction of the corresponding monomer or monomers. The resin can be also produced by conducting an oligomerization reaction of the corresponding monomer or monomers followed by polymerizing the oligomer obtained.

The polymerization reaction is usually carried out in the presence of a radical initiator.

The radical initiator is not limited and examples thereof include an azo compound such as 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile), 2,2'-azobis(2,4-dimethyl-4-methoxyvaleronitrile), dimethyl-2,2'-azobis(2-methylpropionate) and 2,2'-azobis(2-hydroxymethylpropionitrile); an organic hydroperoxide such as lauroyl peroxide, tert-butyl hydroperoxide, benzoyl peroxide, tert-butyl peroxybenzoate, cumene hydroperoxide, diisopropyl peroxydicarbonate, di-n-propyl peroxydicarbonate, tert-butyl peroxyneodecanoate, tert-butyl peroxypivalate and 3,5,5-trimethylhexanoyl peroxide; and an inorganic peroxide such as potassium peroxodisulfate, ammonium peroxodisulfate and hydrogen peroxide. Among them, the azo compound is preferable and 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile) and dimethyl-2,2'-azobis(2-methylpropionate) are more preferable.

These radical initiators may be used alone or in a form of a mixture of two or more kinds thereof. When the mixture of two or more kinds thereof is used, the mixed ratio is not limited.

The amount of the radical initiator is preferably 1 to 20% by mole based on all monomer or oligomer molar amount.

The polymerization temperature is usually 0 to 150° C., and preferably 40 to 100° C.

The polymerization reaction is usually carried out in the presence of a solvent and it is preferred to use a solvent which is sufficient to dissolve the monomer, the radical initiator and the resin obtained. Examples thereof include a hydrocarbon solvent such as toluene; an ether solvent such as 1,4-dioxane and tetrahydrofuran; a ketone solvent such as methyl isobutyl ketone; an alcohol solvent such as isopropyl alcohol; a cyclic ester solvent such as γ-butyrolactone; a glycol ether ester ester solvent such as propylene glycol monomethyl ether acetate; and an acyclic ester solvent such as ethyl lactate. These solvents may be used alone and a mixture thereof may be used.

The amount of the solvent is not limited, and practically, it is preferably 1 to 5 parts by weight relative to 1 part of all monomers or oligomers.

When an alicyclic compound having an olefinic double bond and an aliphatic unsaturated dicarboxylic anhydride are used as monomers, it is preferable to use them in excess amount in view of a tendency that these are not easily polymerized.

After completion of the polymerization reaction, the resin produced can be isolated, for example, by adding a solvent in which the present resin is insoluble or poorly soluble to the reaction mixture obtained and filtering the precipitated resin. If necessary, the isolated resin may be purified, for example, by washing with a suitable solvent.

The polymer of the present invention comprises a structural unit derived from the oxime compound represented by the formula (Va), which is a novel polymer.

The present polymer may consist of the structural unit derived from the oxime compound represented by the formula (Va) and may contain other structural unit or units in addition to the structural unit derived from the oxime compound represented by the formula (Va).

Examples of the other structural unit include a structural unit having an acid-labile group, a structural unit having an acid-stable group. Examples of the structural unit having an acid-labile group and the structural unit having an acid-stable group include the same as described above.

When the polymer of the present invention contains the structural unit having an acid-labile group, the ratio of the structural unit having an acid-labile group is usually 5 to 95% by mole and preferably 30 to 90% by mole in all structural units of the polymer.

When the present polymer contains the structural unit having an acid-stable group, the ratio of the structural unit having an acid-stable group is usually 5 to 95% by mole, preferably 30 to 60% by mole and more preferably 40 to 50% by mole in all structural units of the resin.

The polymer of the present invention can be prepared by polymerizing the oxime compound represented by the formula (Va) or polymerizing the oxime compound represented by the formula (Va) and the other monomer or monomers.

The resist composition of the present invention may contain the polymer of the present invention, and may contain the above-mentioned resin and the polymer of the present invention. This polymerization reaction can be conducted according to the polymerization reaction described above.

As described above, oxime (I) works as an acid generator. The resist composition of the present invention also contains the other acid generators).

The acid generator is a substance which is decomposed to generate an acid by applying a radiation such as a light, an electron beam or the like on the substance itself or on a resist composition containing the substance. The acid generated from the acid generator acts on the resin and/or the present polymer resulting in cleavage of the acid-labile group existing in the resin and/or the present polymer.

Examples of the acid generator include ammonium salt compound, an organo-halogen compound, a sulfone compound and a sulfonate compound. The onium salt compound is preferable.

The acid generators described in JP 2003-5374 A1 can be also used in the present resist composition.

Examples of the onium salt compound include diphenyliodonium trifluoromethanesulfonate, 4-methoxyphenylphenyliodonium hexafluoroantimonate, 4-methoxyphenylphenyliodonium trifluoromethanesulfonate, bis(4-tert-butylphenyl)iodonium tetrafluoroborate, bis(4-tert-butylphenyl)iodonium hexafluorophosphate, bis(4-tert-butylphenyl)iodonium hexafluoroantimonate, bis(4-tert-butylphenyl)iodonium trifluoromethanesulfonate, triphenylsulfonium hexafluorophosphate, triphenylsulfonium hexafluoroantimonate, triphenylsulfonium trifluoromethanesulfonate, triphenylsulfonium adamantylmethoxycarbonyldifluoromethanesulfonate, triphenylsulfonium (3-hydroxyadamantyl)methoxycarbonyldifluoromethanesulfonate, triphenylsulfonium 1-(3-hydroxymethyladamantyl)methoxycarbonyldifluoromethanesulfonate, triphenylsulfonium 1-(hexahydro-2-oxo-3,5-methano-2H-cyclopenta[b]furan-6-yloxy carbonyl)difluoromethanesulfonate, triphenylsulfonium 4-oxo-1-adamantyloxycarbonyldifluoromethanesulfonate, 4-methoxyphenyldiphenylsulfonium hexafluoroantimonate, 4-methoxyphenyldiphenylsulfonium trifluoromethanesulfonate, p-tolyldiphenylsulfonium trifluoromethanesulfonate, p-tolyldiphenylsulfonium heptadecafluorooctanesulfonate, 2,4,6-trimethylphenyldiphenylsulfonium trifluoromethanesulfonate, 4-tert-butylphenyldiphenylsulfonium trifluoromethanesulfonate, 4-phenylthiophenyldiphenylsulfonium hexafluorophosphate, 4-phenylthiophenyldiphenylsulfonium hexafluoroantimonate, 1-(2-naphthoylmethyl)thiolanium hexafluoroantimonate, 1-(2-naphthoylmethyl)thiolanium trifluoromethanesulfonate, 4-hydroxy-1-naphthyldimethylsulfonium hexafluoroantimonate and 4-hydroxy-1-naphthyldimethylsulfonium trifluoromethanesulfonate.

Examples of the organic halide compound include 2-methyl-4,6-bis(trichloromethyl)-1,3,5-triazine, 2,4,6-tris(trichloromethyl)-1,3,5-triazine, 2-phenyl-4,6-bis(trichloromethyl)-1,3,5-triazine, 2-(4-chlorophenyl)-4,6-bis(trichloromethyl)-1,3,5-triazine, 2-(4-methoxyphenyl)-4,6-bis(trichloromethyl)-1,3,5-triazine, 2-(4-methoxy-1-naphthyl)-4,6-bis(trichloromethyl)-1,3,5-triazine, 2-(benzo[d][1,3]dioxoran-5-yl)-4,6-bis(trichloromethyl)-1,3,5-triazine, 2-(4-methoxystyryl)-4,6-bis(trichloromethyl)-1,3,5-triazine, 2-(3,4,5-trimethoxystyryl)-4,6-bis(trichloromethyl)-1,3,5-triazine, 2-(3,4-dimethoxystyryl)-4,6-bis(trichloromethyl)-1,3,5-triazine, 2-(2,4-dimethoxystyryl)-4,6-bis(trichloromethyl)-1,3-triazine, 2-(2-methoxystyryl)-4,6-bis(trichloromethyl)-1,3,5-triazine, 2-(4-butoxystyryl)-4,6-bis(trichloromethyl)-1,3,5-triazine and 2-(4-pentyloxystyryl)-4,6-bis(trichloromethyl)-1,3,5-triazine.

Examples of the sulfone compound include diphenyl disulfone, di-p-tolyl disulfone, bis(phenylsulfonyl)diazomethane, bis(4-chlorophenylsulfonyl)diazomethane, bis(p-tolylsulfonyl)diazomethane, bis(4-tert-butylphenylsulfonyl)diazomethane, bis(2,4-xylylsulfonyl)diazomethane, bis(cyclohexylsulfonyl)diazomethane, (benzoyl)(phenylsulfonyl)diazomethane, N-(phenylsulfonyloxy)succinimide, N-(trifluoromethylsulfonyloxy)succinimide, N-(trifluoromethylsulfonyloxy)phthalimide, N-(trifluoromethylsulfonyloxy)-5-norbornene-2,3-dicarbodiimide, N-(trifluoromethylsulfonyloxy)naphthalimide and N-(10-canmphorsulufonyloxy) naphthalimide.

Examples of the sulfonate compound include 1-benzoyl-1-phenylmethyl p-toluenesulfonate, 2-benzoyl-2-hydroxy-2-phenylethyl o-toluenesulfonate, 1,2,3-benzenetriyl tris-methansulfonate, 2,6-dinitrobenzyl p-toluenesulfonate, 2-nitrobenzyl p-toluenesulfonate and 4-nitrobenzyl p-toluenesulfonate.

The present resist composition preferably includes 0.1 to 50% by weight of the other acid generator based on the amount of the resin component.

The present polymer works as an acid generator.

The present resist composition preferably includes 80 to 99.9% by weight of the resin component and 0.1 to 20% by weight of the acid generator component based on sum of the resin component and the acid generator component. Herein, "acid generator component" means oxime (I), the present polymer comprising the structural unit derived from the oxime compound represented by the formula (Va), the other acid generators) or a mixture thereof.

When the resist composition contains oxime (I) and the other acid generator(s), although the ratio of the present polymer and the other acid generators) is not limited, it is usually 0.01/99.99 to 99.99/0.01.

When the resist composition contains the present polymer comprising the structural unit derived from the oxime compound represented by the formula (Va) and the other acid generator(s), although the ratio of the present polymer and the other acid generators is not limited, it is usually 0.01/99.99 to 99.99/0.01.

The present resist composition may contain oxime (I) and the present polymer, and the ratio of the present polymer and the other acid generators) is not limited.

In the present resist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

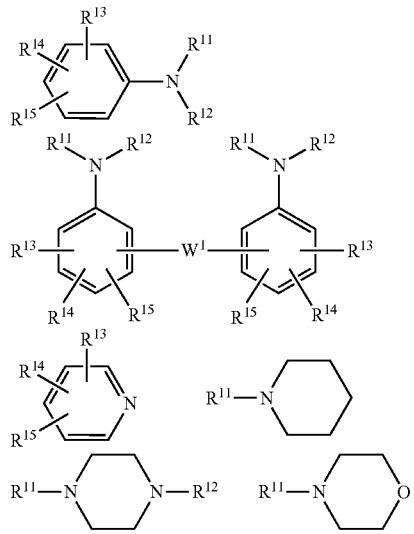

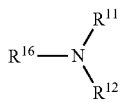

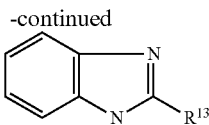

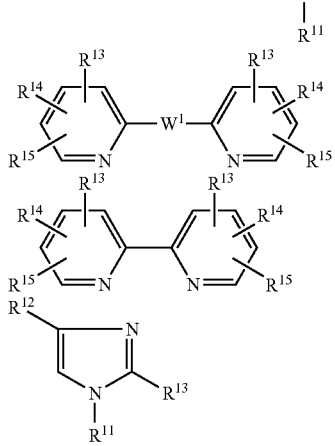

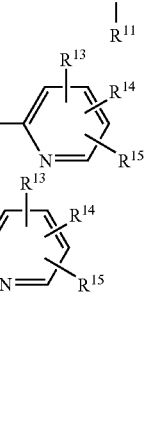

wherein $R^{11}$ and $R^{12}$ independently represent a hydrogen atom, an alkyl group, a cycloalkyl group or an aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group which may be substituted with a C1-C6 alkoxy group, $R^{13}$ and $R^{14}$ independently represent a hydrogen atom, an alkyl group, a cycloalkyl group, an aryl group or an alkoxy group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, or $R^{13}$ and $R^{14}$ bond together with the carbon atoms to which they bond to form an aromatic ring, $R^{15}$ represent a hydrogen atom, an alkyl group, a cycloalkyl group, an aryl group, an alkoxy group or a nitro group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, $R^{16}$ represents an alkyl or cycloalkyl group, and the alkyl and cycloalkyl groups may be substituted with at least one group selected from the group consisting of a hydroxyl group, an amino group which may be substituted with a C1-C4 alkyl group and a C1-C6 alkoxy group, and $W^1$ represents —CO—, —NH—, —S—, —S—S—, an alkylene group of which at least one methylene group may be replaced with —O—, or an alkenylene group of which at least one methylene group may be replaced with —O—, and a quaternary ammonium hydroxide represented by the following formula:

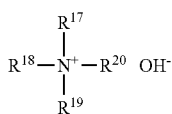

wherein $R^{17}$, $R^{18}$, $R^{19}$ and $R^{20}$ independently represent an alkyl group, a cycloalkyl group or an aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group.

The alkyl group in $R^{11}$, $R^{12}$ $R^{13}$, $R^{14}$, $R^{15}$, $R^{16}$, $R^{17}$, $R^{18}$, $R^{19}$ and $R^{20}$ preferably has about 1 to 10 carbon atoms, and more preferably has about 1 to 6 carbon atoms.

Examples of the amino group which may be substituted with the C1-C4 alkyl group include an amino, methylamino, ethylamino, n-butylamino, dimethylamino and diethylamino group. Examples of the C1-C6 alkoxy group which may be substituted with the C1-C6 alkoxy group include a methoxy, ethoxy, n-propoxy, isopropoxy, n-butoxy, tert-butoxy, n-pentyloxy, n-hexyloxy and 2-methoxyethoxy group.

Specific examples of the alkyl group which may be substituted with at least one group selected from the group consisting of a hydroxyl group, an amino group which may be substituted with a C1-C4 alkyl group, and a C1-CC alkoxy group which may be substituted with a C1-C6 alkoxy group include a methyl, ethyl, n-propyl, isopropyl, n-butyl, tert-butyl, n-pentyl, n-hexyl, n-octyl, n-nonyl, n-decyl, 2-(2-methoxyethoxy)ethyl, 2-hydroxyethyl, 2-hydroxypropyl, 2-aminoethyl, 4-aminobutyl and 6-aminohexyl group.

The cycloalkyl group in $R^{11}$, $R^{12}$, $R^{13}$, $R^{14}$, $R^{15}$, $R^{16}$, $R^{17}$, $R^{18}$, $R^{19}$ and $R^{20}$ preferably has about 5 to 10 carbon atoms. Specific examples of the cycloalkyl group which may be substituted with at least one group selected from the group consisting of a hydroxyl group, an amino group which may be substituted with a C1-C4 alkyl group and a C1-C6 alkoxy group include a cyclopentyl, cyclohexyl, cycloheptyl and cyclooctyl group.

The aryl group in $R^{11}$, $R^{12}$, $R^{13}$, $R^{14}$, $R^{15}$, $R^{17}$, $R^{18}$, $R^{19}$ and $R^{20}$ preferably has about 6 to 10 carbon atoms. Specific examples of the aryl group which may be substituted with at least one group selected from the group consisting of a hydroxyl group, an amino group which may be substituted with a C1-C4 alkyl group and a C1-C6 alkoxy group include a phenyl and naphthyl group.

The alkoxy group in $R^{13}$, $R^{14}$ and $R^{15}$ preferably has about 1 to 6 carbon atoms and specific examples thereof include a methoxy, ethoxy, n-propoxy, isopropoxy, n-butoxy, tert-butoxy, n-pentyloxy and n-hexyloxy group.

The alkylene and alkenylene groups in W preferably have 2 to 6 carbon atoms. Specific examples of the alkylene group include an ethylene, trimethylene, tetramethylene, methylenedioxy and ethylene-1,2-dioxy group, and specific examples of the alkenylene group include an ethene-1,2-diyl, 1-propene-1,3-diyl and 2-butene-1,4-diyl group.

Specific examples of the amine compound include n-hexylamine, n-heptylamine, n-octylamine, n-nonylamine, n-decylamine, aniline, 2-methylaniline, 4-methylaniline; 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl] amine, triisopropanolamine, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl) ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skelton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound based on the total amount of the resin component and the acid generator component.

The present resist composition can contain, if necessary, a small amount of various additives such as a sensitizer, a dissolution inhibitor, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns): TSKgel Multipore HXL-M, Solvent: Tetrahydrofuran, manufactured by TOSOH CORPORATION] using styrene as a standard reference material. Structures of compounds were determined by NMR (GX-270 Type, or EX-270 Type, manufactured by JEOL LTD.) and mass spectrometry (Liquid Chromatography: 1100 Type, manufactured by AGILENT TECHNOLOGIES LTD., Mass Spectrometry: LC/MSD Type or LC/MSD TOF Type, manufactured by AGILENT TECHNOLOGIES LTD.).

Example 1

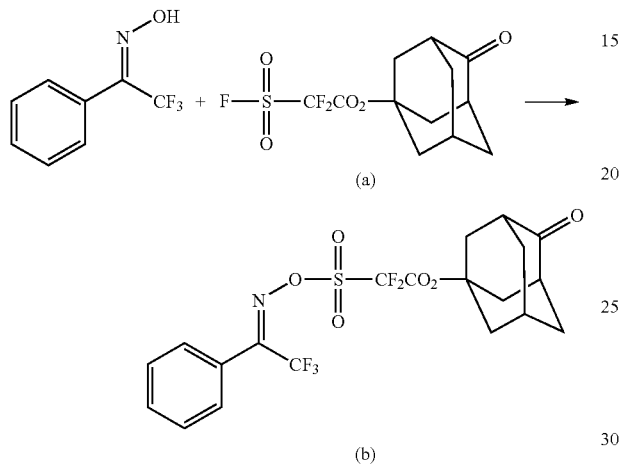

To the solution prepared by dissolving 5.0 parts of trifluoroacetophenone oxime in 6.6 parts of N,N-dimethylformamide, 3.0 parts of 2,6-lutidine and 9.9 parts of the compound represented by the above-mentioned formula (a) were added. The resultant mixture was stirred for 16 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 8.7 parts of the compound represented by the above-mentioned formula (b) which is called as B1.

$^{1}$H-NMR (dimethylsulfoxide-$d_6$): δ (ppm) 7.74-7.61 (5H, m), 2.54 (2H, s), 2.31-2.23 (7H, m), 1.98 (2H, d, J=12.2 Hz), 1.84 (2H, d, J=12.2 Hz)

$^{19}$F-NMR (dimethylsulfoxide-$d_6$): δ (ppm) −61.96, −99.47

MS (ESI (+) Spectrum): [M+Na]$^+$ 518.0 ($C_{20}H_{18}F_5NO_6S^+$=495.08)

Example 2

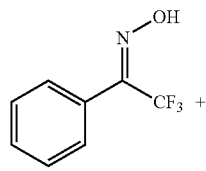

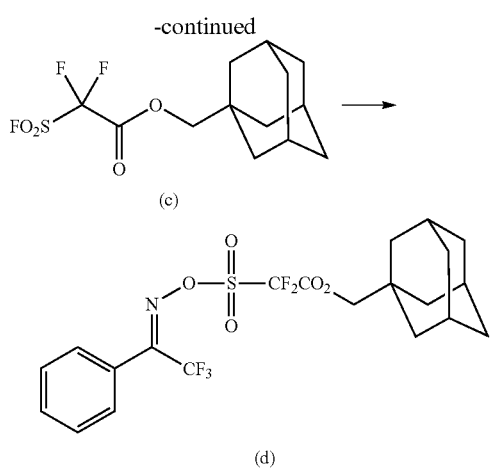

To the solution prepared by dissolving 3.0 parts of trifluoroacetophenone oxime in 4.0 parts of N,N-dimethylformamide, 1.8 parts of 2,6-lutidine and 6.6 parts of the compound represented by the above-mentioned formula (c) were added. The resultant mixture was stirred for 16 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 5.0 parts of the compound represented by the above-mentioned formula (d), which is called as B2.

$^{1}$H-NMR (dimethylsulfoxide-$d_6$): δ(ppm) 7.74-7.69 (1H, m), 7.69-7.63 (2H, m), 7.60 (2H, d, J=6.9 Hz), 4.00 (2H, s), 1.94-1.90 (3H, m), 1.62 (6H, dd, J-51.6 Hz, 11.8 Hz), 1.47 (6H, d, J=2.3 Hz)

$^{19}$F-NMR (dimethylsulfoxide-$d_6$): δ(ppm) −62.25, −99.26

Example 3

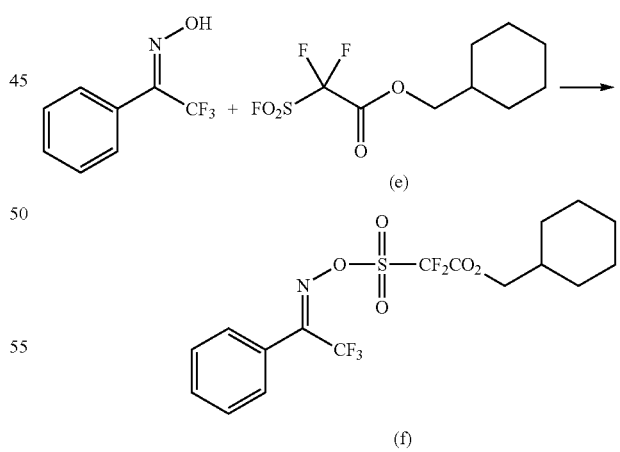

To the solution prepared by dissolving 2.0 parts of trifluoroacetophenone oxime in 3.0 parts of N,N-dimethylformamide, 0.9 part of 2,6-lutidine and 2.0 parts of the compound represented by the above-mentioned formula (e) were added. The resultant mixture was stirred for 17 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 1.9 parts of the compound represented by the above-mentioned formula (f), which is called as B3.

$^1$H-NMR (dimethylsulfoxide-$d_6$): δ (ppm) 7.74-7.59 (5H, m), 4.22 (2H, d, J=6.1 Hz), 1.72-1.57 (6H, m), 1.27-0.87 (5H, m)

$^{19}$F-NMR (dimethylsulfoxide-$d_6$): δ (ppm) −62.25, −99.50

MS (ESI (+) Spectrum): [M+Na]$^+$ 466.0 ($C_{17}H_{18}F_5NO_3S$=443.0)

Example 4

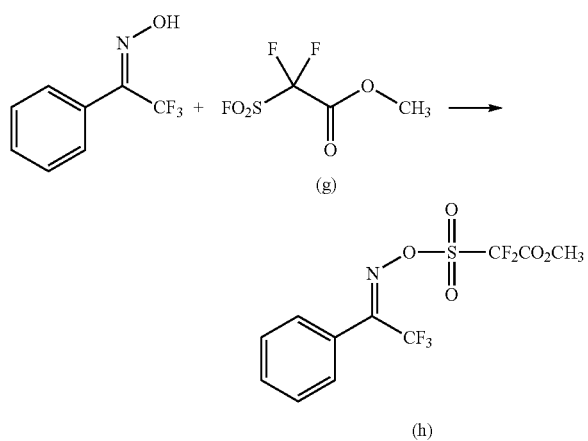

To the solution prepared by dissolving 2.0 parts of trifluoroacetophenone oxime in 3.0 parts of N,N-dimethylformamide, 0.9 part of 2,6-lutidine and 1.6 parts of the compound represented by the above-mentioned formula (g) were added. The resultant mixture was stirred for 17 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 1.2 parts of the compound represented by the above-mentioned formula (h), which is called as B4.

$^1$H-NMR (dimethylsulfoxide-$d_6$): δ (ppm) 7.74-7.60 (5H, m), 3.98 (3H, s)

$^{19}$F-NMR (dimethylsulfoxide-$d_6$): δ (ppm) −62.25, −99.50

MS (ESI (+) Spectrum): [M+Na]$^+$ 384.0 ($C_{11}H_8F_5NO_5S$=361.0)

Example 5

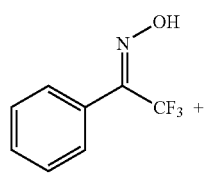

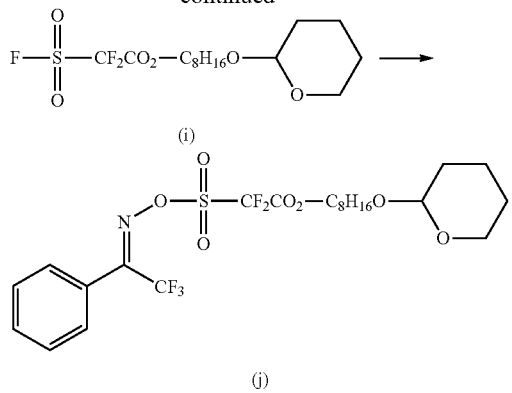

To the solution prepared by dissolving 1.0 parts of trifluoroacetophenone oxime in 0.9 parts of N,N-dimethylformamide, 0.7 part of 2,6-lutidine and 4.6 parts of the compound represented by the above-mentioned formula (i) were added. The resultant mixture was stirred for 18 hours at room temperature. The obtained reaction mixture was purified with silica gel chromatography to obtain 1.7 parts of the compound represented by the above-mentioned formula (j), which is called as B5.

$^1$H-NMR (dimethylsulfoxide-$d_6$): δ (ppm) 7.74-7.56 (5H, m) 4.54-4.46 (1H, m), 4.37 (2H, t, J=6.4 Hz), 3.76-3.65 (1H, m), 3.64-3.51 (1H, m), 3.45-3.20 (2H, m), 1.76-1.13 (18H, m)

Example 6

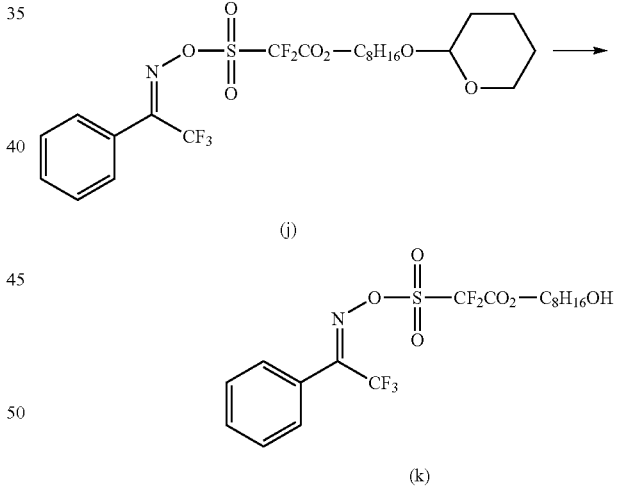

To 1 part of methanol, 0.5 part of the compound represented by the above-mentioned formula (j) was added to prepare a solution. To the resultant solution, 0.01 part of p-toluenesulfonic acid monohydrate was added. The resultant mixture was stirred for 6 hours at room temperature. The obtained reaction mixture was mixed with 10 parts of methanol and 10 parts of heptane. The methanol layer was obtained by separation. To the methanol layer, 3 parts of ion-exchanged water was added followed by extracting with ethyl acetate. The obtained organic layer was washed and then concentrated under reduced pressure to obtain 0.3 part of the compound represented by the above-mentioned formula (k) which is called as B6.

¹H-NMR (dimethylsulfoxide-d₆): δ (ppm) 7.74-7.55 (5H, m), 4.37 (3H, t, J=6.3 Hz), 3.40-3.23 (2H, m), 1.65-1.12 (12H, m)

Example 7

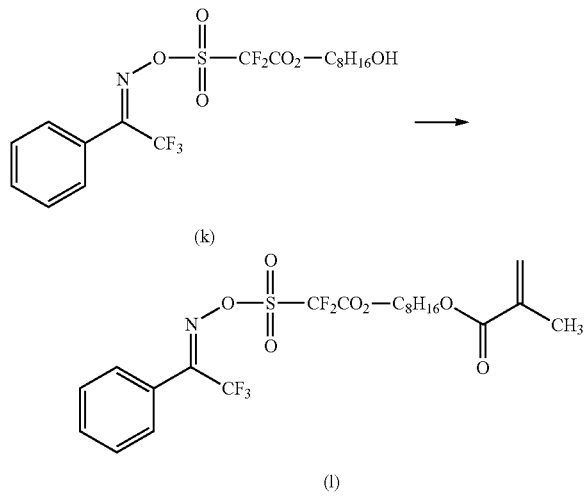

To the solution prepared by dissolving 0.3 part of the compound represented by the above-mentioned formula (k) in 2.3 parts of tetrahydrofuran, 0.2 part of 2,6-lutidine and 0.2 part of methacryloyl chloride were added. The resultant mixture was stirred for 1 hour at 0° C. The obtained reaction mixture was purified with silica gel chromatography to obtain 0.3 part of the compound represented by the above-mentioned formula (l) which is called as B7.

¹H-NMR (dimethylsulfoxide-d₆): δ (ppm) 7.73-7.54 (5H, m), 6.02-5.98 (1H, m), 5.66-5.62 (1H, m), 4.37 (2H, t, J=6.4 Hz), 4.17-3.91 (2H, m), 1.94-1.90 (3H, m), 1.65-1.17 (12H, m)

Example 8

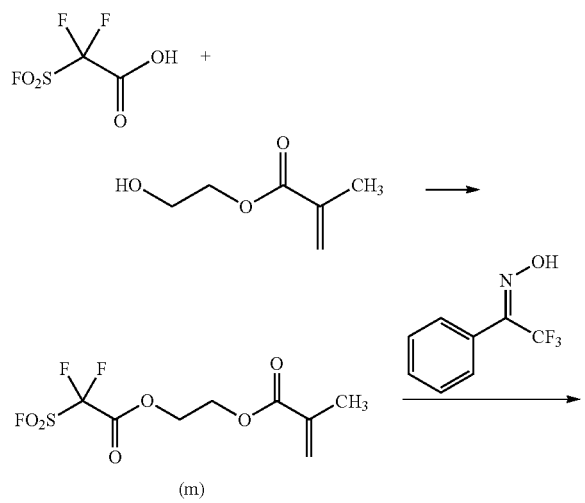

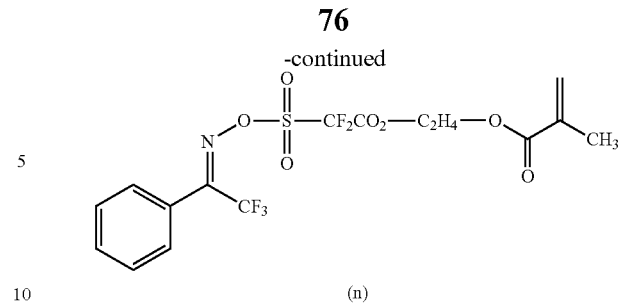

(n)

(1) To the solution prepared by mixing 5 parts of difluoro(fluorosulfonyl)acetic acid and 66 parts of dichloroethane, 4.4 parts of 2-hydroxyethyl methacrylate, 0.05 part of sulfuric acid and 0.01 part of p-methoxyphenol were added and the resultant mixture was stirred for 1 hour under reflux. The obtained reaction mixture was cooled to room temperature and 80 parts of ion-exchanged water was added thereto followed by extracting with 200 parts of chloroform. The obtained organic layer was washed three times with water and then concentrated under reduced pressure to obtain 8.4 parts of the compound represented by the above-mentioned formula (m).

¹H-NMR (dimethylsulfoxide-d₆): δ (ppm) 6.03 (1H, d, J=1.5 Hz), 5.73-5.70 (1H, m), 4.77 (2H, t, J=4.6 Hz), 4.43 (2H, t, J=4.6 Hz), 1.87 (3H, s)

¹⁹F-NMR (dimethylsulfoxide-d₆): δ (ppm) −45.03, −99.46

(2) To the solution prepared by dissolving 1.5 parts of trifluoroacetophenone oxime in 2.5 parts of N,N-dimethylformamide, 0.9 part of 2,6-lutidine and 3.1 parts of the compound represented by the above-mentioned formula (m) were added. The resultant mixture was stirred for 18 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 3.0 parts of the compound represented by the above-mentioned formula (n), which is called as B8.

¹H-NMR (dimethylsulfoxide-d₆): δ (ppm) 7.74-7.59 (5H, m), 6.03 (1H, s), 5.67-5.66 (1H, m), 4.72-4.69 (2H, m), 4.41-4.38 (2H, m), 1.85 (3H, s)

¹⁹F-NMR (dimethylsulfoxide-d₆): δ (ppm) −99.65, −62.33

Example 9

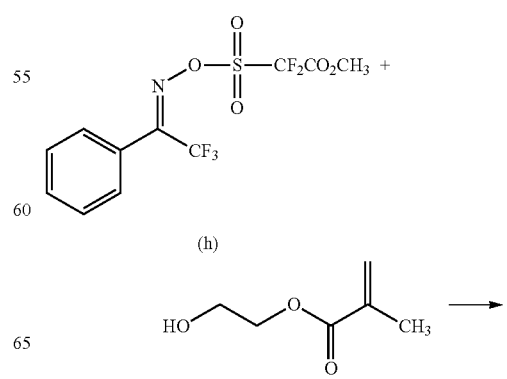

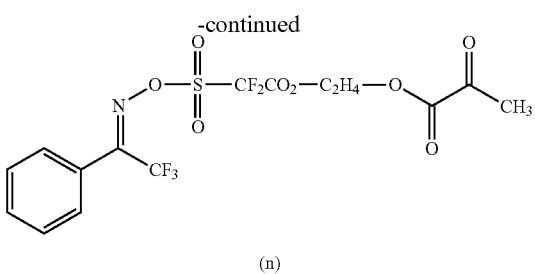

(n)

To the solution prepared by mixing 10 parts of the compound represented by the above-mentioned formula (h) and 50 parts of chloroform, 3.5 parts of 2-hydroxyethyl methacrylate, 0.01 part of p-methoxyphenol and 0.76 part of titanium tetraisopropoxide were added. The resultant mixture was stirred for 40 hours under reflux. The obtained reaction mixture was cooled to room temperature and 6 parts of silica gel was added thereto. The resultant mixture was stirred for 30 minutes, and then filtrated. The obtained filtrate was concentrated under reduced pressure. To the obtained residue, n-heptane and ion-exchanged water were added to conduct extraction. The obtained organic layer was washed three times with ion-exchanged water and then concentrated under reduced pressure to obtain 8.6 parts of the compound represented by the above-mentioned formula (n).

Example 10

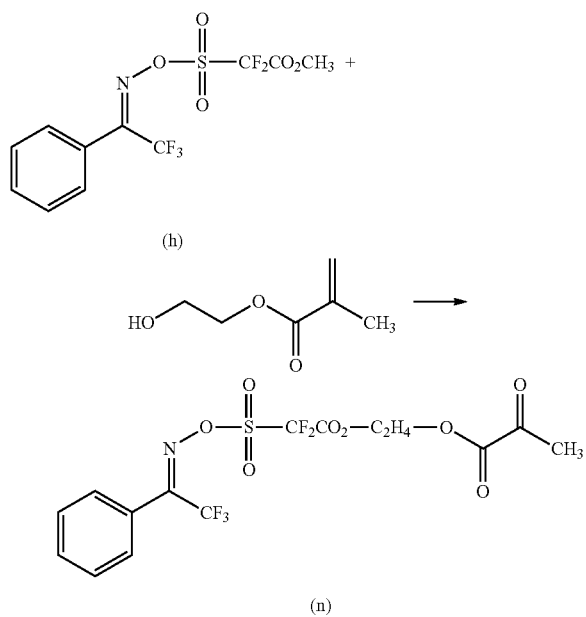

To the solution prepared by mixing 30 parts of the compound represented by the above-mentioned formula (h) and 150 parts of chloroform, 12.15 parts of 2-hydroxyethyl methacrylate, 0.04 part of p-methoxyphenol and 1.27 part of samarium triisopropoxide were added. The resultant mixture was stirred for 23 hours under reflux. The obtained reaction mixture was cooled to room temperature and 12 parts of silica gel was added thereto. The resultant mixture was stirred for 30 minutes, and then filtrated. The obtained filtrate was concentrated under reduced pressure. To the obtained residue, n-heptane and ion-exchanged water were added to conduct extraction. The obtained organic layer was washed three times with ion-exchanged water and then concentrated under reduced pressure to obtain 25.5 parts of the compound represented by the above-mentioned formula (n).

Example 11

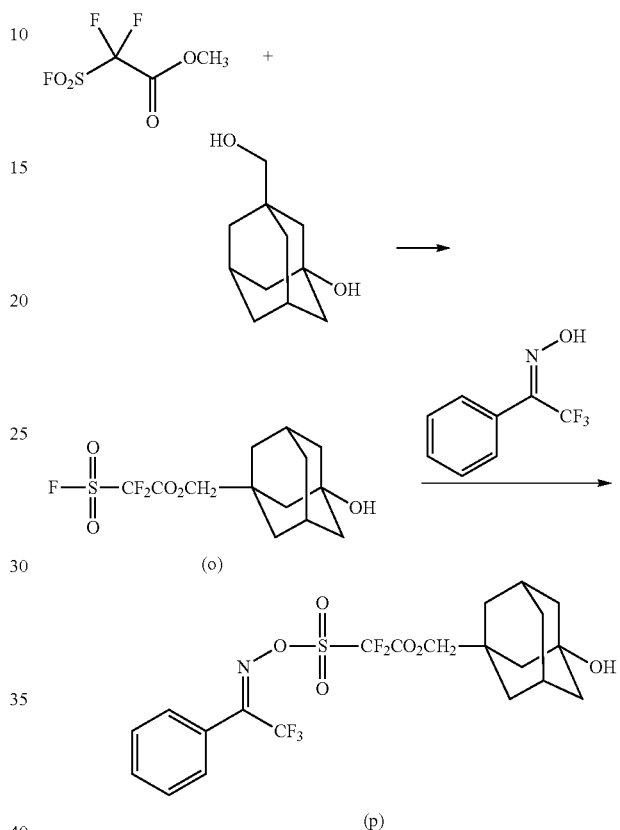

(1) To the solution prepared by mixing 5.27 parts of methyl difluoro (fluorosulfonyl)acetate and 25 parts of dichloroethane, 5.0 parts of 3-hydroxyadamantanemethanol and 0.34 part of titanium tetraisopropoxide were added and the resultant mixture was stirred for 5 hours under reflux. The obtained reaction mixture was cooled to room temperature and 80 parts of ion-exchanged water was added thereto followed by extracting with 200 parts of chloroform. The obtained organic layer was washed three times with water and then concentrated under reduced pressure to obtain 7.8 parts of the compound represented by the above-mentioned formula (o).

$^1$H-NMR (dimethylsulfoxide-$d_6$) δ (ppm) 4.15 (2H, s), 2.17-2.05 (2H, m), 1.63-1.26 (13H, m)

(2) To the solution prepared by dissolving 1.5 parts of trifluoroacetophenone oxime in 2.5 parts of N,N-dimethylformamide, 1.18 part of 2,6-lutidine and 3.64 parts of the compound represented by the above-mentioned formula (o) were added. The resultant mixture was stirred for 10 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 5.2 parts of the compound represented by the above-mentioned formula (p), which is called as B9.

$^1$H-NMR (dimethylsulfoxide-d$_6$): δ (ppm) 7.73-7.59 (5H, m) 4.46 (1H, brs), 4.05 (2H, s), 2.08 (2H, s), 1.56-1.31 (12H, m)

$^{19}$F-NMR (dimethylsulfoxide-d$_6$): δ (ppm) −99.11, −62.05

Example 12

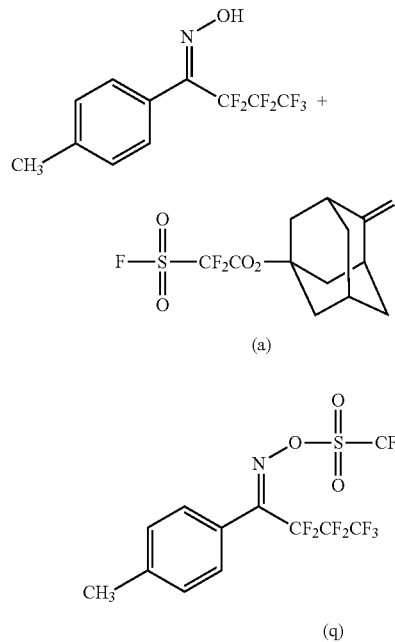

To the solution prepared by dissolving 2.0 parts of 1-(p-tolyl)heptafluorobutanone oxime in 2.5 parts of N,N-dimethylformamide, 0.8 part of 2,6-lutidine and 2.5 parts of the compound represented by the above-mentioned formula (a) were added. The resultant mixture was stirred for 10 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 1.3 parts of the compound represented by the above-mentioned formula (q), which is called as B10.

$^1$H-NMR (dimethylsulfoxide-d$_6$): δ (ppm) 7.46 (4H, s), 2.54 (2H, brs), 2.41 (3H, s), 2.34-2.21 (7H, m), 2.02-1.95 (2H, m), 1.88-1.81 (2H, m)

$^{19}$F-NMR (dimethylsulfoxide-d$_6$): δ (ppm) −120.02, −106.46, −99.26, −75.54

Example 13

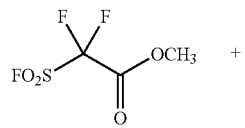

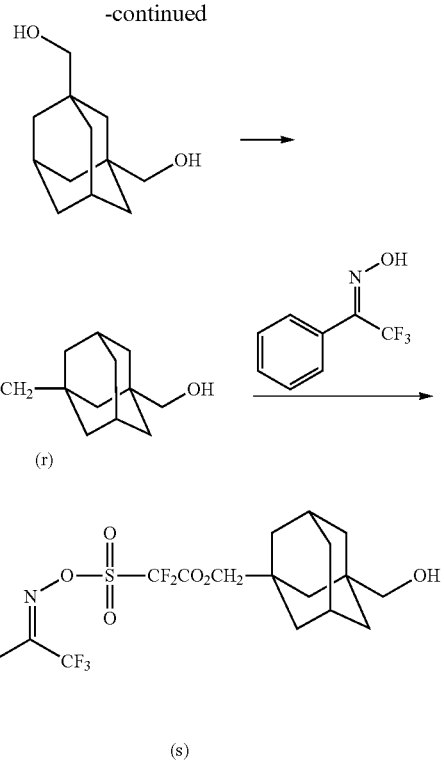

(1) To the solution prepared by mixing 5.27 parts of methyl difluoro(fluorosulfonyl)acetate and 25 parts of dichloroethane, 5.0 parts of 3-(hydroxymethyl)adamantanemethanol and 0.34 part of titanium tetraisopropoxide were added and the resultant mixture was stirred for 5 hours under reflux. The obtained reaction mixture was cooled to room temperature and 80 parts of ion-exchanged water was added thereto followed by extracting with 200 parts of chloroform. The obtained organic layer was washed three times with water and then concentrated under reduced pressure to obtain 7.8 parts of the compound represented by the above-mentioned formula (r).

$^1$H-NMR (dimethylsulfoxide-d$_6$): δ (ppm) 4.14 (2H, d, J=4.29 Hz), 2.99 (2H, s), 2.10-1.96 (2H, m), 1.61-1.17 (12H, m)

(2) To the solution prepared by dissolving 1.5 parts of trifluoroacetophenone oxime in 2.5 parts of N,N-dimethylformamide, 1.18 part of 2,6-lutidine and 3.64 parts of the compound represented by the above-mentioned formula (r) were added. The resultant mixture was stirred for 10 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 5.2 parts of the compound represented by the above-mentioned formula (s) which is called as B11.

$^1$H-NMR (dimethylsulfoxide-d$_6$): δ (ppm) 7.75-7.54 (5H, m), 4.37 (1H, t, J=5.44 Hz), 4.02 (2H, s), 2.97 (2H, d, J=5.28 Hz), 2.02-1.93 (2H, m), 1.57-1.17 (12H, m)

Example 14

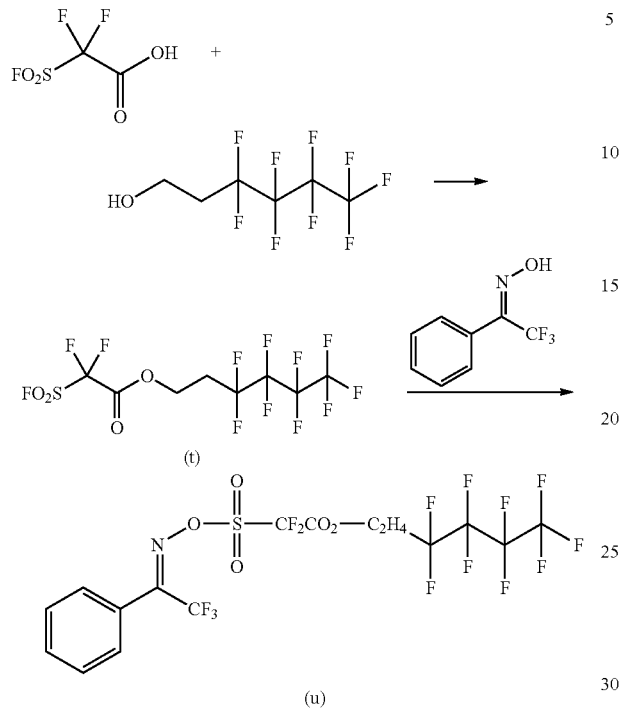

(1) To the solution prepared by mixing 3 parts of difluoro(fluorosulfonyl)acetic acid and 26 parts of dichloroethane, 3.9 parts of 3,3,4,4,5,5,6,6,6-nonafluorohexanol and 0.03 part of sulfuric acid were added and the resultant mixture was stirred for 2 hours under reflux. The obtained reaction mixture was cooled to room temperature and 100 parts of ion-exchanged water was added thereto followed by extracting with 100 parts of chloroform. The obtained organic layer was washed three times with water and then concentrated under reduced pressure to obtain 5.3 parts of the compound represented by the above-mentioned formula (t)

$^1$H-NMR (dimethylsulfoxide-$d_6$): δ (ppm) 4.80 (2H, t, J=5.7 Hz), 2.85 (2H, tt, J=19.1 Hz, 5.5 Hz)

$^{19}$F-NMR (dimethylsulfoxide-$d_6$): δ (ppm) −121.85, −120.29, −99.59, −76.78

(2) To the solution prepared by dissolving 1.5 parts of trifluoroacetophenone oxime in 2.5 parts of N,N-dimethylformamide, 0.9 part of 2,6-lutidine and 3.7 parts of the compound represented by the above-mentioned formula (t) were added. The resultant mixture was stirred for 18 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 3.0 parts of the compound represented by the above-mentioned formula (u), which is called as B12.

$^1$H-NMR (dimethylsulfoxide-$d_6$): δ (ppm) 7.74-7.54 (5H, m), 4.69 (2H, t, J=5.60 Hz), 2.79 (2H, tt, J=19.12 Hz, 5.66 Hz)

$^{19}$F-NMR (dimethylsulfoxide-$d_6$) δ (ppm) −121.82, −120.21, −109.22, −99.83, −76.72, −62.43

Example 15

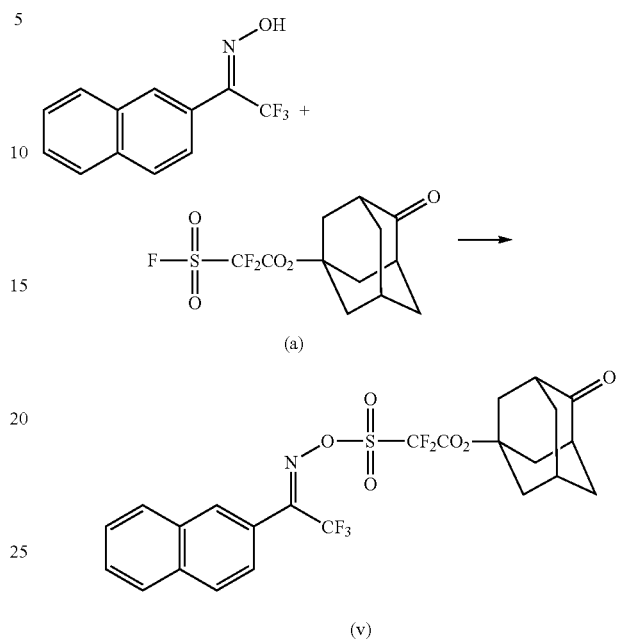

To the solution prepared by dissolving 4.0 parts of 2-trifluoroacetonaphthone oxime in 12 parts of N,N-dimethylformamide, 2.2 parts of 2,6-lutidine and 7.4 parts of the compound represented by the above-mentioned formula (a) were added. The resultant mixture was stirred for 16 hours at room temperature. To the obtained reaction mixture, a saturated aqueous ammonium chloride solution was added, and then the resultant mixture was extracted with ethyl acetate. The obtained organic layer was washed with ion-exchanged water and then concentrated under reduced pressure. The obtained residue was purified with silica gel chromatography to obtain 4.5 parts of the compound represented by the above-mentioned formula (v), which is called as B13.

$^1$H-NMR (dimethylsulfoxide-$d_6$) δ (ppm) 8.32-7.46 (7H, m) 2.61-2.10 (9H, s), 2.08-1.90 (2H, m), 1.89-1.72 (2H, m)

Example 16

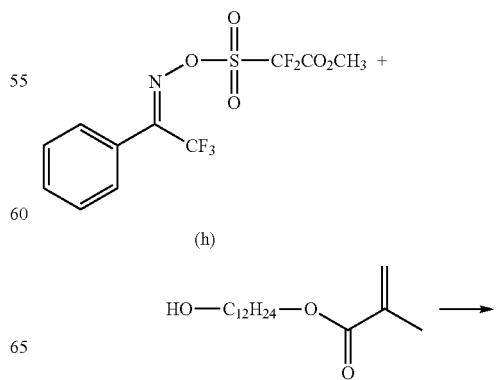

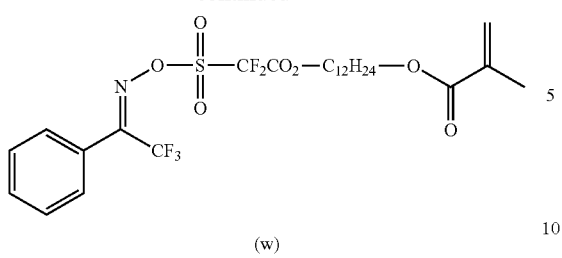

(w)

To the solution prepared by mixing 5 parts of the compound represented by the above-mentioned formula (h) and 25 parts of chloroform, 4.3 parts of 12-hydroxydodecyl methacrylate, 0.01 part of p-methoxyphenol and 0.19 part of titanium tetraisopropoxide were added and the resultant mixture was stirred for 22 hours under reflux. The obtained reaction mixture was cooled to room temperature and 6 parts of silica gel was added thereto. The resultant mixture was mixed for 30 minutes and then filtrated. The obtained filtrate was concentrated under reduced pressure. To the obtained residue, n-heptane and ion-exchanged water were added to conduct extraction. The obtained organic layer was washed three times with ion-exchanged water and then concentrated under reduced pressure. The obtained residue was purified with silica gel chromatography to obtain 3.6 parts of the compound represented by the above-mentioned formula (w), which is called as B14.

$^{1}$H-NMR (dimethylsulfoxide-$d_6$): δ (ppm) 7.72-7.59 (5H, m), 6.10 (1H, s), 5.64 (1H, s), 4.39 (2H, t, J=6.5 Hz), 4.08 (2H, t. J=6.8 Hz), 1.88 (3H, s), 1.63-1.59 (4H, m), 1.39-1.18 (16H, m)

$^{19}$F-NMR (dimethylsulfoxide-$d_6$): δ (ppm) −62.31, −99.56

MS (ESI (+) Spectrum): [M+Na]$^+$ 622.1 ($C_{26}H_{34}F_5NO_7S$=599.1)

Monomers used in the following Examples are following monomers E1, E2, E3, E4, E5 and E6.

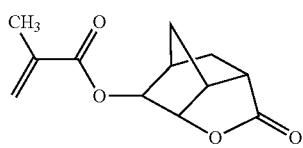

E1

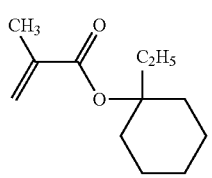

E2

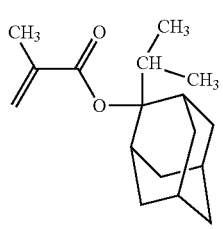

E3

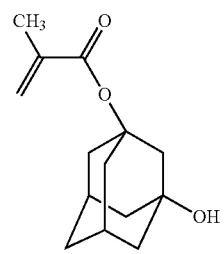

E4

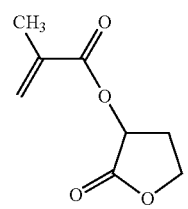

E5

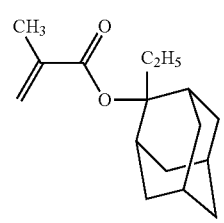

E6

Example 17

To a four-necked flask equipped with a condenser, a stirrer and a thermometer, 4.65 parts of 1,4-dioxane was added, and then heated to 77° C. A solution prepared by mixing 4.0 parts of B8, 1.7 parts of monomer E1, 0.02 part of 2,2'-azobisisobutyronitrile, 0.11 part of 2,2'-azobis(2,4-dimethylvaleronitrile) and 8.1 parts of 1,4-dioxane was added dropwise thereto over 2 hours. The resultant mixture was heated at 77° C. for 5 hours. The reaction mixture was cooled to room temperature and then pored into a mixed solution of 13.3 parts of water and 53.1 parts of methanol to cause precipitation. The precipitate was isolated and washed with methanol followed by drying under reduced pressure to obtain a resin having a weight-average molecular weight of 9,600 and degree of dispersion (Mw/Mn) of 2.6. This resin had the following structural units. This is called as resin D1.

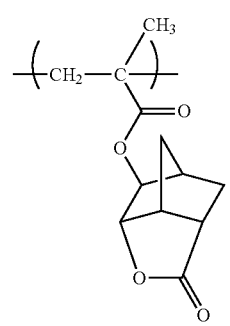

-continued

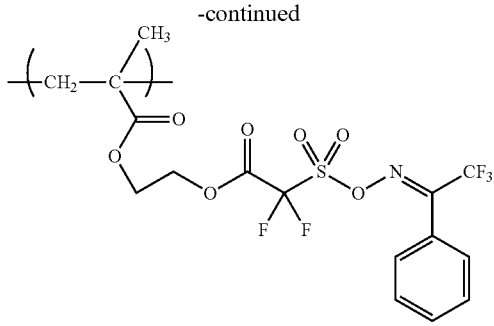

Example 18

To a four-necked flask equipped with a condenser, a stirrer and a thermometer, 7.4 parts of 1,4-dioxane was added, and then heated to 77° C. A solution prepared by mixing 4.5 parts of B8, 4.1 parts of monomer E2, 0.05 part of 2,2'-azobisisobutyronitrile, 0.22 part of 2,2'-azobis(2,4-dimethylvaleronitrile) and 4.6 parts of 1,4-dioxane was added dropwise thereto over 2 hours. The resultant mixture was heated at 77° C. for 5 hours. The reaction mixture was cooled to room temperature and then pored into a mixed solution of 21.5 parts of water and 85.9 parts of methanol to cause precipitation. The precipitate was isolated and washed with methanol followed by drying under reduced pressure to obtain a resin having a weight-average molecular weight of 6,800 and degree of dispersion (Mw/Mn) of 1.7. This resin had the following structural units. This is called as resin D2.

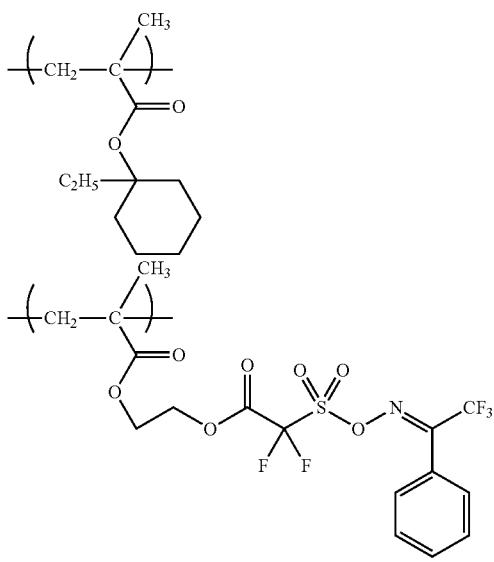

Example 19

To a four-necked flask equipped with a condenser, a stirrer and a thermometer, 3.9 parts of 1,4-dioxane was added, and then heated to 72° C. A solution prepared by mixing 5.7 parts of B8, 7.4 parts of monomer E2, 0.08 part of 2,2'-azobisisobutyronitrile, 0.37 part of 2,2'-azobis(2,4-dimethylvaleronitrile) and 15.7 parts of 1,4-dioxane was added dropwise thereto over 2 hours. The resultant mixture was heated at 72° C. for 5 hours. The reaction mixture was cooled to room temperature and then pored into a mixed solution of 34 parts of water and 136 parts of methanol to cause precipitation. The precipitate was isolated and washed with methanol followed by drying under reduced pressure to obtain a resin having a weight-average molecular weight of 12,000 and degree of dispersion (Mw/Mn) of 1.8. This resin had the following structural units. This is called as resin D3.

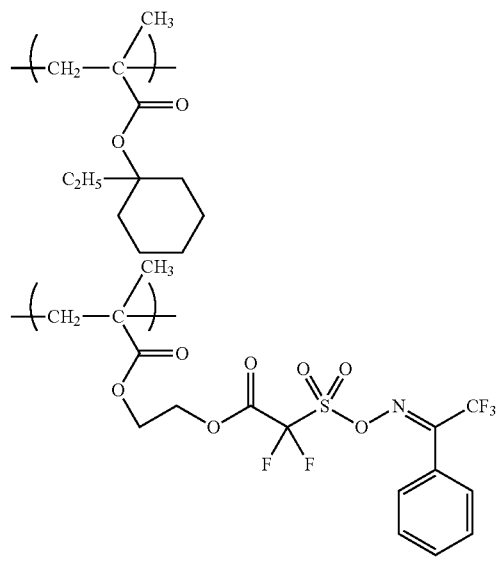

Example 20

To a four-necked flask equipped with a condenser, a stirrer and a thermometer, 3.9 parts of 1,4-dioxane was added, and then heated to 68° C. A solution prepared by mixing 9.2 parts of B8, 3.9 parts of monomer E2, 0.04 part of 2,2'-azobisisobutyronitrile, 0.16 part of 2,2'-azobis(2,4-dimethylvaleronitrile) and 15.7 parts of 1,4-dioxane was added dropwise thereto over 2 hours. The resultant mixture was heated at 68° C. for 5 hours. The reaction mixture was cooled to room temperature and then pored into a mixed solution of 34 parts of water and 136 parts of methanol to cause precipitation. The precipitate was isolated and washed with methanol followed by drying under reduced pressure to obtain a resin having a weight-average molecular weight of 31,000 and degree of dispersion (Mw/Mn) of 2.1. This resin had the following structural units. This is called as resin D4.

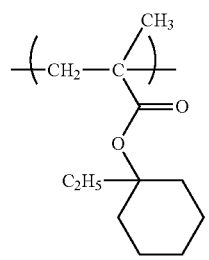

-continued

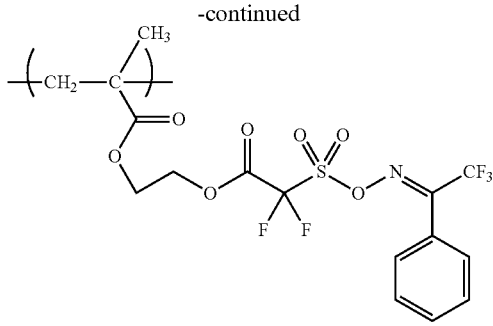

Example 21

To a four-necked flask equipped with a condenser, a stirrer and a thermometer, 3.5 parts of 1,4-dioxane was added, and then heated to 76° C. A solution prepared by mixing 10.3 parts of B8, 1.5 parts of monomer E2, 0.1 part of 2,2'-azobisisobutyronitrile, 0.45 part of 2,2'-azobis(2,4-dimethylvaleronitrile) and 14.2 parts of 1,4-dioxane was added dropwise thereto over 2 hours. The resultant mixture was heated at 76° C. for 5 hours. The reaction mixture was cooled to room temperature and then pored into a mixed solution of 31 parts of water and 123 parts of methanol to cause precipitation. The precipitate was isolated and washed with methanol followed by drying under reduced pressure to obtain a resin having a weight-average molecular weight of 12,000 and degree of dispersion (Mw/Mn) of 1.9. This resin had the following structural units. This is called as resin D5.

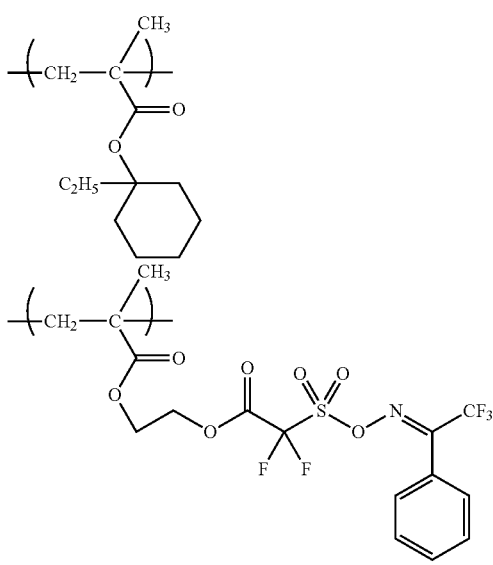

Example 22

To a four-necked flask equipped with a condenser, a stirrer and a thermometer, 8.3 parts of 1,4-dioxane was added, and then heated to 72° C. A solution prepared by mixing 27.6 parts of B8, 0.1 part of 2,2'-azobisisobutyronitrile, 0.45 part of 2,2'-azobis(2,4-dimethylvaleronitrile) and 33.1 parts of 1,4-dioxane was added dropwise thereto over 2 hours. The resultant mixture was heated at 72° C. for 5 hours. The reaction mixture was cooled to room temperature and then pored into a mixed solution of 72 parts of water and 287 parts of methanol to cause precipitation. The precipitate was isolated and washed with methanol followed by drying under reduced pressure to obtain a resin having a weight-average molecular weight of 22,000 and degree of dispersion (Mw/Mn) of 2.1. This resin had the following structural unit. This is called as resin D6.

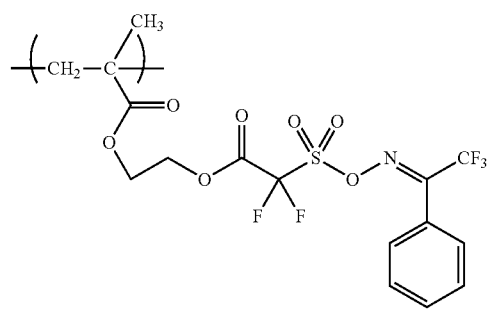

Example 23

To a four-necked flask equipped with a condenser, a stirrer and a thermometer, 7.5 parts of 1,4-dioxane was added, and then heated to 68° C. A solution prepared by mixing 4.5 parts of B8, 7.9 parts of monomer E3, 0.02 part of 2,2'-azobisisobutyronitrile, 0.09 part of 2,2'-azobis(2,4-dimethylvaleronitrile) and 11.2 parts of 1,4-dioxane was added dropwise thereto over 2 hours. The resultant mixture was heated at 68° C. for 5 hours. The reaction mixture was cooled to room temperature and then pored into a mixed solution of 32 parts of water and 130 parts of methanol to cause precipitation. The precipitate was isolated and washed with methanol followed by drying under reduced pressure to obtain a resin having a weight-average molecular weight of 19,000 and degree of dispersion (Mw/Mn) of 1.9. This resin had the following structural units. This is called as resin D7.

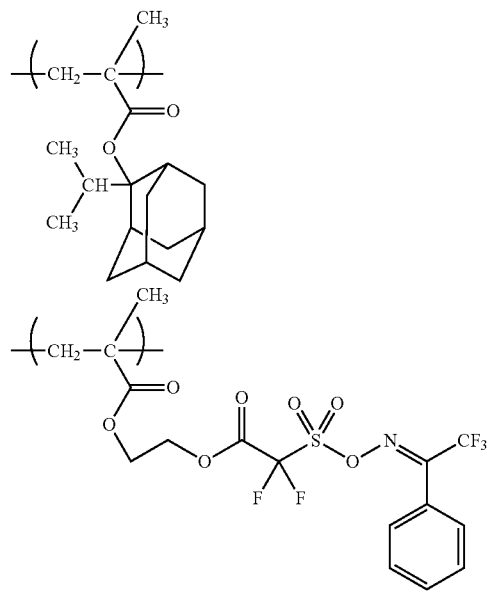

Example 24

To a four-necked flask equipped with a condenser, a stirrer and a thermometer, 7.9 parts of 1,4-dioxane was added, and then heated to 73° C. A solution prepared by mixing 3.0 parts of B8, 4.0 parts of monomer E6, 0.7 parts of monomer E2, 2.1 parts of monomer E4, 3.7 parts of monomer E5, 0.09 part of 2,2'-azobisisobutyronitrile, 0.41 part of 2,2'-azobis(2,4-dimethylvaleronitrile) and 7.9 parts of 1,4-dioxane was added dropwise thereto over 2 hours. The resultant mixture was heated at 73° C. for 5 hours. The reaction mixture was cooled to room temperature and then pored into a mixed solution of 34 parts of water and 137 parts of methanol to cause precipitation. The precipitate was isolated and washed with methanol followed by drying under reduced pressure to obtain a resin having a weight-average molecular weight of 6,900 and degree of dispersion (Mw/Mn) of 2.2. This resin had the following structural units. This is called as resin D8.

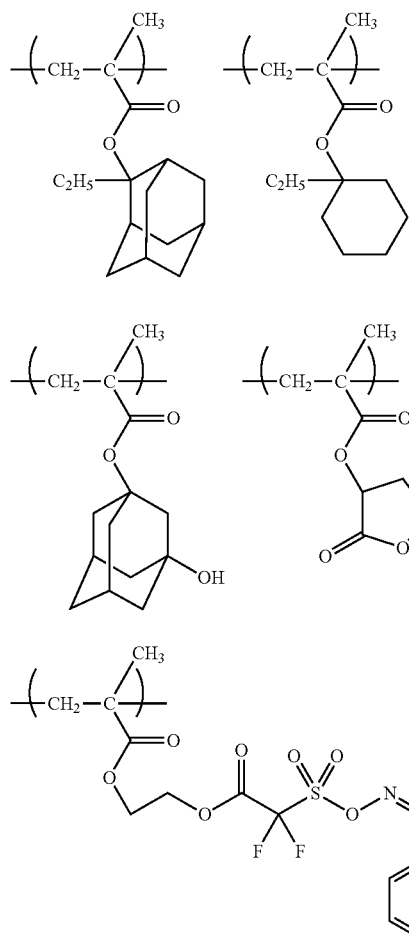

Example 25

A resin is prepared according to the same manner as that of Example 17, except that B14 is used in place of B8. This resin has the following structural units. This is called as resin D9.

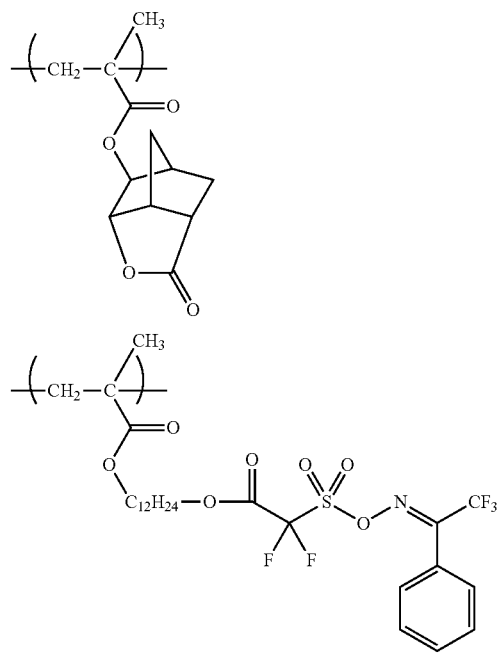

Example 26

A resin is prepared according to the same manner as that of Example 18, except that B14 is used in place of B8. This resin has the following structural units. This is called as resin D10.

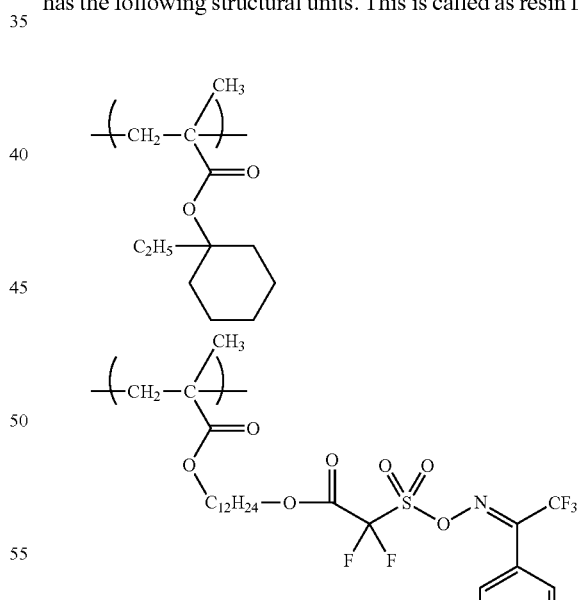

Example 27

A resin is prepared according to the same manner as that of Example 19, except that B14 is used in place of B8. This resin has the following structural units. This is called as resin D11.

Example 28

A resin is prepared according to the same manner as that of Example 20, except that B14 is used in place of B8. This resin has the following structural units. This is called as resin D12.

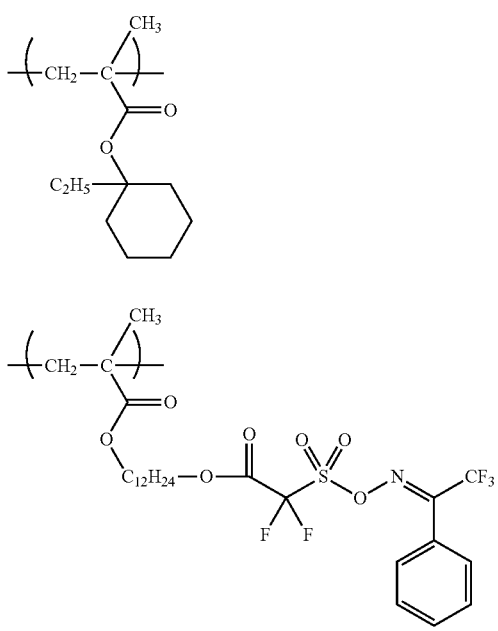

Example 29

A resin is prepared according to the same manner as that of Example 21 except that B14 is used in place of B8. This resin has the following structural units. This is called as resin D13.

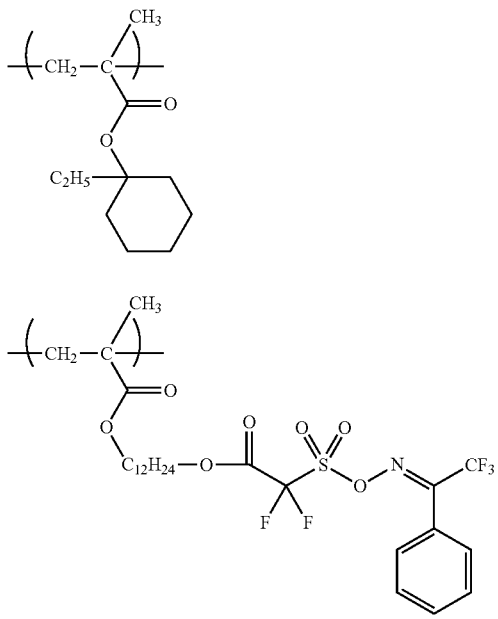

Example 30

A resin is prepared according to the same manner as that of Example 22, except that B14 is used in place of B8. This resin has the following structural unit. This is called as resin D14.

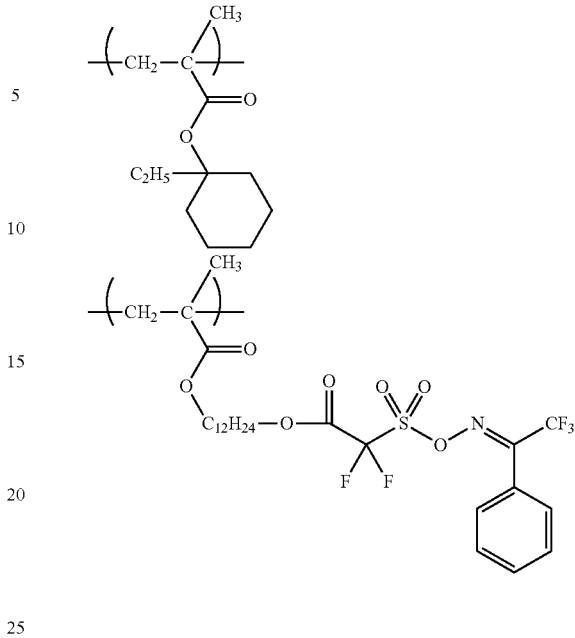

Example 31

A resin is prepared according to the same manner as that of Example 23, except that B14 is used in place of B8. This resin has the following structural units. This is called as resin D15.

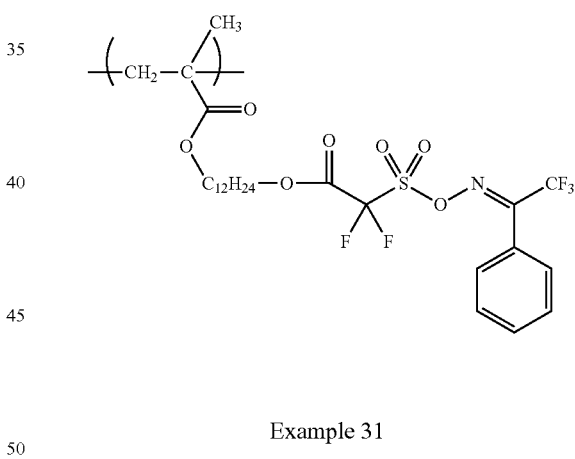
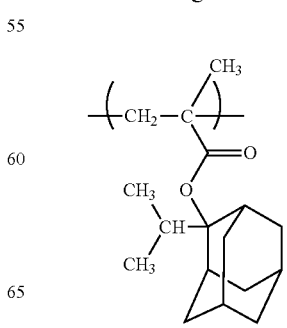

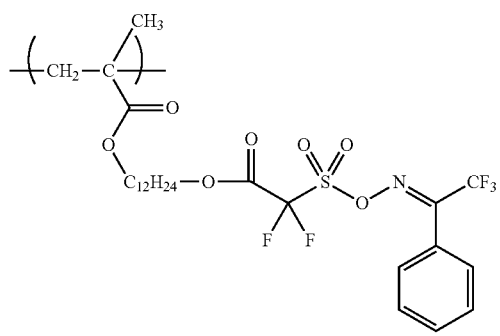

Example 32

A resin is prepared according to the same manner as that of Example 24, except that B14 is used in place of B8. This resin has the following structural units. This is called as resin D16.

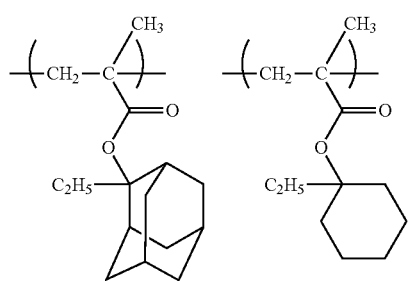

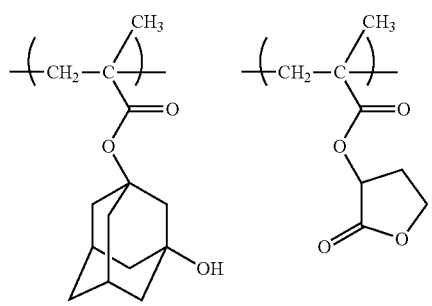

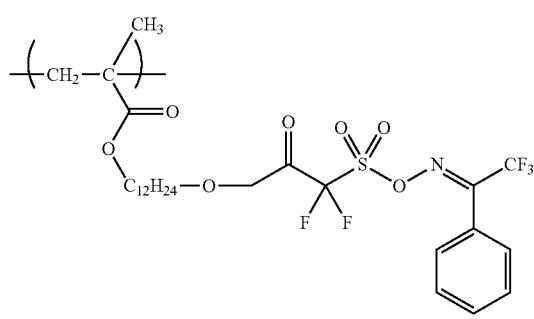

Example 33

A resin is prepared according to the same manner as that of Example 17, except that B7 is used in place of B8. This resin has the following structural units. This is called as resin D17.

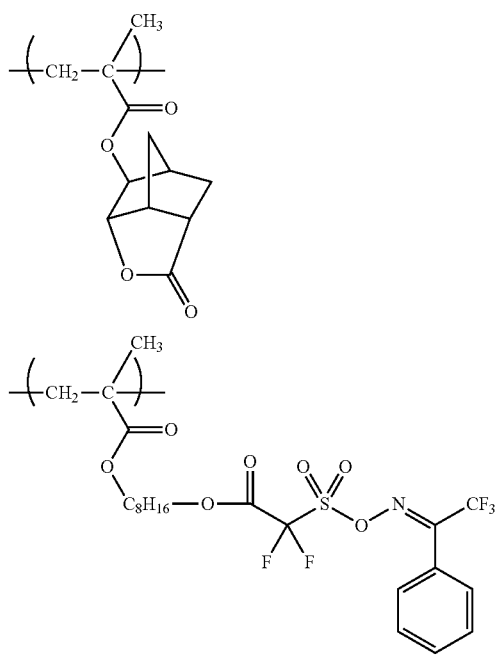

Example 34

A resin is prepared according to the same manner as that of Example 18, except that B7 is used in place of B8. This resin has the following structural units. This is called as resin D18.

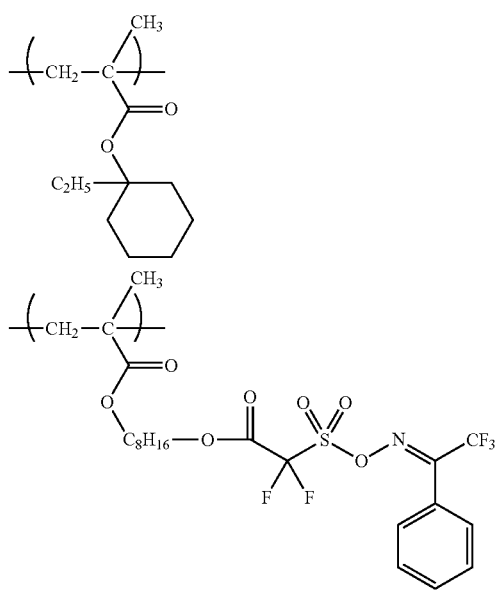

Example 35

A resin is prepared according to the same manner as that of Example 19, except that B7 is used in place of B8. This resin has the following structural units. This is called as resin D19.

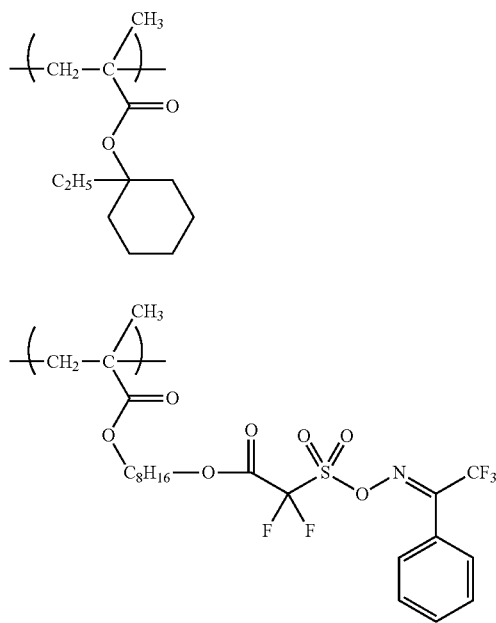

Example 36

A resin is prepared according to the same manner as that of Example 20, except that B7 is used in place of B8. This resin has the following structural units. This is called as resin D20.

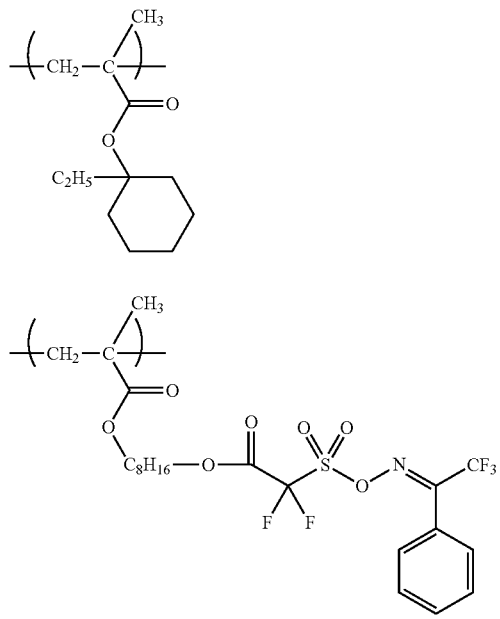

Example 37

A resin is prepared according to the same manner as that of Example 21, except that B7 is used in place of B8. This resin has the following structural units. This is called as resin D21.

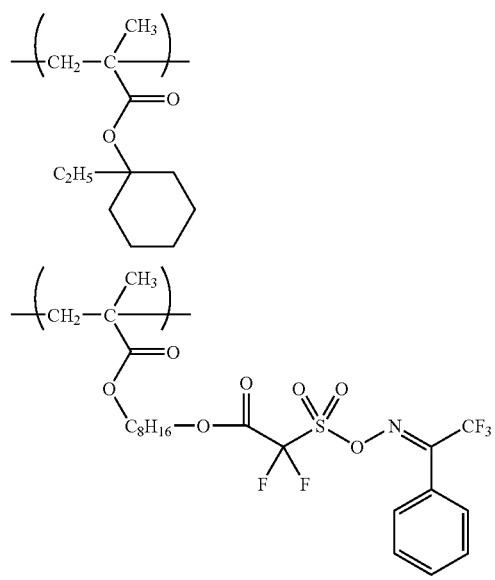

Example 38

A resin is prepared according to the same manner as that of Example 22, except that B7 is used in place of B8. This resin has the following structural units. This is called as resin D22.

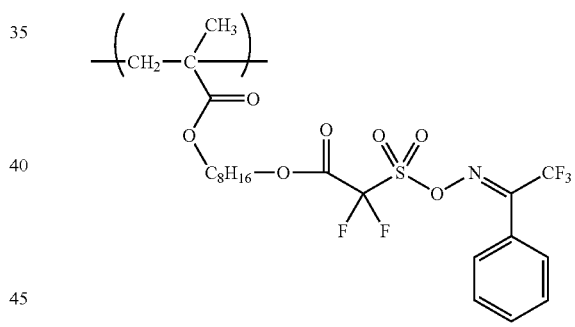

Example 39

A resin is prepared according to the same manner as that of Example 23, except that B7 is used in place of B8. This resin has the following structural units. This is called as resin D23.

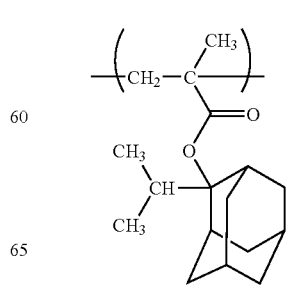

-continued

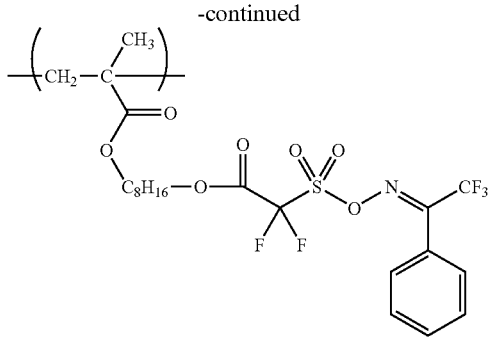

Example 40

A resin is prepared according to the same manner as that of Example 24, except that 37 is used in place of B8. This resin has the following structural units. This is called as resin D24.

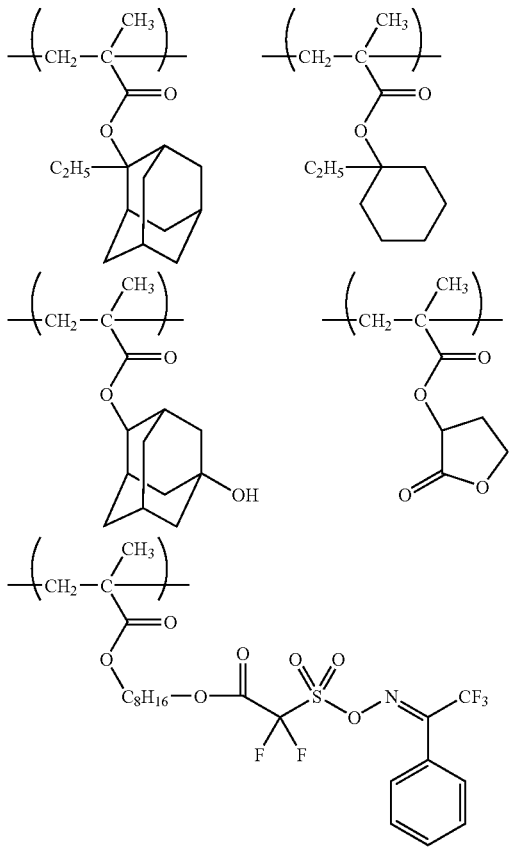

Reference Resin Synthesis Example 1

To a four-necked flask equipped with a condenser, a stirrer and a thermometer, 25.3 parts of 1,4-dioxane was added, and then heated to 75° C. A solution prepared by mixing 7.9 parts of monomer E6, 15.1 parts of monomer E4, 5.1 parts of monomer E5, 0.16 part of 2,2'-azobisisobutyronitrile, 0.75 part of 2,2'-azobis(2,4-dimethylvaleronitrile) and 16.9 parts of 1,4-dioxane was added dropwise thereto over 2 hours. The resultant mixture was heated at 75° C. for 5 hours. The reaction mixture was cooled to room temperature and then pored into a mixed solution of 73 parts of water and 292 parts of methanol to cause precipitation. The precipitate was isolated and washed with methanol followed by drying under reduced pressure to obtain a resin having a weight-average molecular weight of 9,200 and degree of dispersion (Mw/Mn) of 1.8. This resin had the following structural units. This is called as resin A1.

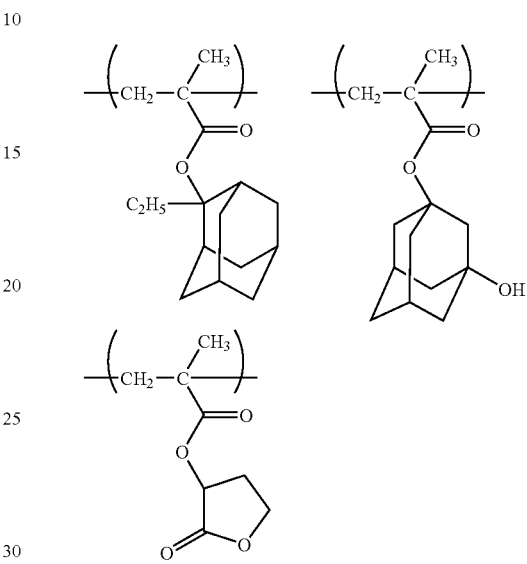

Reference Resin Synthetic Example 2

To a four-necked flask equipped with a condenser, a stirrer and a thermometer, 29.6 parts of 1,4-dioxane was added, and then heated to 73° C. A solution prepared by mixing 12.8 parts of monomer E1, 6.0 parts of monomer E2, 16.0 parts of monomer E3, 3.1 parts of monomer E4, 11.5 parts of monomer E5, 0.36 part of 2,2'-azobisisobutyronitrile, 1.62 parts of 2,2'-azobis(2,4-dimethylvaleronitrile) and 44.4 parts of 1,4-dioxane was added dropwise thereto over 2 hours. The resultant mixture was heated at 73° C. for 5 hours. The reaction mixture was cooled to room temperature and then pored into a mixed solution of 128 parts of water and 514 parts of methanol to cause precipitation. The precipitate was isolated and washed with methanol followed by drying under reduced pressure to obtain a resin having a weight-average molecular weight of 8,900 and degree of dispersion (Mw/Mn) of 1.6. This resin had the following structural units. This is called as resin A2.

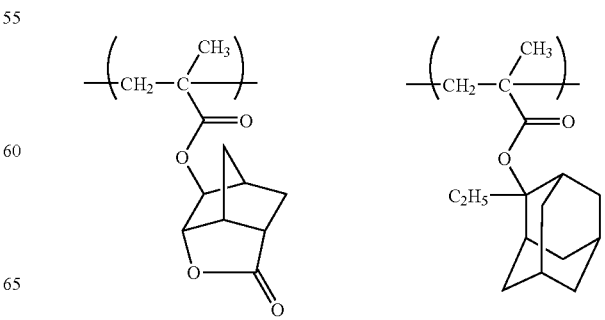

-continued

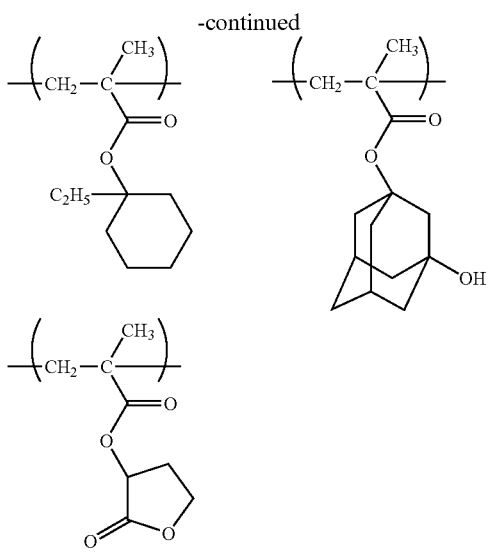

Examples 41 to 46 and Comparative Example 1

<Acid Generator>
B1, B2, B3, B4, B9, B10
C1:

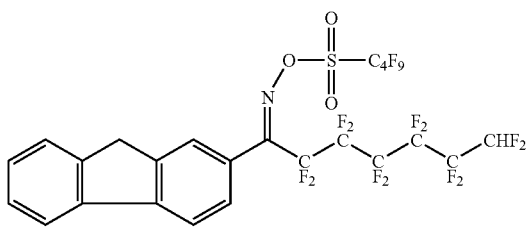

<Quencher>
Q1: 2,6-diisopropylaniline
<Solvent>

| Y1: | propylene glycol monomethyl ether acetate | 100 parts |
|---|---|---|
| | 2-heptanone | 20 parts |
| | Propylene glycol monomethyl ether | 20 parts |
| | γ-butyrolactone | 10 parts |

The following components were mixed and dissolved, further, filtrated through a fluorine resin filter having pore diameter of 0.2 μm, to prepare resist compositions.

Resin (kind and amount are described in Table 1)
Acid generator (kind and amount are described in Table 1)
Quencher (kind and amount are described in Table 1)
Solvent (kind is described in Table 1)

Silicon wafers were each coated with "ARC-29A-8", which is an organic anti-reflective coating composition available from Nissan Chemical Industries, Ltd., and then baked at 205° C. for 60 seconds, to form a 780 Å-thick organic anti-reflective coating. Each of the resist compositions prepared as above was spin-coated over the anti-reflective coating so that the thickness of the resulting film became 0.15 μm after drying. The silicon wafers thus coated with the respective resist liquids were each prebaked on a proximity hotplate at 100° C. for 60 seconds. Using an ArF excimer stepper ("FPA-5000AS3" manufactured by CANON INC., NA=0.75, 2/3 Annular), each wafer thus formed with the respective resist film was subjected to line and space pattern exposure, with the exposure quantity being varied stepwise.

After the exposure, each wafer was subjected to post-exposure baking on a hotplate at 100° C. for 60 seconds and then to paddle development for 15 seconds with an aqueous solution of 2.38 wt % tetramethylammonium hydroxide at 23° C.

Each of a dark field pattern developed on the organic anti-reflective coating substrate after the development was observed with a scanning electron microscope ("S-4100" manufactured by Hitachi, Ltd.), the results of which are shown in Table 2. The term "dark field pattern", as used herein, means a pattern obtained by exposure and development through a reticle comprising chromium base surface (light-shielding portion) and linear glass layers (light-transmitting portion) formed in the chromium surface and aligned with each other. Thus, the dark field pattern is such that, after exposure and development, resist layer surrounding the line and space pattern remains on substrate.

Effective Sensitivity (ES): It is expressed as the amount of exposure that the line pattern and the space pattern can be obtained.

Pattern Profile: Each of patterns developed on the organic anti-reflective coating substrate after the development, which was obtained at the amount of exposure of ES. When the cross-section shape of the pattern is rectangle, the pattern profile is good and its evaluation is marked by "○", and when the cross-section shape of the pattern is taper shape, the pattern profile is bad and its evaluation is marked by "X".

TABLE 1

| Ex. No. | Resin (kind/amount (part)) | Acid generator (kind/amount (part)) | Quencher (kind/amount (part)) | Solvent |
|---|---|---|---|---|
| Ex. 41 | A1/10 | B1/2.00 | Q1/0.01 | Y1 |
| Ex. 42 | A1/10 | B2/2.00 | Q1/0.01 | Y1 |
| Ex. 43 | A1/10 | B3/1.23 | Q1/0.01 | Y1 |
| Ex. 44 | A1/10 | B4/1.00 | Q1/0.01 | Y1 |
| Ex. 45 | A1/10 | B9/2.00 | Q1/0.01 | Y1 |
| Ex. 46 | A1/10 | B10/2.00 | Q1/0.01 | Y1 |
| Comp. Ex. 1 | A1/10 | C1/1.69 | Q1/0.03 | Y1 |

TABLE 2

| Ex. No. | Pattern Profile |
|---|---|
| Ex. 41 | ○ |
| Ex. 42 | ○ |
| Ex. 43 | ○ |
| Ex. 44 | ○ |
| Ex. 45 | ○ |
| Ex. 46 | ○ |
| Comp. Ex. 1 | X |

Example 47

The resist composition is prepared according to the same manner as that of Example 46, except that B5 is used as an acid generator in place of B1. The pattern is obtained according to the same manner as that of Example 46, except that the resist composition containing B5 is used in place of the resist composition containing B1.

Example 48

The resist composition is prepared according to the same manner as that of Example 46, except that B6 is used as an acid generator in place of B1. The pattern is obtained according to the same manner as that of Example 46, except that the resist composition containing B6 is used in place of the resist composition containing B1.

Example 49

The resist composition is prepared according to the same manner as that of Example 46, except that B7 is used as an acid generator in place of B1. The pattern is obtained according to the same manner as that of Example 46, except that the resist composition containing B7 is used in place of the resist composition containing B1.

Example 50

The resist composition is prepared according to the same manner as that of Example 46, except that B8 is used as an acid generator in place of B1. The pattern is obtained according to the same manner as that of Example 46, except that the resist composition containing B8 is used in place of the resist composition containing B1.

Example 51

The resist composition is prepared according to the same manner as that of Example 46, except that B11 is used as an acid generator in place of B1. The pattern is obtained according to the same manner as that of Example 46, except that the resist composition containing B11 is used in place of the resist composition containing B1.

Example 52

The resist composition is prepared according to the same manner as that of Example 46, except that B12 is used as an acid generator in place of B1. The pattern is obtained according to the same manner as that of Example 46, except that the resist composition containing B12 is used in place of the resist composition containing B1.

Example 53

The resist composition is prepared according to the same manner as that of Example 46, except that B13 is used as an acid generator in place of B1. The pattern is obtained according to the same manner as that of Example 46, except that the resist composition containing B13 is used in place of the resist composition containing B1.

Example 54

The resist composition is prepared according to the same manner as that of Example 46, except that B13 is used as an acid generator in place of E1. The pattern is obtained according to the same manner as that of Example 46, except that the resist composition containing B13 is used in place of the resist composition containing B1.

Example 55

Ten parts of resin A1 and 2 parts of resin D1 were dissolved in a mixture of 200 parts of propylene glycol monomethyl ether acetate, 35 parts of 2-heptanone and 3.5 parts of γ-butyrolactone. The obtained solution was filtrated through a fluorine resin filter having pore diameter of 0.2 μm, to prepare a resist composition.

A silicon wafer was coated with "ARC-29A-8", which is an organic anti-reflective coating composition available from Nissan Chemical Industries, Ltd., and then baked at 205° C. for 60 seconds, to form a 780 Å-thick organic anti-reflective coating. The resist composition prepared as above was spin-coated over the anti-reflective coating so that the thickness of the resulting film became 0.15 μm after drying. The silicon wafers thus coated with the respective resist liquids were each prebaked on a proximity hotplate at 125° C. for 60 seconds. Using an ArF excimer stepper ("FPA-5000AS3" manufactured by CANON INC., NA=0.75, 2/3 Annular), each wafer thus formed with the respective resist film was subjected to line and space pattern exposure, with the exposure quantity being varied stepwise.

After the exposure, each wafer was subjected to post-exposure baking on a hotplate at 125° C. for 60 seconds and then to paddle development for 15 seconds with an aqueous solution of 2.38 wt % tetramethylammonium hydroxide at 23° C.

A pattern developed on the organic anti-reflective coating substrate after the development was observed with a scanning electron microscope ("S-4100" manufactured by HITACHI, LTD.), and as the result, a resist pattern having a line width of 250 nm and a space width of 250 nm at an effective sensitivity of 50 mJ/cm² was observed.

Example 56

The resist composition is prepared according to the same manner as that of Example 55, except that resin D2 is used in place of resin D1. The pattern is obtained according to the same manner as that of Example 55, except that the resist composition containing resin D2 is used in place of the resist composition containing resin D1.

Example 57

The resist composition is prepared according to the same manner as that of Example 55, except that resin D3 is used in place of resin D1. The pattern is obtained according to the same manner as that of Example 55, except that the resist composition containing resin D3 is used in place of the resist composition containing resin D1.

In the following Examples, the acid generator C2 represented by the following formula was used.

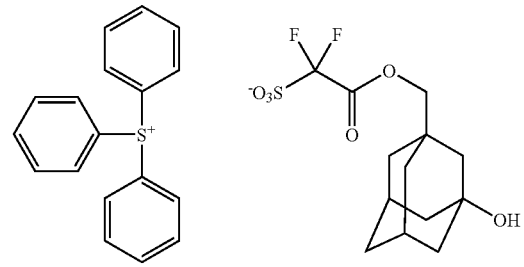

Example 58

Ten parts of resin A2, 0.6 part of resin D2, 1.5 parts of acid generator C2 and 0.122 part of 2,6-diisopropylaniline were dissolved in a mixture of 250 parts of propylene glycol monomethyl ether acetate, 20 parts of propylene glycol monomethyl ether, 35 parts of 2-heptanone and 3 parts of γ-butyrolactone. The obtained solution was filtrated through a fluorine resin filter having pore diameter of 0.2 μm, to prepare a resist composition.

A silicon wafer was coated with "ARC-29A-8", which is an organic anti-reflective coating composition available from Nissan Chemical Industries, Ltd., and then baked at 205° C. for 60 seconds, to form a 780 Å-thick organic anti-reflective coating. The resist composition prepared as above was spin-coated over the anti-reflective coating so that the thickness of the resulting film became 0.08 μm after drying. The silicon wafers thus coated with the respective resist liquids were each prebaked on a proximity hotplate at 85° C. for 60 seconds. Using an ArF excimer stepper ("FPA-5000AS3" manufactured by CANON INC., NA=0.75, 2/3 Annular), each wafer thus formed with the respective resist film was subjected to line and space pattern exposure, with the exposure quantity being varied stepwise.

After the exposure, each wafer was subjected to post-exposure baking on a hotplate at 85° C. for 60 seconds and then to paddle development for 15 seconds with an aqueous solution of 2.38 wt % tetramethylammonium hydroxide at 23° C.

A pattern developed on the organic anti-reflective coating substrate after the development was observed with a scanning electron microscope ("S-4100" manufactured by HITACHI, LTD.), and as the result, a resist pattern having a line width of 85 nm and a space width of 85 nm at an effective sensitivity of 31 mJ/cm$^2$ was observed.

Example 59

The resist composition was prepared according to the same manner as that of Example 58, except that resin D3 was used in place of resin D2. The resist pattern having a line width of 85 nm and a space width of 85 nm at an effective sensitivity of 30 mJ/cm$^2$ was obtained according to the same manner as that of Example 58, except that the resist composition containing resin D3 was used in place of the resist composition containing resin D2.

Example 60

The resist composition was prepared according to the same manner as that of Example 58, except that resin D5 was used in place of resin D2. The resist pattern having a line width of 85 nm and a space width of 85 nm at an effective sensitivity of 30 mJ/cm$^2$ was obtained according to the same manner as that of Example 58, except that the resist composition containing resin D5 was used in place of the resist composition containing resin D2.

Example 61

The resist composition was prepared according to the same manner as that of Example 58, except that resin D6 was used in place of resin D2. The resist pattern having a line width of 85 nm and a space width of 85 nm at an effective sensitivity of 30 mJ/cm$^2$ was obtained according to the same manner as that of Example 58, except that the resist composition containing resin D6 was used in place of the resist composition containing resin D2.

Example 62

The resist composition was prepared according to the same manner as that of Example 58, except that resin D7 was used in place of resin D2. The resist pattern having a line width of 85 nm and a space width of 85 nm at an effective sensitivity of 29 mJ/cm$^2$ was obtained according to the same manner as that of Example 58, except that the resist composition containing resin D7 was used in place of the resist composition containing resin D2.

Example 63

The resist composition is prepared according to the same manner as that of Example 58, except that resin D8, D9, D10, D11, D12, D13, D14, D15, D16, D17, D18, D19, D20, D21, D22, D23 or D24 is used in place of resin D2. The resist pattern can be obtained according to the same manner as that of Example 58, except that the resist composition containing resin D8, D9, D10, D11, D12, D13, D14, D15, D16, D17, D18, D19, D20, D21, D22, D23 or D24 is used in place of the resist composition containing resin D2.

Example 64

Ten parts of resin A2, 0.3 part of resin D3, 0.3 part of resin D6, 1.5 parts of acid generator C2 and 0.122 part of 2,6-diisopropylaniline were dissolved in a mixture of 250 parts of propylene glycol monomethyl ether acetate, 20 parts of propylene glycol monomethyl ether, 35 parts of 2-heptanone and 3 parts of γ-butyrolactone. The obtained solution was filtrated through a fluorine resin filter having pore diameter of 0.2 μm, to prepare a resist composition.

The resist pattern having a line width of 85 nm and a space width of 85 nm at an effective sensitivity of 30 mJ/cm$^2$ was obtained according to the same manner as that of Example 58, except that the resist composition containing resin D3 and resin D6 was used in place of the resist composition containing resin D2.

Example 65

Ten parts of resin A2, 0.5 part of resin D3, 1.5 parts of acid generator C2 and 0.055 part of 2,6-diisopropylaniline were dissolved in a mixture of 220 parts of propylene glycol monomethyl ether acetate, 20 parts of propylene glycol monomethyl ether, 35 parts of 2-heptanone and 3 parts of γ-butyrolactone. The obtained solution was filtrated through a fluorine resin filter having pore diameter of 0.2 μm, to prepare a resist composition.

A silicon wafer was coated with "ARC-29SR", which is an organic anti-reflective coating composition available from Nissan Chemical Industries, Ltd., and then baked at 205° C. for 60 seconds, to form a 930 Å-thick organic anti-reflective coating. The resist composition prepared as above was spin-coated over the anti-reflective coating so that the thickness of the resulting film became 100 nm after drying. The silicon wafer thus coated with the respective resist liquids was prebaked on a proximity hotplate at 115° C. for 60 seconds. Using an ArF excimer stepper ("XT:1900Gi" manufactured by ASML, NA=1.30, c-quad, σ OUTER=0.985, σ INNER=0.895), the wafer thus formed with the respective resist film was subjected to line and space pattern exposure, with the exposure quantity being varied stepwise.

After the exposure, the wafer was subjected to post-exposure baking on a hotplate at 85° C. for 60 seconds and then to paddle development for 21 seconds with an aqueous solution of 2.38 wt % tetramethylammonium hydroxide at 23° C.

A pattern developed on the organic anti-reflective coating substrate after the development was observed with a scanning electron microscope ("S-4800" manufactured by HITACHI, LTD.), and as the result, a resist pattern having a line width of 40 nm and a space width of 40 nm at an effective sensitivity of 23 mJ/cm² was observed.

Example 66

Ten parts of resin A2, 0.1 part of resin D4, 1.5 parts of acid generator C2 and 0.122 part of 2,6-diisopropylaniline were dissolved in a mixture of 275 parts of propylene glycol monomethyl ether acetate, 20 parts of propylene glycol monomethyl ether, 35 parts of 2-heptanone and 3 parts of γ-butyrolactone. The obtained solution was filtrated through a fluorine resin filter having pore diameter of 0.2 μm, to prepare a resist composition.

A silicon wafer was coated with "ARC-29SR", which is an organic anti-reflective coating composition available from Nissan Chemical Industries, Ltd., and then baked at 205° C. for 60 seconds, to form a 930 Å-thick organic anti-reflective coating. The resist composition prepared as above was spin-coated over the anti-reflective coating so that the thickness of the resulting film became 100 nm after drying. The silicon wafer thus coated with the respective resist liquids was pre-baked on a proximity hotplate at 85° C. for 60 seconds. Using an ArF excimer stepper ("XT:1900Gi" manufactured by ASML, NA=1.35, Annular, σ OUTER=0.9, σ INNER=0.675), the wafer thus formed with the respective resist film was subjected to line and space pattern exposure, with the exposure quantity being varied stepwise.

After the exposure, the wafer was subjected to post-exposure baking on a hotplate at 85° C. for 60 seconds and then to paddle development for 32 seconds with an aqueous solution of 2.38 wt % tetramethylammonium hydroxide at 23° C.

A pattern developed on the organic anti-reflective coating substrate after the development was observed with a scanning electron microscope ("S-4100" manufactured by HITACHI, LTD.), and as the result, a resist pattern having a line width of 50 nm and a space width of 50 nm at an effective sensitivity of 35 mJ/cm² was observed.

Example 67

The resist composition is prepared according to the same manner as that of Example 65, except that resin D1, D2, D5, D6, D7, D8, D9, D10, D11, D12, D13, D14, D15, D16, D17, D18, D19, D20, D21, D22, D23 or D24 is used in place of resin D3. The resist pattern can be obtained according to the same manner as that of Example 65, except that the resist composition containing resin D1, D2, D5, D6, D7, D8, D9, D10, D11, D12, D13, D14, D15, D16, D17, D18, D19, D20, D21, D22, D23 or D24 is used in place of the resist composition containing resin D3.

The present oxime compound and the present polymer are novel and are useful as an acid generator, and the present composition containing the present oxime compound or the present polymer provides a resist pattern having good pattern profile and is especially suitable for ArF excimer laser lithography, KrF excimer laser lithography and ArF immersion lithography.

What is claimed is:
1. An oxime compound represented by the formula (I):

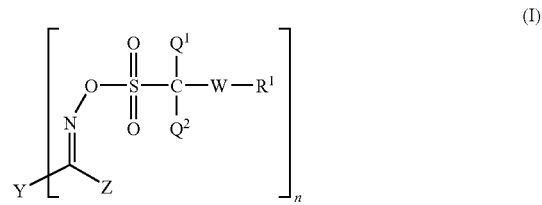

wherein Y represents an unsubstituted or substituted n-valent C6-C14 aromatic hydrocarbon group, n represents an integer of 1 to 6, $R^1$ represents a C1-C30 aliphatic hydrocarbon group, a C6-C14 aromatic hydrocarbon group, a C4-C10 heteroaromatic hydrocarbon group, a C1-C20 alkyl group having a C6-C14 aromatic hydrocarbon group or a C1-C20 alkyl group having a C4-C10 heteroaromatic hydrocarbon group, and one or more methylene groups in the aliphatic hydrocarbon groups may be replaced by —O—, —S—, —CO—, —CO—O—, —SO₂— or —N($R^c$)—, and the aliphatic hydrocarbon group, the aromatic hydrocarbon group, the heteroaromatic hydrocarbon group and the alkyl group may be respectively substituted with at least one selected from the group consisting of a hydroxyl group, an acryloyloxy group, a methacryloyloxy group, a halogen atom, a cyano group, —O$R^2$, —CO—O$R^2$, —O—CO—O$R^2$, —O—CO—$R^2$, —SO₂—O$R^2$, —O—SO₂—$R^2$ and —SO₂$R^2$, $R^2$ represents a linear or branched chain C1-C20 aliphatic hydrocarbon group in which one or more methylene groups may be replaced by —O—, —S—, —CO—, —CO—O— or —N($R^c$)—, and which may be substituted with at least one selected from the group consisting of a hydroxyl group, an acryloyloxy group and a methacryloyloxy group, $R^c$ represents a hydrogen atom or a linear or branched chain C1-C4 aliphatic hydrocarbon group, W represents —CO—O—, —CH₂O— or —CH₂O—CO—

$Q^1$ and $Q^2$ each independently represent a fluorine atom or a C1-C6 perfluoroalkyl group, Z represents a C1-C20 halogenated aliphatic hydrocarbon group, a C6-C14 halogenated aromatic hydrocarbon group, a cyano group, —CX₂—$R^1$ or —CX₂—SO₂—$R^1$, and X represents a halogen atom or a C1-C20 halogenated aliphatic hydrocarbon group.

2. The oxime compound according to claim 1, wherein n is 1.

3. The oxime compound according to claim 1, wherein the unsubstituted or substituted n-valent C6-C14 aromatic hydrocarbon group is an unsubstituted or substituted phenyl group, an unsubstituted or substituted naphthyl group, an unsubstituted or substituted biphenyl group, an unsubstituted or substituted anthryl group, an unsubstituted or substituted fluorenyl group or an unsubstituted or substituted phenanthryl group.

4. The oxime compound according to claim 1, wherein Z is a C1-C20 halogenated aliphatic hydrocarbon group or a C6-C14 halogenated aromatic hydrocarbon group.

5. The oxime compound according to claim 1, wherein $Q^1$ and $Q^2$ each independently represent a fluorine atom or a trifluoromethyl group.

6. The oxime compound according to claim 1, wherein $R^1$ is a C1-C30 aliphatic hydrocarbon group in which one or more methylene groups may be replaced by —O—, —S— or —N($R^c$)—, and which may be substituted with at least one selected from the group consisting of a hydroxyl group and a halogen atom.

7. The oxime compound according to claim 1, wherein $R^1$ is a C1-C30 aliphatic hydrocarbon group in which one or more methylene groups are replaced by —CO—.

8. The oxime compound according to claim 1, wherein $R^1$ is a C1-C30 aliphatic hydrocarbon group having an acryloyloxy group or a methacryloyloxy group, and one or more methylene groups in the aliphatic hydrocarbon group may be replaced by —O—, —S—, —N($R^c$)—, —CO— or —CO—O—.

9. The oxime compound according to claim 1, wherein the oxime compound represented by the formula (I) is an oxime compound represented by the formula (III):

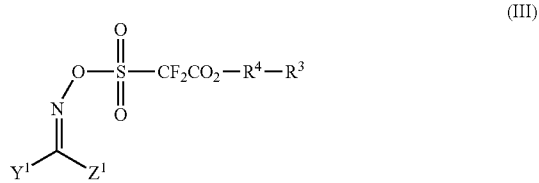

(III)

wherein $Y^1$ represents a phenyl group which may be substituted with a C1-C20 aliphatic hydrocarbon group having an acryloyloxy group or a methacryloyloxy group, a naphthyl group which may be substituted with a C1-C20 aliphatic hydrocarbon group having an acryloyloxy group or a methacryloyloxy group, a biphenyl group which may be substituted with a C1-C20 aliphatic hydrocarbon group having an acryloyloxy group or a methacryloyloxy group, an anthryl group which may be substituted with a C1-C20 aliphatic hydrocarbon group having an acryloyloxy group or a methacryloyloxy group, a fluorenyl group which may be substituted with a C1-C20 aliphatic hydrocarbon group having an acryloyloxy group or a methacryloyloxy group or a phenanthryl group which may be substituted with a C1-C20 aliphatic hydrocarbon group having an acryloyloxy group or a methacryloyloxy group, and one or more methylene groups in the C1-C20 aliphatic hydrocarbon group may be replaced by —O—, —S—, —N($R^c$)—, —CO— or —CO—O—, $R^c$ represents a hydrogen atom or a linear or branched chain C1-C4 aliphatic hydrocarbon group, $Z^1$ represents a C1-C20 halogenated aliphatic hydrocarbon group or a C6-C14 halogenated aromatic hydrocarbon group, $R^3$ represents a C3-C30 monocyclic or polycyclic aliphatic hydrocarbon group in which one or more methylene groups may be replaced by —O— or —CO—, and which may be substituted with a hydroxyl group, $R^4$ represents a single bond or a C1-C20 divalent aliphatic hydrocarbon group in which one or more methylene groups may be replaced by —O—, —S— or —N($R^c$)—.

10. The oxime compound according to claim 9, wherein $Y^1$ is a phenyl group, a naphthyl group, a biphenyl group, an anthryl group, a fluorenyl group or a phenanthryl group.

11. The oxime compound according to claim 9, wherein $R^3$ is a C3-C30 monocyclic or polycyclic aliphatic hydrocarbon group in which one or more methylene groups is replaced by —CO—.

12. The oxime compound according to claim 1, wherein the oxime compound represented by the formula (I) is an oxime compound represented by the formula (Va):

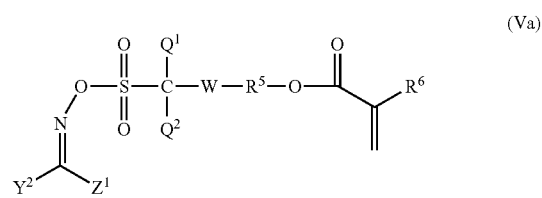

(Va)

wherein $Y^2$ represents an unsubstituted or substituted phenyl group, an unsubstituted or substituted naphthyl group, an unsubstituted or substituted biphenyl group, an unsubstituted or substituted anthryl group, an unsubstituted or substituted fluorenyl group or an unsubstituted or substituted phenanthryl group, $Z^1$ represents a C1-C20 halogenated aliphatic hydrocarbon group or a C6-C14 halogenated aromatic hydrocarbon group, $R^5$ represents a C1-C30 divalent aliphatic hydrocarbon group in which one or more methylene groups may be replaced by —O—, —S— or —N($R^c$)—, $R^c$ represents a hydrogen atom or a linear or branched chain C1-C4 aliphatic hydrocarbon group, $R^6$ represents a hydrogen atom or a methyl group, W represents —CO—O—, —CH$_2$O— or —CH$_2$O—CO—, and $Q^1$ and $Q^2$ each independently represent a fluorine atom or a C1-C6 perfluoroalkyl group.

13. The oxime compound according to claim 12, wherein $Q^1$ and $Q^2$ are fluorine atoms and W is —CO—O—.

14. The oxime compound according to claim 12, wherein $R^5$ is a C1-C20 divalent aliphatic hydrocarbon group in which one or more methylene groups may be replaced by —O—, —S— or —N($R^c$)—.

15. A polymer comprising a structural unit derived from an oxime compound according to claim 12.

16. The polymer according to claim 15, wherein the polymer contains a structural unit having an acid-labile group in addition to the structural unit derived from an oxime compound according to claim 12.

17. A resist composition comprising a resin and the polymer according to claim 15 as an acid generator.

18. A resist composition comprising a resin and the oxime compound according to claim 1 as an acid generator.

19. The resist composition according to claim 18 or 17, wherein the resin is a resin comprising a structural unit having an acid-labile group and being insoluble or poorly soluble in an aqueous alkali solution but becoming soluble in an aqueous alkali solution by the action of an acid.

20. The resist composition according to claim 18 or 17, wherein the resist composition further contains the other acid generator.

21. A process for producing an oxime compound represented by the formula (I):

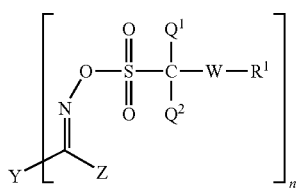

(I)

wherein Y represents an unsubstituted or substituted n-valent C6-C14 aromatic hydrocarbon group, n represents an integer of 1 to 6, $R^1$ represents a C1-C30 aliphatic hydrocarbon group, a C6-C14 aromatic hydrocarbon group, a C4-C10 heteroaromatic hydrocarbon group, a C1-C20 alkyl group having a C6-C14 aromatic hydrocarbon group or a C1-C20 alkyl group having a C4-C10 heteroaromatic hydrocarbon group, and one or more methylene groups in the aliphatic hydrocarbon groups may be replaced by —O—, —S—, —CO—, —CO—O—, —SO$_2$— or —N($R^c$)—, and the aliphatic hydrocarbon group, the aromatic hydrocarbon group, the heteroaromatic hydrocarbon group and the alkyl group may be respectively substituted with at least one selected from the group consisting of a hydroxyl group, an acryloyloxy group, a methacryloyloxy group, a halogen atom, a cyano group, —OR$^2$, —CO—OR$^2$, —O—CO—OR$^2$, —O—CO—R$^2$, —SO$_2$—OR$^2$, —O—SO$_2$—R$^2$ and —SO$_2$R$^2$, $R^2$ represents a linear or branched chain C1-C20 aliphatic hydrocarbon group in which one or more methylene groups may be replaced by —O—, —S—, —CO—, —CO—O— or —N($R^c$)—, and which may be substituted with at least one selected from the group consisting of a hydroxyl group, an acryloyloxy group and a methacryloyloxy group, $R^c$ represents a hydrogen atom or a linear or branched chain C1-C4 aliphatic hydrocarbon group, W represents —CO—O—, —CH$_2$O— or —CH$_2$O—CO—

$Q^1$ and $Q^2$ each independently represent a fluorine atom or a C1-C6 perfluoroalkyl group, Z represents a C1-C20 halogenated aliphatic hydrocarbon group, a C6-C14 halogenated aromatic hydrocarbon group, a cyano group, —CX$_2$—R$^1$ or —CX$_2$—SO$_2$—R$^1$, and X represents a halogen atom or a C1-C20 halogenated aliphatic hydrocarbon group, which comprises reacting a compound represented by the formula (VII):

(VII)

wherein Y, Z and n are the same meanings as defined above, with a compound represented by the formula (VIII):

(VIII)

wherein $R^1$, W, $Q^1$ and $Q^2$ are the same meanings as defined above, and L represents a halogen atom, in the presence of a base.

* * * * *